United States Patent [19]
Volrath et al.

[11] Patent Number: 5,939,602
[45] Date of Patent: *Aug. 17, 1999

[54] DNA MOLECULES ENCODING PLANT PROTOPORPHYRINOGEN OXIDASE AND INHIBITOR-RESISTANT MUTANTS THEREOF

[75] Inventors: Sandra L. Volrath, Durham; Marie A. Johnson, Raleigh; Eric R. Ward; Peter B. Heifetz, both of Durham, all of N.C.

[73] Assignee: Novartis Finance Corporation, New York, N.Y.

[*] Notice: This patent is subject to a terminal disclaimer.

[21] Appl. No.: 08/808,931

[22] Filed: Feb. 28, 1997

Related U.S. Application Data

[63] Continuation-in-part of application No. 08/472,028, Jun. 6, 1995, Pat. No. 5,767,373
[60] Provisional application No. 60/012,705, Feb. 28, 1996, provisional application No. 60/013,612, Feb. 28, 1996, and provisional application No. 60/020,003, Jun. 21, 1996.

[51] Int. Cl.$^6$ .............................. A01H 5/00; C12N 5/14; C12N 15/29; C12N 15/52; C12N 15/82
[52] U.S. Cl. ...................... 800/300; 435/320.1; 435/419; 435/440; 435/468; 536/23.2; 536/23.6; 800/278
[58] Field of Search ................................. 536/23.2, 23.6; 435/172.1, 172.3, 320.1, 419; 800/205, DIG. 15, DIG. 52, DIG. 26, DIG. 55, DIG. 27, DIG. 63, DIG. 43, DIG. 9, DIG. 17, DIG. 56, DIG. 58, DIG. 57; 47/58

[56] References Cited

U.S. PATENT DOCUMENTS

| | | | |
|---|---|---|---|
| 5,407,808 | 4/1995 | Halling et al. | 435/34 |
| 5,451,513 | 9/1995 | Maliga et al. | 435/172.3 |
| 5,767,373 | 6/1998 | Ward et al. | 800/205 |

FOREIGN PATENT DOCUMENTS

| | | |
|---|---|---|
| 0 360 750 | 9/1989 | European Pat. Off. |
| 0 478 502 A2 | 4/1992 | European Pat. Off. |
| WO 90/06748 | 6/1990 | WIPO . |
| WO 91/19418 | 12/1991 | WIPO . |
| WO 95/34659 | 12/1995 | WIPO . |
| WO 97/04088 | 2/1997 | WIPO . |
| WO 97/04089 | 2/1997 | WIPO . |
| WO 97/06250 | 2/1997 | WIPO . |

OTHER PUBLICATIONS

Narita et al., "Molecular cloning and characterization of a cDNA that encodes protoporphyrinogen oxidase of *Arabidopsis thaliana*", *Gene*, 182: 169–175 (1996).
Al–Hazimi et al., "Synthetic and Biosynthetic Studies of Porphyrins Part 7. The Action of Coproporphyrinogen Oxidase on Coproporphyrinogen IV: Syntheses of Photoporphyrin XIII, mesoporphyrin XIII, and Related Tricarboxylic Porphyrins", *J Chem Soc Perkin Trans. I*, 265–276 (1987).
Armbruster et al., "Herbicidal Action of Nitrophenyl Pyrazole Ether MON 12800: Immunolocalization, Ultrastructural, and Physiological Studies", *Pestice Biochemistry and Physiology*, 47: 21–35 (1993).
Becerril et al., "Acifluorfen Effects on Intermediates of Chlorophyll Synthesis in Green Cucumber Cotyledon Tissues", *Pesticide Biochemistry and Physiology*, 35: 119–126 (1989).
Brenner et al., "A Fluorometric Assay for Measurement of Protoporphyrinogen Oxidase Activity in Mammalian Tissue", *Clinica Chimica Acta*, 100: 259–266 (1980).
Brenner et al., "Cloning of murine ferrochelatase", *Proc. Natl. Acad. Sci. USA*, 88:849–853 (1991).
Camadro et al., "A New Assay for Protoporphyrinogen Oxidase—Evidence for a Total Deficiency in that Activity in a Heme–Less Mutant of *Saccharomyces cerevisiae*", *Biochemical and Biophysical Research Communications*, 106(3): 724–730 (1982).
Camadro et al., "Photoaffinity labeling of protoporphyrinogen oxidase, the molecular target of diphenylether–type herbicides", *Eur J of Biochem.*, 229: 669–674 (1995).
Camadro et al., "Molecular Properties of Yeast and Lettuce Protoporphyrinogen Oxidases", *Abstract Pap Am Chem. Soc.*, 111. (1–2) (1993).
Camadro et al., "Cloning and Characterization of the Yeast HEM14 Gene Codoing for Protoporphyrinogen Oxidase, the Molecular Target of Diphenyl Ether–type Herbicides", *The Journal of Biological Chemistry*, 271(15): 9120–9128 (1996).
Camadro et al., "Purification and Properties of Protoporphyrinogen Oxidase from the Yeast *Saccharomyces cerevisiae*: Mitochondrial Location and Evidence for a Precursor Form of the Protein", *The Journal of Biological Chemistry*, 269(51): 32085–32091 (1994).
Cardin et al., "Characterization of Protoporphyrinogen Oxidase from *Rhodopseudomonas capsulata*", *Abstracts of the Annual Meeting Am. Soc. Microbiol.*, Abstract #K–85, 207 (1986).
Che et al., "Localization of Target–Site of the Protoporphyrinogen Oxidase–Inhibiting Herbicide S–23142 in *Spinacia– leracea* L.", *Z. Naturforsch.*, 48(c): 350–355 (1993).

(List continued on next page.)

*Primary Examiner*—Douglas W. Robinson
*Assistant Examiner*—Amy J. Nelson
*Attorney, Agent, or Firm*—J. Timothy Meigs

[57] ABSTRACT

The present invention provides novel DNA sequences coding for plant protoporphyrinogen oxidase (protox) enzymes from soybean, wheat, cotton, sugar beet, rape, rice and sorghum. In addition, the present invention teaches modified forms of protox enzymes that are herbicide tolerant. Plants expressing herbicide tolerant protox enzymes taught herein are also provided. These plants may be engineered for resistance to protox inhibitors via mutation of the native protox gene to a resistant form or they may be transformed with a gene encoding an inhibitor-resistant from of a plant protox enzyme.

144 Claims, No Drawings

OTHER PUBLICATIONS

Corrigall et al., "Inhibition of Mammalian Protoporphyrinogen Oxidase by Acifluorfen", *Biochemistry and Molecular Biology International*, 34(6): 1283–1289 (1994).

Crews et al., "Synthesis and Herbicidal Activity of bis–Aryloxybenzenes, a New Class of Protox Inhibitors", *Abstracts of Papers American Chemical Society*, Abstract #044. 209(1–2) (1995).

Dailey T.A. et al., "Human protoporphyrinogen oxidase: Expression, purification, and characterization of the cloned enzyme", *Protein Science*, 5: 98–105 (1996).

Dailey et al., "Expression of a Cloned Protoporphyrinogen Oxidase", *The Journal of Biological Chemistry*, 269(2):813–815 (1994).

Dailey T.A. et al., "Cloning, Sequence, and Expression of Mouse Protoporphyrinogen Oxidase", *Archives of Biochemistry and Biophysics*, 324(2): 379–384 (1995).

Derrick, Peter Michael, "An investigation into the mode of action the herbicide M&B 39279", *Dissertation Abstracts International*, 50(10): 4283–B (1996).

Deybach et al., "The mitochondrial location of protoporphyrinogen oxidase", *Eur. J. Biochem.*, 149(2): 431–436 (1985).

Duke et al., "Protoporphyrinogen Oxidase as the Optimal Herbicide Site in the Porphyrin Pathway", *ACS SYMP. SER.—Porphyric Pesticides* 191–204 (1994).

Duke et al., "Protoporphyrinogen Oxidase–Inhibiting Herbicides", *Weed Science*, 39: 465–473 (1991).

Duke et al., "Porphyric Pesticides Chemistry, Toxicology, and Pharmaceutical Applications", *ACS Symposium Series 559, American Chemical Society*, 1–318 (1994).

Duke et al., "Prospects for Herbicides Designed for Sites of Action in the Porphyrin Pathway Beyond Protoporphyrinogen Oxidase", *Abstracts of Papers American Chemical Society*, Abstract #129, 206(1–2) (1993).

Duke, S.O., "Pesticides that Act Through Prophyrin Accumulation", *Abstracts of the 22nd Annual Meeting of the American Society for Photobiology*, Abstract #SPM–B2, 59 (Spec. Issue) (1994).

Elder et al., "A Radiochemical Method for the Measurement of Coproporphyrinogen Oxidase and the Utilization of Substrates other than Coproporphyrinogen III by the Enzyme from Rat Liver", *Biochem. J.*, 169: 205–214 (1978).

Falbel et al., "Characterization of a Family of Chlorophyll–Deficient Wheat (*Triticum*) and Barley (*Hordeum vulgare*) Mutants with Defects in the Magnesium–Insertion Step of Chlorophyll Biosynthesis", *Plant Physiology (Rockville)*, 104: 639–648 (1994).

Ferreira et al., "Organization of the Terminal Two Enzymes of the Heme Biosynthetic Pathway Orientation of Protoporphyrinogen Oxidase and Evidence for a Membrane Complex*", *The Journal of Biolocial Chemistry*, 263(8): 3835–3839 (1988).

Frustaci et al., "The *Escherichia–coli* vis A Gene Encodes Ferrochelatase, the Final Enzyme of the Heme Biosynthetic Pathway", *Journal of Bacteriology*, 175(7): 2154–2156 (1993).

Gollub et al., "Yeast Mutants Deficient in Heme Biosynthesis and a Heme Mutant Additionally Blocked in Cyclization of 2 3 Oxidosqualene*", *The Journal of Biological Chemistry*, 252(9): 2846–2854 (1977).

Guo et al., "High–performance liquid chromatographic assays for protoporphyrinogen oidase and ferrochelatase in human leukocytes", *Journal of Chromatography Biomedical Applications*, 566: 383–396 (1991).

Hallahan et al., "Mode of Action Studies on a Chiral Diphenyl Ether Peroxidizing Herbicide Correlation between Differential Inhibition of Protoporphyrinogen IX Oxidase Activity and Induction of Tetrapyrrole Accumulation by the Enantiomers", *Plant Physiol. (Bethesda)*, 100: 1211–1216 (1992).

Hansson et al., "Cloning and Characterization of the *Bacillus subtilis hemEHY* Gene Cluster, Which Encodes Protoheme IX Biosynthetic Enzymes", *J. Bacteriol.* 174(24) 8081–8093 (1992).

Hansson et al., "*Bacillus subtilis* Hem Y Is a Peripheral Membrane Protein Essential for Protoheme IX Synthesis Which Can Oxidize Coproporphyrinogen III and Protoporphyrinogen IX", *Journal of Bacteriology*, 176(19): 5962–5970 (1994).

Ihara et al., "Peroxidizing Phytotoxic Activity of 1,3, 4–Thiadiazolidine–2–thiones and 1,2,4–Triazolidine–3, 5–dithiones", *Journal of Pesticide Science*, 20: 41–47 (1995).

Iida et al., "Isomerization and Peroxidizing Phytotoxicity of Thiadiazolidine–thione Compounds", *Z. Naturforsch.*, 50(c): 186–192 (1995).

Jacobs et al., "Oxidation of protoporphyrinogen to protoporphyrin, a step in chlorophyll and haem biosynthesis", *Biochem. J.*, 244: 219–224 (1987).

Jacobs, J. M. et al., "Terminal Enzymes of Heme Biosynthesis in the Plant Plasma Membrane", *Archives of Biochemistry and Biophysics*, 323(2): 274–278 (1995).

Jacobs J.M. et al., "Effects of the Diphenyl Dther Herbicides on Porphyrin Accumulation by Cultured Hepatocytes", *J. Biochem. Toxicology*, 7(2): 87–95 (1992).

Jacobs J.M. et al., "Protoporphyrinogen Oxidation, an Enzymatic Step in Heme and Chlorophyll Synthesis: Partial Characterization of the Reaction in Plant Organelles and Comparison with Mammalian and Bacterial Systems[1]", *Archives of Biochemistry and Biophysics*, 229(1): 312–319 (1984).

Jacobs J.M. et al., "Effects of the Photobleaching Herbicide, Acifluorfen–methyl, on Protoporphyrinogen Oxidation in Barley Organelles, Soybean Root Mitochondria Soybean Root Nodules, and Bacteria", *Archives of Biochemistry and Biophysics*, 280(2): 369–375 (1990).

Jacobs et al., "Effect of Diphenyl Ether Herbicides on Oxidation of Protoporphyrinogen to Protoporphyrin in Organellar and Plasma Membrane Enriched Fractions of Barley", *Plant Physiol. (Bethesda)*, 97: 197–203 (1991).

Jacobs et al., "Porphyrin Accumulation and Export by Isolated Barley (Hordeum–vulgare) Plastids. Effect of Diphenyl Ether Herbicides", *Plant Physiol. (ROCKV)*, 101: 1181–1188 (1993).

Jacobs N. et al., "Protoporphyrinogen oxidation in plants and rhizobia", *Plant Physiol. (Bethesda)*, #1055 (4 Suppl.) (1989).

Jacobs N.J. et al., "Mechanism of Protoporphyrin IX Accumulation in Plant Cells Treated with Herbicides Inhibiting Protoporphyrinogen Oxidase", *Abstract Pap Am. Chem. Soc.*, Abstract #113, 206 (1–2) (1993).

Jacobs N.J. et al., "Microbial Oxidation of Protoporphyrinogen an Intermediate in Heme and Chlorophyll Biosynthesis", *Archives of Biochemistry and Biophysics*, 197(2): 396–403 (1979).

Jacobs N.J. et al., "Characteristics of Purified Protoporphyrinogen Oxidase from Barley", *Biochemical and Biophysical Research Communications*, 161(2): 790–796 (1989).

Jacobs N.J. et al., "Assay for Enzymatic Protoporphyrinogen Oxidation, a Late Step in Heme Synthesis", *Enzyme (Basel)*, 28: 206–217 (1982).

Jacobs N.J. et al., "Protoporphyrinogen Oxidation, a Step in Heme Synthesis in Soybean Root Nodules and Free–Living Rhizobia", *Journal of Bacteriology*, 171(1): 573–576 (1989).

Jansen et al., "Mode of Evolved Photooxidant Resistance to Herbicides and Xenobiotics", *Z. Naturforsch Sect. Biosci.*, 45(c): 463–469 (1990).

Kataoka et al., "Isolation and Partial Characterization of Mutant *Chlamydomas reinhardtii* Resistant to Herbicide S–23142", *J. Pesticide Sci.*, 15:499–451 (1990).

Klemm et al., "Protoporphyrinogen oxidation coupled to nitrite reduction with membranes from *Desulfovibrio–gigas*", *FEMS Microbiology Letters*, 61: 61–64 (1989).

Klemm et al., "Purification and Properties of Protoporphyrinogen Oxidase from an Anaerobic Bacterium, *Desulfovibrio–gigas*", *Journal of Bacteriology*, 169(11): 5209–5215 (1987).

Kohno et al., "Peroxidizing Phytotoxic Activity of Pyrazoles", *Journal of Pesticide Science*, 20: 137–143 (1995).

Kolarov et al., "Rat Liver Protoporphyrinogen IX Oxidase: Site of Synthesis and Factor Influencing its Activity", *Biochemical and Biophysical Research Communications*, 116(2): 383–387 (1983).

Komives et al., "Mechanisms of Plant Tolerance to Phytodynamic Herbicides", *Abstract Pap Am. Chem. Soc.*, Abstract #128, 206(1–2) (1993).

Labbe et al., "Fluorometric assays for coproporphyrinogen oxidase and protoporphyrinogen oxidase", *Analytical Biochemistry*, 149: 248–260 (1985).

Labbe–Bois R., "The Ferrochetelase from *Saccharomyces–Cerevisiae*. Sequence, Disruption, and Expression of its Structural Gene HEM15*", *The Journal of Biological Chemistry*, 265(13): 7278–7283 (1990).

Lee et al., "Cellular Localization of Protoporphyrinogen–Oxidizing Activities of Etiolated Barley (*Hordeum vulgare* L.) Leaves", *Plant Physiol.*, 102:881–889 (1993).

Lee et al., "Peroxidase Involvement in the Accumulation of Protoporphyrin IX in Acifluorfen–Methyl–Treated Plant Tissues", *Plant Physiology (Rockville)*, 105(1 Suppl.): 125 (1994).

Lee H.J. et al., "Protoporphyrinogen IX–Oxidizing Activities Involved in the Mode of Action of Peroxidizing Herbicides", *Journal of Agricultural and Food Chemistry*, 42(11): 2610–2618 (1994).

LI et al., "An h.p.l.c. assay for protoporphyrinogen oxidase activity in rat liver", *Biochem. J.*, 243: 863–866 (1987).

Lyga et al., "Synthesis, Mechanism of Action, and QSAR of Herbicidal 3–Substituted–2–aryl–4,5,6,7–tetrahydroindazoles", *Pesticide Science*, 42: 29–36 (1994).

Madsen et al., "A soybean coproporphyrinogen oxidase gene is highly expressed in root nodules", *Plant Molecular Biology*, 23: 35–43, (1993).

Martasek et al., "Molecular cloning, sequencing, and functional expression of a cDNA encoding human coproporphyrinogen oxidase", *Proceedings of the National Academy of Sciences of the United States of America*, 91: 3024–3028 (1994).

Martasek et al., "Homozygous hereditary coproporphyria caused by an arginine to tryptophan substitution in coproporphyrinogen oxidase and common intragenic polymorphisms", *Human Molecular Genetics*, 3(3): 477–480 (1994).

Matringe et al., "Localization within Chloroplasts of Protoporphyrinogen Oxidase, the Target Enzyme for Diphenylether–like Herbicides", *The Journal of Biological Chemistry*, 267(7):4646–4651 (1992).

Matringe et al., "Protoporphyrinogen oxidase as a molecular target for diphenyl ether herbicides", *Biochem. J.*, 260:231–235 (1989).

Matringe et al., "Protoporphyrinogen oxidase inhibition by three peroxidizing herbicides: oxadiazon, LS 82–556 and M&B 39279", *FEBS Letters*, 245(1,2): 35–38 (1989).

Matringe et al., "Characterization of [$^3$H]acifluorfen binding to purified pea etioplasts, and evidence that protoporphyrinogen oxidase specifically binds acifluorfen", *Eur. J. Biochem.*, 209: 861–868 (1992).

Matsumoto et al., "Variation in Crop Response to Protoporphyrinogen Oxidase Inhibitors", *Abstract. Pap Am. Chem. Soc.*, Abstract #124, 206 (1–2) (1993).

Matsumoto et al., "A Rapid and Strong Inhibition of Protoporphyrinogen Oxidase from Several Plant Species by Oxyfluorfen", *Pesticide Biochemistry and Physiology*, 47: 113–118 (1993).

Mullet, John E., "Dynamic Regulation of Chloroplast Transcription", *Plant Physiology*, 103: 309–313 (1993).

Nakayashiki et al., "Cloning and sequencing of a previously unidentified gene that is involved in the biosynthesis of heme in *Escherichia coli*", *Gene (Amsterdam)*, 153: 67–70 (1995).

Nandihalli et al., "The Porphyrin Pathway as a Hervicide Target Site", *Abstract Pap Am. Chem. Soc.*, 203 (1–3) (1992).

Nandihalli et al., "Relationships between Molecular Properties and Biological Activities of O–Phenyl Pyrrolidino– and Piperidinocarbamate Herbicides", *J. Agri. Food Chem.*, 40(10): 1993–2000 (1992).

Nandihalli et al., "Correlation of Protoporphyrinogen Oxidase Inhibition by O–Phenyl Pyrrolidino– and Piperidino–Carbamates with their Herbicidal Effects", *Pestic. Sci.*, 35: 227–235 (1992).

Nandihalli et al., "Enantioselectivity of Protoporphyrinogen Oxidase–Inhibiting Herbicides", *Pesticide Science*, 40: 265–277 (1994).

Nicolaus et al., "Binding Affinities of Peroxidizing Herbicides to Protoporphyrinogen Oxidase from Corn", *Pesticide Biochemistry and Physiology*, 51: 20–29 (1995).

Nicolaus et al., "Molecular Aspects of Herbicide Action on Protoporphyrinogen Oxidase", *Z. Naturforsch*, 48(c): 326–333 (1993).

Nishimura et al., "Cloning of a Human cDNA for Protoporphyrinogen Oxidase by Complementation in Vivo of a hemG Mutant of *Escherichia coli*", *J. of Biological Chemistry*, 270(14): 8076–8080 (1995).

Oshio et al., "Isolation and Characterization of a *Chlamydomonas reinhardtii* Mutant Resistant to Photobleaching Herbicides", *Z. Naturforsch*. 48c: 339–344 (1993).

Pornprom et al., "Chracterization of Oxyfluorfen Tolerance in Selected Soybean Cell Line", *Pesticide Biochemistry and Physiology* 50: 107–114 (1994).

Pornprom et al., "Selection for Herbicide Tolerance in Soybean Using Cell Suspension Culture", *Weed Research*, 39(2): 102–108 (1994).

Prasad A.R.K. et al., "Generation of Resistance to the Diphenyl Ether Herbicide Acifluorfen by Mel Cells*", *Biochemical and Biophysical Research Communications*, 215(1): 186–191 (1995).

Proulx et al., "Characteristics of murine protoporphyrinogen oxidase", *Protein Science*, 1: 801–809 (1992).

Proulx et al., "In situ conversion of coproporphyrinogen to heme by murine mitochondria: Terminal steps of the heme biosynthetic pathway", *Protein Science*, 2: 1092–1098 (1993).

Ramseier et al., "Cloning of a DNA region from *Bradyrhizobium–japonicum* encoding pleiotropic functions in the heme metabolism and respiration", *Arch. Microbiol.*, 151: 203–212 (1989).

Reddy K.N., "Modulators of the Porphyrin Pathway Beyond Protox", *Abstract Pap. Am. Chem. Soc.*, Abstract #127, 206(1–2) (1993).

Roberts et al., "Partial characterization and assignment of the gene for protoporphyrinogen oxidase and variegate porphyria to human chromosome 1q23", *Human Molecular Genetics*, 4(12): 2387–2390 (1995).

Sato et al., "Isomerization and Peroxidizing Phytotoxicity of Thiadiazolidine Herbicides", *Z. Naturforsch.*, 49(c): 49–56 (1994).

Sasarman et al., "Nucleotide sequence of the hemG gene involved in the protoporphyrinogen oxidase activity of *Escherichia coli* K12", *Can. J. Microbiol.*, 39:1155–1161 (1993).

Scalla et al., "Inhibitors of Protoporphyrinogen Oxidase as Herbicides: Diphenyl Ethers and Related Photobleaching Molecules", *Reviews of Weed Science*, 6: 103–132 (1994).

Sherman et al., "Tissue and Cellular Localization of Porphyrins in Cucumber Cotyledon Tissue with Inhibited Protoporphyrinogen Oxidase", *Plant Physiol. (Bethesda)*, 93 (1Suppl.) (1990).

Sherman et al., "Pyrazole Phenyl Ether Herbicides Inhibit Protoporphyrinogen Oxidase", *Pesticide Biochemistry and Physiology*, 40: 236–245 (1991).

Sherman et al., "Physiological Basis for Differential Sensitivities of Plant Species to Protoporphyrinogen Oxidase–Inhibiting Herbicides", *Plant Physiol.* 97: 280–287 (1991).

Shibata et al., "Isolation and Characterization of a *Chlamydomonas reinhardtii* Mutant Resistant to an Experimental Herbicide S–23142, Which Inhibits Chlorophyll Synthesis", *Research in Photosynthesis*, III:567–570 (1992).

Shimizu et al., "A Novel Isourazole Herbicide, Fluthiacet–Methyl, is a Potent Inhibitor of Protoporphyrinogen Oxidase after Isomerization by Glutathione S–Transferase", *Plant and Cell Physiology*, 36(4): 625–632 (1995).

Siepker et al., "Purification of bovine protoporphyrinogen oxidase: immunological cross–reactivity and structural relationship ferrochelatase", *Biochimica et Biophysica Acta*, 931: 349–358 (1987).

Smith et al., "Investigation of the subcellular location of the tetrapyrrole–biosynthesis enzyme coproporphyrinogen oxidase in higher pants", *Biochem. J.*, 292: 503–508 (1993).

Staub et al., "Long Regions og Homologous DNA Are Incorporated into the Tobacco Plastid Genome by Transformation", *The Plant Cell*, 4: 39–45 (1992).

Struhl, "They new yeast genetics", *Nature* 305:3 91–397 (1983).

Svab et al., "High–frequency plastid transformationin tobacco by selection for a chimeric aadA gene", *Proc. Natl. Acad. Sci. USA*, 90: 913–917 (1993).

Taketani et al., "The Human Protoporphyrinogen Oxidase Gene (PPOX): Organization and Location to Chromosome 1", *Genomics*, 29: 698–703 (1995).

Tietjen K.G., "Quinone Activation of Protoporphyrinogen Oxidase of Barley Plastids", *Pestic. Sci.*, 33: 467–471 (1991).

Tonkyn et al., "Differential expression of the partially duplicated chloroplast S10 ribosomal operon", *Mol Gen Genet*, 241: 141–152 (1993).

Troup et al., "Isolation of the hemF Operon Containing the Gene for the *Escherichia coli* Aerobic Coproporphyrinogen III Oxidase by In Vivo Complementation of a Yeast HEM13 Mutant", *Journal of Bacteriology*, 176(3):673–680 (1994).

Troup et al., "Cloning and Characterization of the *Escherichia coli hemN* Gene Encoding the Oxygen–Independent Coproporphyrinogen III Oxidase", *Journal of Bacteriology*, 177(11): 3326–3331 (1995).

Varsano et al., "Competitive interaction of three peroxidizing herbicides with the binding of [$^3$H]acifluorfen to corn etioplast membranes", *FEBS*, 272(1,2): 106–108 (1990).

Viljoen et al., "Protoporphyrinogen oxidase and ferrochelatase in porphyria variegata", *European Journal of Clinical Investigation*, 13: 283–287 (1983).

Wang et al., "New Assay Method for Protoporphyrinogen Oxidase Inhibitors Using Chloroplasts Isolated from *Spinacia oleracea* L", *Bioscience Biotechnology and Biochemistry*, 57(12): 2205–2206 (1993).

Wepplo et al., "Synthesis and Herbicidal Activity of 5–Aryloxybenzisoxazole–3–Acetate Esters", *Abstr. Pap. Am. Chem. Soc.*, Abstract #16, 205(1–2) (1993).

Witkowski et al., "Inhibition of Plant Protoporphyrinogen Oxidase by the Herbicide Acifluorfen–Methyl", *Plant Physiol. (Bethesda)*, 90: 1239–1242 (1989).

Wright et al., "Herbicidal Activity of UCC–C4243 and Acifluorfen Is Due to Inhibition of Protoporphyrinogen Oxidase", *Weed Science*, 43: 47–54 (1995).

Xu et al., "The Genes Required for Heme Synthesis in *Salmonella–typhimurium* Include Those Encoding Alternative Functions for Aerobic and Anaerobic Coproporphyrinogen Oxidation", *Journal of Bacteriology*, 174(12): 3953–3963 (1992).

Xu et al., "An Oxygen–Dependent Coproporphyrinogen Oxidase Encoded by the hemF Gene of *Salmonella–typhimurium*", *Journal of Bacteriology*, 175(16): 4990–4999 (1993).

Yamato et al., "A Tobacco Soluble Protoporphyrinogen–oxidizing Enzyme Similar to Plant Peroxidases in Their Amino Acid Sequences and Immunochemical Reactivity", *Bioscience Biotechnology and Biochemistry*, 59(3): 558–559 (1995).

Yamato et al., "Purification and characterization of a protoporphyrinogen–oxidizing enzyme with peroxidase activity and light–dependent herbicide resistance in tobacco cultured cells", *Pestic. Biochem. Physiol.*, 50: 72–82 (1994).

Embl Sequence Database Acc. No. M22063 Rel. 19 Apr. 22, 1989.

Embl Sequence Database Acc. No. T43573, Rel. No. 42, Feb. 3, 1995.

Ichinose et al., "Selection and Characterization of Protoporphyrinogen Oxidase Inhibiting Herbicide (S23142) Resistant Photomixotrophic Cultured Cells of *Nicotiana tabacum*", *J. Plant Physiol.*, 146: 693–698 (1995).

DNA MOLECULES ENCODING PLANT PROTOPORPHYRINOGEN OXIDASE AND INHIBITOR-RESISTANT MUTANTS THEREOF

CROSS-REFERENCE TO RELATED APPLICATIONS

This application claims the benefit of U.S. Provisional Application No. 60/012,705, filed Feb. 28, 1996; U.S. Provisional Application No. 60/013,612, filed Feb. 28, 1996; and U.S. Provisional Application No. 60/020,003, filed Jun. 21, 1996.

This application is also a continuation-in-part of U.S. application Ser. No. 08/472,028, filed Jun. 6, 1995 now U.S. Pat. No. 5,767,373, issued Jun. 16, 1998.

FIELD OF THE INVENTION

The invention relates generally to the plant enzyme protoporphyrinogen oxidase ("protox"). In particular, the invention relates to DNA molecules encoding this enzyme and to modified, inhibitor-resistant forms of this enzyme. The invention further relates to methods for tissue culture selection and herbicide application based on these modified forms.

BACKGROUND OF THE INVENTION

I. The Protox Enzyme and its Involvement in the Chlorophyll/Heme Biosynthetic Pathway The biosynthetic pathways that lead to the production of chlorophyll and heme share a number of common steps. Chlorophyll is a light harvesting pigment present in all green photosynthetic organisms. Heme is a cofactor of hemoglobin, cytochromes, P450 mixed-function oxygenases, peroxidases, and catalyses (see, e.g. Lehninger, *Biochemistry*. Worth Publishers, New York (1975)), and is therefore a necessary component for all aerobic organisms.

The last common step in chlorophyll and heme biosynthesis is the oxidation of protoporphyrinogen IX to protoporphyrin IX. Protoporphyrinogen oxidase (referred to herein as "protox") is the enzyme that catalyzes this last oxidation step (Matringe et al., *Biochem. J.* 260: 231 (1989)).

The protox enzyme has been purified either partially or completely from a number of organisms including the yeast Saccharomyces cerevisiae (Labbe-Bois and Labbe, In *Biosynthesis of Heme and Chlorophyll*, E. H. Dailey, ed. McGraw Hill: New York, pp. 235–285 (1990)), barley etioplasts (Jacobs and Jacobs, *Biochem. J.* 244: 219 (1987)), and mouse liver (Dailey and Karr, *Biochem.* 26: 2697 (1987)). Genes encoding protox have been isolated from two prokaryotic organisms, *Escherichia coli* (Sasarman et al., *Can. J. Microbiol.* 39: 1155 (1993)) and *Bacillus subtilis* (Dailey et al., *J. Biol. Chem.* 269: 813 (1994)). These genes share no sequence similarity; neither do their predicted protein products share any amino acid sequence identity. The *E. coli* protein is approximately 21 kDa, and associates with the cell membrane. The *B. subtilis* protein is 51 kDa, and is a soluble, cytoplasmic activity.

Protox encoding genes have now also been isolated from humans (see Nishimura et al., *J. Biol. Chem.* 270(14): 8076–8080 (1995) and plants (International application no. PCT/IB95/00452 filed Jun. 8, 1995, published Dec. 21, 1995 as WO 95/34659).

II. The Protox Gene as a Herbicide Target

The use of herbicides to control undesirable vegetation such as weeds or plants in crops has become an almost universal practice. The relevant market exceeds a billion dollars annually. Despite this extensive use, weed control remains a significant and costly problem for farmers.

Effective use of herbicides requires sound management. For instance, time and method of application and stage of weed plant development are critical to getting good weed control with herbicides. Since various weed species are resistant to herbicides, the production of effective herbicides becomes increasingly important.

Unfortunately, herbicides that exhibit greater potency, broader weed spectrum and more rapid degradation in soil can also have greater crop phytotoxicity. One solution applied to this problem has been to develop crops that are resistant or tolerant to herbicides. Crop hybrids or varieties resistant to the herbicides allow for the use of the herbicides without attendant risk of damage to the crop. Development of resistance can allow application of a herbicide to a crop where its use was previously precluded or limited (e.g. to pre-emergence use) due to sensitivity of the crop to the herbicide. For example, U.S. Pat. No. 4,761,373 to Anderson et al. is directed to plants resistant to various imidazolinone or sulfonamide herbicides. The resistance is conferred by an altered acetohydroxyacid synthase (AHAS) enzyme. U.S. Pat. No. 4,975,374 to Goodman et al. relates to plant cells and plants containing a gene encoding a mutant glutamine synthetase (GS) resistant to inhibition by herbicides that were known to inhibit GS, e.g. phosphinothricin and methionine sulfoximine. U.S. Pat. No. 5,013,659 to Bedbrook et al. is directed to plants that express a mutant acetolactate synthase that renders the plants resistant to inhibition by sulfonylurea herbicides. U.S. Pat. No. 5,162,602 to Somers et al. discloses plants tolerant to inhibition by cyclohexanedione and aryloxyphenoxypropanoic acid herbicides. The tolerance is conferred by an altered acetyl coenzyme A carboxylase(ACCase).

The protox enzyme serves as the target for a variety of herbicidal compounds. The herbicides that inhibit protox include many different structural classes of molecules (Duke et al., *Weed Sci.* 39: 465 (1991); Nandihalli et al., *Pesticide Biochem. Physiol.* 43: 193 (1992); Matringe et al., *FEBS Lett.* 245: 35 (1989); Yanase and Andoh, *Pesticide Biochem. Physiol.* 35: 70 (1989)). These herbicidal compounds include the diphenylethers {e.g. acifluorfen, 5-[2-chloro-4-(trifluoromethyl)phenoxy]-2-nitrobezoic acid; its methyl ester; or oxyfluorfen, 2-chloro-1-(3-ethoxy-4-nitrophenoxy)-4-(trifluorobenzene)}, oxidiazoles, (e.g. oxidiazon, 3-[2,4-dichloro-5-(1-methylethoxy)phenyl]-5-(1,1-dimethylethyl)-1,3,4-oxadiazol-2-(3H)-one), cyclic imides (e.g. S-23142,N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-[1-(2,3,4-trichlorophenyl)-4-nitropyrazolyl-5-oxy] propionate; M&B 39279), pyridine derivatives (e.g. LS 82-556), and phenopylate and its O-phenylpyrrolidino- and piperidinocarbamate analogs. Many of these compounds competitively inhibit the normal reaction catalyzed by the enzyme, apparently acting as substrate analogs.

Typically, the inhibitory effect on protox is determined by measuring fluorescence at about 622 to 635 nm, after excitation at about 395 to 410 nM (see, e.g. Jacobs and Jacobs, *Enzyme* 28: 206 (1982); Sherman et al., *Plant Physiol.* 97: 280 (1991)). This assay is based on the fact that protoporphyrin IX is a fluorescent pigment, and protoporphyrinogen IX is nonfluorescent.

The predicted mode of action of protox-inhibiting herbicides involves the accumulation of protoporphyrinogen IX in the chloroplast. This accumulation is thought to lead to leakage of protoporphyrinogen IX into the cytosol where it is oxidized by a peroxidase activity to protoporphyrin IX. When exposed to light, protoporphyrin IX can cause formation of singlet oxygen in the cytosol. This singlet oxygen can in turn lead to the formation of other reactive oxygen species, which can cause lipid peroxidation and membrane disruption leading to rapid cell death (Lee et al., *Plant Physiol.* 102: 881 (1993)).

Not all protox enzymes are sensitive to herbicides that inhibit plant protox enzymes. Both of the protox enzymes encoded by genes isolated from *Escherichia coli* (Sasarman et al., *Can. J. Microbiol.* 39: 1155 (1993)) and *Bacillus subtilis* (Dailey et al., *J. Biol. Chem.* 269: 813 (1994)) are resistant to these herbicidal inhibitors. In addition, mutants of the unicellular alga *Chlamydomonas reinhardtii* resistant to the phenylimide herbicide S-23142 have been reported (Kataoka et al., *J. Pesticide Sci.* 15: 449 (1990); Shibata et al., In *Research in Photosynthesis*, Vol. III, N. Murata, ed. Kluwer: Netherlands. pp. 567–570 (1992)). At least one of these mutants appears to have an altered protox activity that is resistant not only to the herbicidal inhibitor on which the mutant was selected, but also to other classes of protox inhibitors (Oshio et al., *Z. Naturforsch.* 48c: 339 (1993); Sato et al., In *ACS Symposium on Porphyric Pesticides*, S. Duke, ed. ACS Press: Washington, D.C. (1994)). A mutant tobacco cell line has also been reported that is resistant to the inhibitor S-21432 (Che et al.,. *Z. Naturforsch.* 48c: 350 (1993).

SUMMARY OF THE INVENTION

The present invention provides isolated DNA molecules and chimeric genes encoding the protoporphyrinogen oxidase (protox) enzyme from wheat, soybean, cotton, sugar beet, rape, rice, and sorghum. The sequence of such isolated DNA molecules are set forth in SEQ ID NOs: 9 (wheat), 11 (soybean), 15 (cotton), 17 (sugar beet), 19 (rape), 21 (rice), and 23 (sorghum).

The present invention also provides modified forms of plant protoporphyrinogen oxidase (protox) enzymes that are resistant to compounds that inhibit unmodified naturally occurring plant protox enzymes, and DNA molecules coding for such inhibitor-resistant plant protox enzymes. The present invention includes chimeric genes and modified forms of naturally occurring protox genes that can express the inhibitor-resistant plant protox enzymes in plants.

Genes encoding inhibitor-resistant plant protox enzymes can be used to confer resistance to protox-inhibitory herbicides in whole plants and as a selectable marker in plant cell transformation methods. Accordingly, the present invention also includes plants, including the descendants thereof, plant tissues and plant seeds containing plant expressible genes encoding these modified protox enzymes. These plants, plant tissues and plant seeds are resistant to protox-inhibitors at levels that normally are inhibitory to the naturally occurring protox activity in the plant. Plants encompassed by the invention especially include those that would be potential targets for protox inhibiting herbicides, particularly agronomically important crops such as maize and other cereal crops such as barley, wheat, sorghum, rye, oats, turf and forage grasses, millet and rice. Also comprised are other crop plants such as sugar cane, soybean, cotton, sugar beet, oilseed rape and tobacco.

The present invention is directed further to methods for the production of plants, including plant material, such as for example plant tissues, protoplasts, cells, calli, organs, plant seeds, embryos, pollen, egg cells, zygotes, together with any other propagating material and plant parts, such as for example flowers, stems, fruits, leaves, roots originating in transgenic plants or their progeny previously transformed by means of the process of the invention, which produce an inhibitor-resistant form of the plant protox enzyme provided herein. Such plants may be stably transformed with a structural gene encoding the resistant protox, or prepared by direct selection techniques whereby herbicide resistant lines are isolated, characterized and developed. Furthermore, the present invention encompasses using plastid transformation technology to express protox genes within the plant chloroplast.

The present invention is further directed to probes and methods for detecting the presence of genes encoding inhibitor-resistant forms of the plant protox enzyme and quantitating levels of inhibitor-resistant protox transcripts in plant tissue. These methods may be used to identify or screen for plants or plant tissue containing and/or expressing a gene encoding an inhibitor-resistant form of the plant protox enzyme.

DESCRIPTION OF THE SEQUENCE LISTING

SEQ ID NO:1: DNA coding sequence for an *Arabidopsis thaliana* protox-1 protein.
SEQ ID NO:2: Arabidopsis protox-1 amino acid sequence encoded by SEQ ID NO:1.
SEQ ID NO:3: DNA coding sequence for an *Arabidopsis thaliana* protox-2 protein.
SEQ ID NO:4: Arabidopsis protox-2 amino acid sequence encoded by SEQ ID NO:3.
SEQ ID NO:5: DNA coding sequence for a maize protox-1 protein.
SEQ ID NO:6: Maize protox-1 amino acid sequence encoded by SEQ ID NO:5.
SEQ ID NO:7: DNA coding sequence for a maize protox-2 protein.
SEQ ID NO:8: Maize protox-2 amino acid sequence encoded by SEQ ID NO:7.
SEQ ID NO:9: DNA coding sequence for a wheat protox-1 protein.
SEQ ID NO:10: Wheat protox-1 amino acid sequence encoded by SEQ ID NO:9.
SEQ ID NO:11: DNA coding sequence for a soybean protox-1 protein.
SEQ ID NO:12: Soybean protox-1 protein encoded by SEQ ID NO:11.
SEQ ID NO:13: Promoter sequence from *Arabidopsis thaliana* protox-1 gene.
SEQ ID NO:14: Promoter sequence from maize protox-1 gene.
SEQ ID NO:15: DNA coding sequence for a cotton protox-1 protein.
SEQ ID NO:16: Cotton protox-1 amino acid sequence encoded by SEQ ID NO:15.
SEQ ID NO:17: DNA coding sequence for a sugar beet protox-1 protein.
SEQ ID NO:18: Sugar beet protox-1 amino acid sequence encoded by SEQ ID NO:17.
SEQ ID NO:19: DNA coding sequence for a rape protox-1 protein.
SEQ ID NO:20: Rape protox-1 amino acid sequence encoded by SEQ ID NO:19.
SEQ ID NO:21: DNA coding sequence for a rice protox-1 protein.
SEQ ID NO:22: Rice protox-1 amino acid sequence encoded by SEQ ID NO:21.

SEQ ID NO:23: DNA coding sequence for a sorghum protox-1 protein.
SEQ ID NO:24: Sorghum protox-1 amino acid sequence encoded by SEQ ID NO:23.
SEQ ID NO:25: Maize protox-1 intron sequence.
SEQ ID NO:26: Promoter sequence from sugar beet protox-1 gene.
SEQ ID NO:27: PcIp_P1a—plastid clpP gene promoter top strand PCR primer.
SEQ ID NO:28: PcIp_P1b—plastid clpP gene promoter bottom strand PCR primer.
SEQ ID NO:29: PcIp_P2b—plastid clpP gene promoter bottom strand PCR primer.
SEQ ID NO:30: Trps16_P1a—plastid rps 16 gene top strand PCR primer.
SEQ ID NO:31: Trps16_p1b—plastid rps 16 gene bottom strand PCR primer.
SEQ ID NO:32: minpsb_U—plastid psbA gene top strand primer.
SEQ ID NO:33: minpsb_L—plastid psbA gene bottom strand primer.
SEQ ID NO:34: APRTXP1a—top strand PCR primer.
SEQ ID NO:35: APRTXP1b—bottom strand PCR primer.

DEPOSITS

The following vector molecules have been deposited with Agricultural Research Service, Patent Culture Collection (NRRL), Northern Regional Research Center, 1815 North University Street, Peoria, Ill. 61604, U.S.A on the dates indicated below:

Wheat Protox-1a, in the pBluescript SK vector, was deposited Mar. 19, 1996, as pWDC-13 (NRRL #B21545).

Soybean Protox-1, in the pBluescript SK vector, was deposited Dec. 15, 1995 as pWDC-12 (NRRL #B-21516).

Cotton Protox-1, in the pBluescript SK vector, was deposited Jul. 1, 1996 as pWDC-15 (NRRL #B-21594).

Sugar beet Protox-1, in the pBluescript SK vector, was deposited Jul. 29, 1996, as pWDC-16 (NRRL #B-21595N).

Rape Protox-1, in the pBluescript SK vector, was deposited Aug. 23, 1996, as pWDC-17 (NRRL #B-21615).

Rice Protox-1, in the pBluescript SK vector, was deposited Dec. 6, 1996, as pWDC-18 (NRRL #B-21648).

Sorghum Protox-1, in the pBluescript SK vector, was deposited Dec. 6, 1996, as pWDC-19 (NRRL #B-21649).

Resistant mutant pAraC-2Cys, in the pMut-1 plasmid, was deposited on Nov. 14, 1994 under the designation pWDC-7 with the Agricultural Research Culture Collection and given the deposit designation NRRL #21339N.

AraPT1Pro containing the Arabidopsis Protox-1 promoter was deposited Dec. 15, 1995, as pWDC-11 (NRRL #B-21515)

A plasmid containing the maize Protox-1 promoter fused to the remainder of the maize Protox-1 coding sequence was deposited Mar. 19, 1996 as pWDC-14 (NRRL #B-21546).

A plasmid containing the Sugar Beet Protox-1 promoter was deposited Dec. 6, 1996 as pWDC-20 (NRRL #B-21650).

DETAILED DESCRIPTION OF THE INVENTION

I. Plant Protox Coding Sequences

In one aspect, the present invention is directed to an isolated DNA molecule that encodes protoporphyrinogen oxidase (referred to herein as "protox"), the enzyme that catalyzes the oxidation of protoporphyrinogen IX to protoporphyrin IX, from wheat, soybean, cotton, sugar beet, rape, rice, and sorghum. The DNA coding sequence and corresponding amino acid sequence for a wheat protox enzyme are provided as SEQ ID NOs:9 and 10, respectively. The DNA coding sequence and corresponding amino acid sequence for a soybean protox enzyme are provided as SEQ ID NOs:11 and 12, respectively. The DNA coding sequence and corresponding amino acid sequence for a cotton protox enzyme are provided as SEQ ID NOs:15 and 16, respectively. The DNA coding sequence and corresponding amino acid sequence for a sugar beet protox enzyme are provided as SEQ ID NOs:17 and 18, respectively. The DNA coding sequence and corresponding amino acid sequence for a rape protox enzyme are provided as SEQ ID NOs:19 and 20, respectively. The DNA coding sequence and corresponding amino acid sequence for a rice protox enzyme are provided as SEQ ID NOs:21 and 22, respectively. The DNA coding sequence and corresponding amino acid sequence for a sorghum protox enzyme are provided as SEQ ID NOs:23 and 24, respectively.

The DNA coding sequences and corresponding amino acid sequences for protox enzymes from *Arabidopsis thaliana* and maize that have been previously isolated are reproduced herein as SEQ ID NOs:1–4 (Arabidopsis) and SEQ ID NOs:5–8 (maize).

The invention therefore primarily is directed to a DNA molecule encoding a protoporphyrinogen oxidase (protox) comprising a eukaryotic protox selected from the group consisting of a wheat protox enzyme, a soybean protox enzyme, a cotton protox enzyme, a sugar beet protox enzyme, a rape protox enzyme, a rice protox enzyme and a sorghum protox enzyme.

Preferred within the scope of the invention are isolated DNA molecules encoding the protoporphyrinogen oxidase (protox) enzyme from dicotyledonous plants, but especially from soybean plants, cotton plants, sugar beet plants and rape plants, such as those given in SEQ ID NOS: 11, 15, 17 and 19. More preferred are isolated DNA molecules encoding the protoporphyrinogen oxidase (protox) enzyme from soybean, such as given in SEQ ID NO:11, and sugar beet, such as given in SEQ ID NO:17.

Also preferred are isolated DNA molecules encoding the protoporphyrinogen oxidase (protox) enzyme from monocotyledonous plants, but especially from wheat plants, rice plants and sorghum plants, such as those given in SEQ ID NOS: 9, 21 and 23. More preferred are isolated DNA molecules encoding the protoporphyrinogen oxidase (protox) enzyme from wheat such as given in SEQ ID NO:9.

In another aspect, the present invention is directed to isolated DNA molecules encoding the protoporphyrinogen oxidase (protox) enzyme protein from a dicotyledonous plant, wherein said protein comprises the amino acid sequence selected from the group consisting of SEQ ID NOs: 12, 16, 18 and 20. Further comprised are isolated DNA molecules encoding the protoporphyrinogen oxidase (protox) enzyme protein from a monocotyledonous plant, wherein said protein comprises the amino acid sequence selected from the group consisting of SEQ ID NOs: 10, 22 and 24. More preferred is an isolated DNA molecule encoding the protoporphyrinogen oxidase (protox) enzyme wherein said protein comprises the amino acid sequence from wheat such as given in SEQ ID NO:10. More preferred is an isolated DNA molecule encoding the protoporphyrinogen oxidase (protox) enzyme wherein said protein comprises the amino acid sequence from soybean, such as given in SEQ ID NO:12 and sugar beet, such as given in SEQ ID NO:18.

Using the information provided by the present invention, the DNA coding sequence for the protoporphyrinogen oxidase (protox) enzyme from any eukaryotic organism may be obtained using standard methods.

In another aspect, the present invention is directed to an isolated DNA molecule that encodes a wheat protox enzyme and that has a nucleotide sequence that hybridizes to the nucleotide sequence of SEQ ID NO:9 under the following hybridization and wash conditions:

(a) hybridization in 7% sodium dodecyl sulfate (SDS), 0.5M NaPO4 pH 7.0, 1 mM EDTA at 50° C.; and (b) wash in 2×SSC, 1% SDS at 50° C.

In yet another aspect, the present invention is directed to an isolated DNA molecule that encodes a soybean protox enzyme and that has a nucleotide sequence that hybridizes to the nucleotide sequence of SEQ ID NO:11 under the following hybridization and wash conditions:

(a) hybridization in 7% sodium dodecyl sulfate (SDS), 0.5M NaPO4 pH 7.0, 1 mM EDTA at 50° C.; and (b) wash in 2×SSC, 1% SDS at 50° C.

In still another aspect, the present invention is directed to an isolated DNA molecule that encodes a cotton protox enzyme and that has a nucleotide sequence that hybridizes to the nucleotide sequence of SEQ ID NO:15 under the following hybridization and wash conditions:

(a) hybridization in 7% sodium dodecyl sulfate (SDS), 0.5M NaPO4 pH 7.0, 1 mM EDTA at 50° C.; and (b) wash in 2×SSC, 1% SDS at 50° C.

In another aspect, the present invention is directed to an isolated DNA molecule that encodes a sugar beet protox enzyme and that has a nucleotide sequence that hybridizes to the nucleotide sequence of SEQ ID NO:17 under the following hybridization and wash conditions:

(a) hybridization in 7% sodium dodecyl sulfate (SDS), 0.5M NaPO4 pH 7.0, 1 mM EDTA at 50° C.; and (b) wash in 2×SSC, 1% SDS at 50° C.

In another aspect, the present invention is directed to an isolated DNA molecule that encodes a rape protox enzyme and that has a nucleotide sequence that hybridizes to the nucleotide sequence of SEQ ID NO:19 under the following hybridization and wash conditions:

(a) hybridization in 7% sodium dodecyl sulfate (SDS), 0.5M NaPO4 pH 7.0, 1 mM EDTA at 50° C.; and (b) wash in 2×SSC, 1% SDS at 50° C.

In another aspect, the present invention is directed to an isolated DNA molecule that encodes a rice protox enzyme and that has a nucleotide sequence that hybridizes to the nucleotide sequence of SEQ ID NO:21 under the following hybridization and wash conditions:

(a) hybridization in 7% sodium dodecyl sulfate (SDS), 0.5M NaPO4 pH 7.0, 1 mM EDTA at 50° C.; and (b) wash in 2×SSC, 1% SDS at 50° C.

In another aspect, the present invention is directed to an isolated DNA molecule that encodes a sorghum protox enzyme and that has a nucleotide sequence that hybridizes to the nucleotide sequence of SEQ ID NO:23 under the following hybridization and wash conditions:

(a) hybridization in 7% sodium dodecyl sulfate (SDS), 0.5M NaPO4 pH 7.0, 1 mM EDTA at 50° C.; and (b) wash in 2×SSC, 1% SDS at 50° C.

The isolated eukaryotic protox sequences taught by the present invention may be manipulated according to standard genetic engineering techniques to suit any desired purpose. For example, the entire protox sequence or portions thereof may be used as probes capable of specifically hybridizing to protox coding sequences and messenger RNA's. To achieve specific hybridization under a variety of conditions, such probes include sequences that are unique among protox coding sequences and are preferably at least 10 nucleotides in length, and most preferably at least 20 nucleotides in length. Such probes may be used to amplify and analyze protox coding sequences from a chosen organism via the well known process of polymerase chain reaction (PCR). This technique may be useful to isolate additional protox coding sequences from a desired organism or as a diagnostic assay to determine the presence of protox coding sequences in an organism.

Factors that affect the stability of hybrids determine the stringency of the hybridization. One such factor is the melting temperature $T_m$, which can be easily calculated according to the formula provided in DNA PROBES, George H. Keller and Mark M. Manak, Macmillan Publishers Ltd, 1993, Section one: Molecular Hybridization Technology; page 8 ff. The preferred hybridization temperature is in the range of about 25° C. below the calculated melting temperature $T_m$ and preferably in the range of about 12–15° C. below the calculated melting temperature $T_m$ and in the case of oligonucleotides in the range of about 5–10° C. below the melting temperature $T_m$.

Comprised by the present invention are DNA molecules that hybridize to a DNA molecule according to the invention as defined hereinbefore, but preferably to an oligonucleotide probe obtainable from said DNA molecule comprising a contiguous portion of the sequence of the said protoporphyrinogen oxidase (protox) enzyme at least 10 nucleotides in length, under moderately stringent conditions.

The invention further embodies the use of a nucleotide probe capable of specifically hybridizing to a plant protox gene or mRNA of at least 10 nucleotides length in a polymerase chain reaction (PCR).

In a further embodiment, the present invention provides probes capable of specifically hybridizing to a eukaryotic DNA sequence encoding a protoporphyrinogen oxidase activity or to the respective mRNA and methods for detecting the said DNA sequences in eukaryotic organisms using the probes according to the invention.

Protox specific hybridization probes may also be used to map the location of the native eukaryotic protox gene(s) in the genome of a chosen organism using standard techniques based on the selective hybridization of the probe to genomic protox sequences. These techniques include, but are not limited to, identification of DNA polymorphisms identified or contained within the protox probe sequence, and use of such polymorphisms to follow segregation of the protox gene relative to other markers of known map position in a mapping population derived from self fertilization of a hybrid of two polymorphic parental lines (see e.g. Helentjaris et al., *Plant Mol. Biol.* 5: 109 (1985). Sommer et al. *Biotechniques* 12: 82 (1992); D'Ovidio et al., *Plant Mol. Biol.* 15: 169 (1990)). While any eukaryotic protox sequence is contemplated to be useful as a probe for mapping protox genes from any eukaryotic organism, preferred probes are those protox sequences from organisms more closely related to the chosen organism, and most preferred probes are those protox sequences from the chosen organism. Mapping of protox genes in this manner is contemplated to be particularly useful in plants for breeding purposes. For instance, by knowing the genetic map position of a mutant protox gene that confers herbicide resistance, flanking DNA markers can be identified from a reference genetic map (see, e.g., Helentjaris, *Trends Genet.* 3: 217 (1987)). During introgression of the herbicide resistance trait into a new breeding line, these markers can then be used to monitor the extent of protox-linked flanking chromosomal DNA still present in the recurrent parent after each round of back-crossing.

Protox specific hybridization probes may also be used to quantitate levels of protox mRNA in an organism using standard techniques such as Northern blot analysis. This technique may be useful as a diagnostic assay to detect altered levels of protox expression that may be associated with particular adverse conditions such as autosomal dominant disorder in humans characterized by both neuropsychiatric symptoms and skin lesions, which are associated with decreased levels of protox activity (Brenner and Bloomer, *New Engl. J. Med.* 302: 765 (1980)).

A further embodiment of the invention is a method of producing a DNA molecule comprising a DNA portion encoding a protein having protoporphyrinogen oxidase (protox) enzyme activity comprising:

(a) preparing a nucleotide probe capable of specifically hybridizing to a plant protox gene or mRNA, wherein said probe comprises a contiguous portion of the coding sequence for a protox protein from a plant of at least 10 nucleotides length;

(b) probing for other protox coding sequences in populations of cloned genomic DNA fragments or cDNA fragments from a chosen organism using the nucleotide probe prepared according to step (a); and (c) isolating and multiplying a DNA molecule comprising a DNA portion encoding a protein having protoporphyrinogen oxidase (protox) enzyme activity.

A further embodiment of the invention is a method of isolating a DNA molecule from any plant comprising a DNA portion encoding a protein having protoporphyrinogen oxidase (protox) enzyme activity.

(a) preparing a nucleotide probe capable of specifically hybridizing to a plant protox gene or mRNA, wherein said probe comprises a contiguous portion of the coding sequence for a protox protein from a plant of at least 10 nucleotides length;

(b) probing for other protox coding sequences in populations of cloned genomic DNA fragments or cDNA fragments from a chosen organism using the nucleotide probe prepared according to step (a); and (c) isolating a DNA molecule comprising a DNA portion encoding a protein having protoporphyrinogen oxidase (protox) enzyme activity.

The invention further comprises a method of producing an essentially pure DNA sequence coding for a protein exhibiting protoporphyrinogen oxidase (protox) enzyme activity, which method comprises:

(a) preparing a genomic or a cDNA library from a suitable source organism using an appropriate cloning vector;

(b) hybridizing the library with a probe molecule; and (c) identifying positive hybridizations of the probe to the DNA clones from the library that is clones potentially containing the nucleotide sequence corresponding to the amino acid sequence for protoporphyrinogen oxidase (protox).

The invention further comprises a method of producing an essentially pure DNA sequence coding for a protein exhibiting protoporphyrinogen oxidase (protox) enzyme activity, which method comprises:

(a) preparing total DNA from a genomic or a cDNA library;

(b) using the DNA of step (a) as a template for PCR reaction with primers representing low degeneracy portions of the amino acid sequence of protoporphyrinogen oxidase (protox).

A further object of the invention is an assay to identify inhibitors of protoporphyrinogen oxidase (protox) enzyme activity that comprises:

(a) incubating a first sample of protoporphyrinogen oxidase (protox) and its substrate;

(b) measuring an uninhibited reactivity of the protoporphyrinogen oxidase (protox) from step (a);

(c) incubating a first sample of protoporphyrinogen oxidase (protox) and its substrate in the presence of a second sample comprising an inhibitor compound;

(d) measuring an inhibited reactivity of the protoporphyrinogen oxidase (protox) enzyme from step (c); and (e) comparing the inhibited reactivity to the uninhibited reactivity of protoporphyrinogen oxidase (protox) enzyme.

A further object of the invention is an assay to identify inhibitor-resistant protoporphyrinogen oxidase (protox) mutants that comprises:

(a) incubating a first sample of protoporphyrinogen oxidase (protox) enzyme and its substrate in the presence of a second sample comprising a protoporphyrinogen oxidase (protox) enzyme inhibitor;

(b) measuring an unmutated reactivity of the protoporphyrinogen oxidase (protox) enzyme from step (a);

(c) incubating a first sample of a mutated protoporphyrinogen oxidase (protox) enzyme and its substrate in the presence of a second sample comprising protoporphyrinogen oxidase (protox) enzyme inhibitor;

(d) measuring a mutated reactivity of the mutated protoporphyrinogen oxidase (protox) enzyme from step (c); and (e) comparing the mutated reactivity to the unmutated reactivity of the protoporphyrinogen oxidase (protox) enzyme.

A further object of the invention is a protox enzyme inhibitor obtained by a method according to the invention.

For recombinant production of the enzyme in a host organism, the protox coding sequence may be inserted into an expression cassette designed for the chosen host and introduced into the host where it is recombinantly produced. The choice of specific regulatory sequences such as promoter, signal sequence, 5' and 3' untranslated sequences, and enhancer, is within the level of skill of the routineer in the art. The resultant molecule, containing the individual elements linked in proper reading frame, may be inserted into a vector capable of being transformed into the host cell. Suitable expression vectors and methods for recombinant production of proteins are well known for host organisms such as *E. coli* (see, e.g. Studier and Moffatt, *J. Mol. Biol.* 189: 113 (1986); Brosius, *DNA* 8: 759 (1989)), yeast (see, e.g., Schneider and Guarente, *Meth. Enzymol.* 194: 373 (1991)) and insect cells (see, e.g., Luckow and Summers, *Bio/Technol.* 6: 47 (1988)). Specific examples include plasmids such as pbluescript (Stratagene, La Jolla, Calif.), pFLAG (International Biotechnologies, Inc., New Haven, Conn.), pTrcHis (Invitrogen, La Jolla, Calif.), and baculovirus expression vectors, e.g., those derived from the genome of *Autographica caifornica* nuclear polyhedrosis virus (AcMNPV). A preferred baculovirus/insect system is pVI11392/Sf21 cells (Invitrogen, La Jolla, Calif.).

Recombinantly produced eukaryotic protox enzyme is useful for a variety of purposes. For example, it may be used to supply protox enzymatic activity in vitro. It may also be used in an in vitro assay to screen known herbicidal chemicals whose target has not been identified to determine if they inhibit protox. Such an in vitro assay may also be used as a more general screen to identify chemicals that inhibit protox activity and that are therefore herbicide candidates. Recombinantly produced eukaryotic protox enzyme may also be used in an assay to identify inhibitor-resistant protox mutants (see International application no. PCT/IB95/00452 filed Jun. 8, 1995, published Dec. 21, 1995 as WO 95/34659, incorporated by reference herein in its entirety). Alternatively, recombinantly produced protox enzyme may be used to further characterize its association with known inhibitors in order to rationally design new inhibitory herbicides as well as herbicide tolerant forms of the enzyme.

II. Inhibitor Resistant Plant Protox Enzymes

In another aspect, the present invention teaches modifications that can be made to the amino acid sequence of any plant protoporphyrinogen oxidase (referred to herein as "protox") enzyme to yield an inhibitor-resistant form of this enzyme. The present invention is directed to inhibitor-resistant plant protox enzymes having the modifications taught herein, and to DNA molecules encoding these modified enzymes, and to genes capable of expressing these modified enzymes in plants.

The present invention is thus directed to an isolated DNA molecule encoding a modified protoporphyrinogen oxidase (protox) having at least one amino acid modification, wherein said amino acid modification having the property of conferring resistance to a protox inhibitor, that is wherein said modified protox is tolerant to a herbicide in amounts that inhibit said eukaryotic protox. As used herein 'inhibit' refers to a reduction in enzymatic activity observed in the presence of a subject herbicide compared to the level of activity observed in the absence of the subject herbicide, wherein the percent level of reduction is preferably at least 10%, more preferably at least 50%, and most preferably at least 90%.

Preferred is a DNA molecule encoding a modified protoporphyrinogen oxidase (protox) comprising a eukaryotic protox selected from the group consisting of a wheat protox enzyme, a soybean protox enzyme, a cotton protox enzyme, a sugar beet protox enzyme, a rape protox enzyme, a rice protox enzyme and a sorghum protox enzyme having at least one amino acid modification, wherein said modified protox is tolerant to a herbicide in amounts that inhibit the naturally occurring protox activity.

Also preferred is a DNA molecule encoding a modified protoporphyrinogen oxidase (protox) comprising a plant protox wherein the cysteine occurring at the position corresponding to amino acid 159 of SEQ ID NO:6 is replaced with another amino acid, wherein said modified protox is tolerant to a herbicide in amounts that inhibit the naturally occurring protox activity. Particularly preferred is said DNA molecule wherein said cysteine is replaced with a phenylalanine or lysine, most preferred, wherein said cysteine is replaced with a phenylalanine.

Also preferred is a DNA encoding a modified protoporphyrinogen oxidase (protox) comprising a plant protox wherein the isoleucine occurring at the position corresponding to amino acid 419 of SEQ ID NO:6 is replaced with another amino acid, wherein said modified protox is tolerant to a herbicide in amounts that inhibit the naturally occurring protox activity. Particularly preferred is a DNA molecule, wherein said isoleucine is replaced with a threonine, histidine, glycine or asparagine most preferred, wherein said isoleucine is replaced with a threonine.

Also preferred is a DNA molecule encoding a modified protoporphyrinogen oxidase (protox) comprising a plant protox wherein the alanine occurring at the position corresponding to amino acid 164 of SEQ ID NO:6 is replaced with another amino acid, wherein said modified protox is tolerant to a herbicide in amounts that inhibit the naturally occurring protox activity. Partireplaced with a threonine, lelecule wherein said alanine is replaced with a threonine, leucine or valine.

Also preferred is a DNA molecule encoding a modified protoporphyrinogen oxidase (protox) comprising a plant protox wherein the glycine occurring at the position corresponding to amino acid 165 of SEQ ID NO:6 is replaced with another amino acid, wherein said modified protox is tolerant to a herbicide in amounts that inhibit the naturally occurring protox activity. Particularly preferred is a DNA molecule wherein said glycine is replaced with a serine or leucine.

Also preferred is a DNA molecule encoding a modified protoporphyrinogen oxidase (protox) comprising a plant protox wherein the tyrosine occurring at the position corresponding to amino acid 370 of SEQ ID NO:6 is replaced with another amino acid, wherein said modified protox is tolerant to a herbicide in amounts that inhibit the naturally occurring protox activity. Particularly preferred is a DNA molecule wherein said tyrosine is replaced with a isoleucine or methionine.

Also preferred is a DNA molecule encoding a modified protoporphyrinogen oxidase (protox) comprising a plant protox wherein the valine occurring at the position corresponding to amino acid 356 of SEQ ID NO:10 is replaced with another amino acid, wherein said modified protox is tolerant to a herbicide in amounts that inhibit the naturally occurring protox activity. Particularly preferred is a DNA molecule wherein said valine is replaced with a leucine.

Also preferred is a DNA molecule encoding a modified protoporphyrinogen oxidase (protox) comprising a plant protox wherein the serine occurring at the position corresponding to amino acid 421 of SEQ ID NO:10 is replaced with another amino acid, wherein said modified protox is tolerant to a herbicide in amounts that inhibit the naturally occurring protox activity. Particularly preferred is a DNA molecule wherein said serine is replaced with a proline.

Also preferred is a DNA molecule encoding a modified protoporphyrinogen oxidase (protox) comprising a plant protox wherein the valine occurring at the position corresponding to amino acid 502 of SEQ ID NO:10 is replaced with another amino acid, wherein said modified protox is tolerant to a herbicide in amounts that inhibit the naturally occurring protox activity. Particularly preferred is a DNA molecule wherein said valine is replaced with a alanine.

Also preferred is a DNA molecule encoding a modified protoporphyrinogen oxidase (protox) comprising a plant protox wherein the alanine occurring at the position corresponding to amino acid 211 of SEQ ID NO:10 is replaced with another amino acid, wherein said modified protox is tolerant to a herbicide in amounts that inhibit the naturally occurring protox activity. Particularly preferred is a DNA molecule wherein said alanine is replaced with a valine or threonine.

Also preferred is a DNA molecule encoding a modified protoporphyrinogen oxidase (protox) comprising a plant protox wherein the glycine occurring at the position corresponding to amino acid 212 of SEQ ID NO:10 is replaced with another amino acid, wherein said modified protox is tolerant to a herbicide in amounts that inhibit the naturally occurring protox activity. Particularly preferred is a DNA molecule wherein said glycine is replaced with a serine.

Also preferred is a DNA encoding a modified protoporphyrinogen oxidase (protox) comprising a plant protox wherein the isoleucine occurring at the position corresponding to amino acid 466 of SEQ ID NO:10 is replaced with another amino acid, wherein said modified protox is tolerant to a herbicide in amounts that inhibit the naturally occurring protox activity. Particularly preferred is a DNA molecule wherein said isoleucine is replaced with a threonine.

Also preferred is a DNA molecule encoding a modified protoporphyrinogen oxidase (protox) comprising a plant protox wherein the proline occurring at the position corresponding to amino acid 369 of SEQ ID NO:12 is replaced with another amino acid, wherein said modified protox is tolerant to a herbicide in amounts that inhibit the naturally occurring protox activity. Particularly preferred is a DNA molecule wherein said proline is replaced with a serine or histidine.

Also preferred is a DNA molecule encoding a modified protoporphyrinogen oxidase (protox) comprising a plant protox wherein the alanine occurring at the position corresponding to amino acid 226 of SEQ ID NO:12 is replaced with another amino acid, wherein said modified protox is tolerant to a herbicide in amounts that inhibit the naturally occurring protox activity. Particularly preferred is a DNA molecule, wherein said alanine is replaced with a threonine or leucine.

Also preferred is a DNA molecule encoding a modified protoporphyrinogen oxidase (protox) comprising a plant protox wherein the valine occurring at the position corresponding to amino acid 517 of SEQ ID NO:12 is replaced with another amino acid, wherein said modified protox is tolerant to a herbicide in amounts that inhibit the naturally occurring protox activity. Particularly preferred is a DNA molecule wherein said valine is replaced with a alanine.

Also preferred is a DNA molecule encoding a modified protoporphyrinogen oxidase (protox) comprising a plant protox wherein the tyrosine occurring at the position corresponding to amino acid 432 of SEQ ID NO:12 is replaced with another amino acid, wherein said modified protox is tolerant to a herbicide in amounts that inhibit the naturally occurring protox activity. Particularly preferred is a DNA molecule wherein said tyrosine is replaced with a leucine or isoleucine.

Also preferred is a DNA molecule encoding a modified protoporphyrinogen oxidase (protox) comprising a plant protox wherein the proline occurring at the position corresponding to amino acid 365 of SEQ ID NO:16 is replaced with another amino acid, wherein said modified protox is tolerant to a herbicide in amounts that inhibit the naturally occurring protox activity. Particularly preferred is a DNA molecule wherein said proline is replaced with a serine.

Also preferred is a DNA molecule encoding a modified protoporphyrinogen oxidase (protox) comprising a plant protox wherein the tyrosine occurring at the position corresponding to amino acid 428 of SEQ ID NO:16 is replaced with another amino acid, wherein said modified protox is tolerant to a herbicide in amounts that inhibit the naturally occurring protox activity. Particularly preferred is a DNA molecule wherein said tyrosine is replaced with a cysteine or arginine.

Also preferred is a DNA encoding a modified protoporphyrinogen oxidase (protox) comprising a plant protox wherein the tyrosine occurring at the position corresponding to amino acid 449 of SEQ ID NO:18 is replaced with another amino acid, wherein said modified protox is tolerant to a herbicide in amounts that inhibit the naturally occurring protox activity. Particularly preferred is a DNA molecule wherein said tyrosine is replaced with a cysteine, leucine, isoleucine, valine or methionine.

The present invention is further directed to a DNA molecule encoding a modified protoporphyrinogen oxidase (protox) comprising a plant protox having a first amino acid substitution and a second amino acid substitution; said first amino acid substitution having the property of conferring resistance to a protox inhibitor; and said second amino acid substitution having the property of enhancing said resistance conferred by said first amino acid substitution. Preferred is a DNA molecule encoding a modified protoporphyrinogen oxidase (protox) comprising a plant protox, wherein said plant is selected from the group consisting of maize, wheat, soybean, cotton, sugar beet, rape, rice, sorghum and Arabidopsis. More preferred is a DNA molecule encoding a modified protoporphyrinogen oxidase (protox) comprising a plant protox, wherein said plant is selected from the group consisting of maize, wheat, soybean, sugar beet, and Arabidopsis.

Preferred is a DNA molecule wherein said second amino acid substitution occurs at a position selected from the group consisting of:

(i) the position corresponding to the serine at amino acid 305 of SEQ ID NO:2;

(ii) the position corresponding to the threonine at amino acid 249 of SEQ ID NO:2;

(iii) the position corresponding to the proline at amino acid 118 of SEQ ID NO:2;

(iv) the position corresponding to the asparagine at amino acid 425 of SEQ ID NO:2; and (v) the position corresponding to the tyrosine at amino acid 498 of SEQ ID NO:2.

Also preferred is a DNA molecule wherein said first amino acid substitution occurs at a position selected from the group consisting of:

(a) the position corresponding to the alanine at amino acid 164 of SEQ ID NO:6;

(b) the position corresponding to the glycine at amino acid 165 of SEQ ID NO:6;

(c) the position corresponding to the tyrosine at amino acid 370 of SEQ ID NO:6;

(d) the position corresponding to the cysteine at amino acid 159 of SEQ ID NO:6;

(e) the position corresponding to the isoleucine at amino acid 419 of SEQ ID NO:6.

(f) the position corresponding to the valine at amino acid 356 of SEQ ID NO:10;

(g) the position corresponding to the serine at amino acid 421 of SEQ ID NO:10;

(h) the position corresponding to the valine at amino acid 502 of SEQ ID NO:10;

(i) the position corresponding to the alanine at amino acid 211 of SEQ ID NO:10;

(k) the position corresponding to the glycine at amino acid 212 of SEQ ID NO:10;

(l) the position corresponding to the isoleucine at amino acid 466 of SEQ ID NO:10;

(m) the position corresponding to the proline at amino acid 369 of SEQ ID NO:12;

(n) the position corresponding to the alanine at amino acid 226 of SEQ ID NO:12;

(o) the position corresponding to the tyrosine at amino acid 432 of SEQ ID NO:12;

(p) the position corresponding to the valine at amino acid 517 of SEQ ID NO:12;

(q) the position corresponding to the tyrosine at amino acid 428 of SEQ ID NO:16;
(r) the position corresponding to the proline at amino acid 365 of SEQ ID NO:16; and
(s) the position corresponding to the tyrosine at amino acid 449 of SEQ ID NO:18.

Particularly preferred is a DNA molecule encoding a modified protoporphyrinogen oxidase (protox) comprising a plant protox wherein said plant protox comprises an amino acid sequence selected from the group consisting of SEQ ID NOs:2, 4, 6, 8, 10, 12, 16, 18, 20 and 22. Most preferred is a DNA molecule encoding a modified protoporphyrinogen oxidase (protox) comprising a plant protox, wherein said plant protox comprises an amino acid sequence selected from the group consisting of SEQ ID NOs:2, 4, 6, 8, 10, 12, and 18.

More preferred is a DNA molecule, wherein said first amino acid substitution occurs at a position selected from the group consisting of
(a) the position corresponding to the alanine at amino acid 164 of SEQ ID NO:6;
(b) the position corresponding to the glycine at amino acid 165 of SEQ ID NO:6;
(c) the position corresponding to the tyrosine at amino acid 370 of SEQ ID NO:6;
(d) the position corresponding to the cysteine at amino acid 159 of SEQ ID NO:6;
(e) the position corresponding to the isoleucine at amino acid 419 of SEQ ID NO:6.

More preferred is a DNA molecule wherein said second amino acid substitution occurs at the position corresponding to the serine at amino acid 305 of SEQ ID NO:2 and said first amino acid substitution occurs at a position selected from the group consisting of
(a) the position corresponding to the alanine at amino acid 164 of SEQ ID NO:6;
(b) the position corresponding to the tyrosine at amino acid 370 of SEQ ID NO:6.

Particularly preferred is a DNA molecule wherein said serine occurring at the position corresponding to amino acid 305 of SEQ ID NO:2 is replaced with leucine.

More preferred is a DNA molecule wherein said second amino acid substitution occurs at the position corresponding to the threonine at amino acid 249 of SEQ ID NO:2 and said first amino acid substitution occurs at a position selected from the group consisting of
(a) the position corresponding to the alanine at amino acid 164 of SEQ ID NO:6; and
(b) the position corresponding to the tyrosine at amino acid 370 of SEQ ID NO:6.

Particularly preferred is a DNA wherein said threonine occurring at the position corresponding to amino acid 249 of SEQ ID NO:2 is replaced with an amino acid selected from the group consisting of isoleucine and alanine.

More preferred is a DNA molecule wherein said second amino acid substitution occurs at the position corresponding to the proline at amino acid 118 of SEQ ID NO:2 and said first amino acid substitution occurs at a position selected from the group consisting of
(a) the position corresponding to the alanine at amino acid 164 of SEQ ID NO:6; and
(b) the position corresponding to the tyrosine at amino acid 370 of SEQ ID NO:6.

Particularly preferred is a DNA molecule wherein said proline occurring at the position corresponding to amino acid 118 of SEQ ID NO:2 is replaced with a leucine.

More preferred is a DNA molecule wherein said second amino acid substitution occurs at the position corresponding to the asparagine at amino acid 425 of SEQ ID NO:2 and said first amino acid substitution occurs at a position selected from the group consisting of
(a) the position corresponding to the alanine at amino acid 164 of SEQ ID NO:6; and
(b) the position corresponding to the tyrosine at amino acid 370 of SEQ ID NO:6.

Particularly preferred is a DNA molecule wherein said asparagine occurring at the position corresponding to amino acid 425 of SEQ ID NO:2 is replaced with a serine.

More preferred is a DNA molecule wherein said second amino acid substitution occurs the position corresponding to the tyrosine at amino acid 498 of SEQ ID NO:2 and said first amino acid substitution occurs at a position selected from the group consisting of
(a) the position corresponding to the alanine at amino acid 164 of SEQ ID NO:6; and
(b) the position corresponding to the tyrosine at amino acid 370 of SEQ ID NO:6.

Particularly preferred is a DNA molecule wherein said tyrosine occurring at the position corresponding to amino acid 498 of SEQ ID NO:2 is replaced with a cysteine.

More preferred is a DNA molecule wherein said tyrosine occurring at the position corresponding to amino acid 370 of SEQ ID NO:6 is replaced with an amino acid selected from the group consisting of cysteine, isoleucine, leucine, threonine, valine and methionine.

Particularly preferred is a DNA molecule wherein said tyrosine occurring at the position corresponding to amino acid 370 of SEQ ID NO:6 is replaced with an amino acid selected from the group consisting of cysteine, isoleucine, leucine, threonine and methionine.

More preferred is a DNA molecule wherein said alanine occurring at the position corresponding to residue 164 of SEQ ID NO:6 is replaced with an amino acid selected from the group consisting of valine, threonine, leucine, cysteine and tyrosine.

More preferred is a DNA molecule wherein said glycine occurring at the position corresponding to residue 165 of SEQ ID NO:6 is replaced with an amino acid selected from the group consisting of serine and leucin.

Particularly preferred is a DNA molecule wherein said glycine occurring at the position corresponding to residue 165 of SEQ ID NO:6 is replaced with a serine.

More preferred is a DNA molecule wherein said cysteine occurring at the position corresponding to residue 159 of SEQ ID NO:6 is replaced with an amino acid selected from the group consisting of phenylalanine and lysine.

Particularly preferred is a DNA molecule wherein said cysteine occurring at the position corresponding to residue 159 of SEQ ID NO:6 is replaced with a phenylalanine.

More preferred is a DNA molecule wherein said isoleucine occurring at the position corresponding to residue 419 of SEQ ID NO:6 is replaced with an amino acid selected from the group consisting of threonine, histidine, glycine and asparagine.

Particularly preferred is a DNA molecule wherein said isoleucine occurring at the position corresponding to residue 419 of SEQ ID NO:6 is replaced with a threonine.

More preferred is a DNA molecule wherein said valine occurring at the position corresponding to residue 356 of SEQ ID NO:10 is replaced with a leucine.

More preferred is a DNA molecule wherein said serine occurring at the position corresponding to residue 421 of SEQ ID NO:10 is replaced with a proline.

More preferred is a DNA molecule wherein said valine occurring at the position corresponding to residue 502 of SEQ ID NO:10 is replaced with a alanine.

More preferred is a DNA molecule wherein said isoleucine occurring at the position corresponding to residue 466 of SEQ ID NO:10 is replaced with a threonine.

More preferred is a DNA molecule wherein said glycine occurring at the position corresponding to residue 212 of SEQ ID NO:10 is replaced with a serine.

More preferred is a DNA molecule wherein said alanine occurring at the position corresponding to residue 211 of SEQ ID NO:10 is replaced with a valine or threonine.

More preferred is a DNA molecule wherein said proline occurring at the position corresponding to residue 369 of SEQ ID NO:12 is replaced with a serine or a histidine.

More preferred is a DNA molecule wherein said alanine occurring at the position corresponding to residue 226 of SEQ ID NO:12 is replaced with a leucine or threonine.

More preferred is a DNA molecule wherein said tyrosine occurring at the position corresponding to residue 432 of SEQ ID NO:12 is replaced with a leucine or isoleucine.

More preferred is a DNA molecule wherein said valine occurring at the position corresponding to residue 517 of SEQ ID NO:12 is replaced with a alanine.

More preferred is a DNA molecule wherein said tyrosine occurring at the position corresponding to residue 428 of SEQ ID NO:16 is replaced with cysteine or arginine.

More preferred is a DNA molecule wherein said proline occurring at the position corresponding to residue 365 of SEQ ID NO:16 is replaced with serine.

More preferred is a DNA molecule wherein said proline occurring at the position corresponding to residue 449 of SEQ ID NO:18 is replaced with an amino acid selected from the group consisting of leucine, isoleucine, valine and methionine.

The present invention is directed to expression cassettes and recombinant vectors comprising said expression cassettes comprising essentially a promoter, but especially a promoter that is active in a plant, operably linked to a DNA molecule encoding the protoporphyrinogen oxidase (protox) enzyme from a eukaryotic organism according to the invention. The expression cassette according to the invention may in addition further comprise a signal sequence operably linked to said DNA molecule, wherein said signal sequence is capable of targeting the protein encoded by said DNA molecule into the chloroplast or the mitochondria.

The invention relates to a chimeric gene, which comprises an expression cassette comprising essentially a promoter, but especially a promoter that is active in a plant, operably linked to a heterologous DNA molecule encoding a protoporphyrinogen oxidase (protox) enzyme from a eukaryotic organism according to the invention. Preferred is a chimeric gene, wherein the DNA molecule encodes an protoporphyrinogen oxidase (protox) enzyme from a plant selected from the group consisting of Arabidopsis, sugar cane, soybean, barley, cotton, tobacco, sugar beet, oilseed rape, maize, wheat, sorghum, rye, oats, turf and forage grasses, millet, forage and rice. More preferred is a chimeric gene, wherein the DNA molecule encodes an protoporphyrinogen oxidase (protox) enzyme from a plant selected from the group consisting of soybean, cotton, tobacco, sugar beet, oilseed rape, maize, wheat, sorghum, rye, oats, turf grass, and rice. Particularly preferred is a chimeric gene, wherein the DNA molecule encodes an protoporphyrinogen oxidase (protox) enzyme from a plant selected from the group consisting of wheat, soybean, cotton, sugar beet, rape, rice and sorghum. Most preferred is a chimeric gene, wherein the DNA molecule encodes an protoporphyrinogen oxidase (protox) enzyme from a plant selected from the group consisting of soybean, sugar beet, and wheat.

More preferred is a chimeric gene comprising a promoter active in a plant operably linked to a heterologous DNA molecule encoding a protoporphyrinogen oxidase (protox) selected from the group consisting of a wheat protox comprising the sequence set forth in SEQ ID NO:10, a soybean protox comprising the sequence set forth in SEQ ID NO:12, cotton protox comprising the sequence set forth in SEQ ID NO:16, a sugar beet protox comprising the sequence set forth in SEQ ID NO:18, a rape protox comprising the sequence set forth in SEQ ID NO:20, a rice protox comprising the sequence set forth in SEQ ID NO:22 and a sorghum protox comprising the sequence set forth in SEQ ID NO:24. More preferred is a chimeric gene, wherein the protoporphyrinogen oxidase (protox) is selected from the group consisting of a wheat protox comprising the sequence set forth in SEQ ID NO:10, a soybean protox comprising the sequence set forth in SEQ ID NO:12, and a sugar beet protox comprising the sequence set forth in SEQ ID NO:18.

As used herein 'protox-1' refers to a chloroplast protox whereas 'protox-2' refers to a mitochondrial protox.

Particularly preferred is a chimeric gene, wherein the DNA molecule encodes a protein from an Arabidopsis species having protox-1 activity or protox-2 activity, preferably wherein said protein comprises the amino acid sequence set forth in SEQ ID NO:2 or SEQ ID NO:4.

Particularly preferred is a chimeric gene, wherein the DNA molecule encodes a protein from maize having protox-1 activity or protox-2 activity, preferably wherein said protein comprises the amino acid sequence set forth in set forth in SEQ ID NO:6 or SEQ ID NO:8.

Particularly preferred is a chimeric gene, wherein the DNA molecule encodes a protein from wheat having protox-1 activity preferably wherein said protein comprises the amino acid sequence set forth in SEQ ID NO:10.

Particularly preferred is a chimeric gene, wherein the DNA molecule encodes a protein from soybean having protox-1 activity, preferably wherein said protein comprises the amino acid sequence set forth in SEQ ID NO:12.

Particularly preferred is a chimeric gene, wherein the DNA molecule encodes a protein from cotton having protox-1 activity, preferably wherein said protein comprises the amino acid sequence set forth in SEQ ID NO:16.

Particularly preferred is a chimeric gene, wherein the DNA molecule encodes a protein from sugar beet having protox-1 activity, preferably wherein said protein comprises the amino acid sequence set forth in SEQ ID NO:18.

Particularly preferred is a chimeric gene, wherein the DNA molecule encodes a protein from rape having protox-1 activity, preferably wherein said protein comprises the amino acid sequence set forth in SEQ ID NO:20.

Particularly preferred is a chimeric gene, wherein the DNA molecule encodes a protein from rice having protox-1 activity, preferably wherein said protein comprises the amino acid sequence set forth in SEQ ID NO:22.

Particularly preferred is a chimeric gene, wherein the DNA molecule encodes a protein from sorghum having protox-1 activity, preferably wherein said protein comprises the amino acid sequence set forth in SEQ ID NO:24.

The invention also embodies a chimeric gene, which comprises an expression cassette comprising essentially a promoter, but especially a promoter that is active in a plant, operably linked to the DNA molecule encoding an protoporphyrinogen oxidase (protox) enzyme from a eukaryotic organism according to the invention, which is resistant to herbicides at levels that inhibit the corresponding unmodified version of the enzyme. Preferred is a chimeric gene, wherein the DNA molecule encodes an protoporphyrinogen oxidase (protox) enzyme from a plant selected from the group consisting of Arabidopsis, sugar cane, soybean, barley, cotton, tobacco, sugar beet, oilseed rape, maize, wheat, sorghum, rye, oats, turf and forage grasses, millet, forage and rice. More preferred is a chimeric gene, wherein the DNA molecule encodes an protoporphyrinogen oxidase (protox) enzyme from a plant selected from the group consisting of soybean, cotton, tobacco, sugar beet, oilseed rape, maize, wheat, sorghum, rye, oats, turf grass, and rice. Particularly preferred is a chimeric gene, wherein the DNA molecule encodes an protoporphyrinogen oxidase (protox) enzyme from a plant selected from the group consisting of Arabidopsis, soybean, cotton, sugar beet, oilseed rape, maize, wheat, sorghum, and rice.

Encompassed by the present invention is a chimeric gene comprising a promoter that is active in a plant operably linked to the DNA molecule encoding a modified protoporphyrinogen oxidase (protox) comprising a eukaryotic protox having at least one amino acid modification, wherein said amino acid modification having the property of conferring resistance to a protox inhibitor.

Also encompassed by the present invention is a chimeric gene comprising a promoter that is active in a plant operably linked to the DNA molecule encoding a modified protoporphyrinogen oxidase (protox) comprising a plant protox having a first amino acid substitution and a second amino acid substitution; said first amino acid substitution having the property of conferring resistance to a protox inhibitor; and said second amino acid substitution having the property of enhancing said resistance conferred by said first amino acid substitution. Preferred is said chimeric gene additionally comprising a signal sequence operably linked to said DNA molecule, wherein said signal sequence is capable of targeting the protein encoded by said DNA molecule into the chloroplast or in the mitochondria.

The chimeric gene according to the invention may in addition further comprise a signal sequence operably linked to said DNA molecule, wherein said signal sequence is capable of targeting the protein encoded by said DNA molecule into the chloroplast. The chimeric gene according to the invention may in addition further comprise a signal sequence operably linked to said DNA molecule, wherein said signal sequence is capable of targeting the protein encoded by said DNA molecule into the mitochondria.

Also encompassed by the present invention is any of the DNA sequences mentioned herein before, which is stably integrated into a host genome.

The invention further relates to a recombinant DNA molecule comprising a plant protoporphyrinogen oxidase (protox) or a functionally equivalent derivative thereof.

The invention further relates to a recombinant DNA vector comprising said recombinant DNA molecule.

A further object of the invention is a recombinant vector comprising the chimeric gene according to the invention, wherein said vector is capable of being stably transformed into a host cell.

A further object of the invention is a recombinant vector comprising the chimeric gene according to the invention, wherein said vector is capable of being stably transformed into a plant, plant seeds, plant tissue or plant cell. Preferred is a recombinant vector comprising the chimeric gene according to the invention, wherein said vector is capable of being stably transformed into a plant. The plant, plant seeds, plant tissue or plant cell stably transformed with the vector is capable of expressing the DNA molecule encoding a protoporphyrinogen oxidase (protox). Preferred is a recombinant vector, wherein the plant, plant seeds, plant tissue or plant cell stably transformed with the said vector is capable of expressing the DNA molecule encoding a protoporphyrinogen oxidase (protox) from a plant that is resistant to herbicides at levels that inhibit the corresponding unmodified version of the enzyme.

Preferred is a recombinant vector comprising the chimeric gene comprising a promoter active in a plant operably linked to a heterologous DNA molecule encoding a protoporphyrinogen oxidase (protox) selected from the group consisting of a wheat protox comprising the sequence set forth in SEQ ID NO:10, a soybean protox comprising the sequence set forth in SEQ ID NO:12, cotton protox comprising the sequence set forth in SEQ ID NO:16, a sugar beet protox comprising the sequence set forth in SEQ ID NO:18, a rape protox comprising the sequence set forth in SEQ ID NO:20, a rice protox comprising the sequence set forth in SEQ ID NO:22 and a sorghum protox comprising the sequence set forth in SEQ ID NO:24, wherein said vector is capable of being stably transformed into a host cell.

Also preferred is recombinant vector comprising the chimeric gene comprising a promoter that is active in a plant operably linked to the DNA molecule encoding a modified protoporphyrinogen oxidase (protox) comprising a plant protox having a first amino acid substitution and a second amino acid substitution; said first amino acid substitution having the property of conferring resistance to a protox inhibitor; and said second amino acid substitution having the property of enhancing said resistance conferred by said first amino acid substitution, wherein said vector is capable of being stably transformed into a plant cell.

Also encompassed by the present invention is a host cell stably transformed with the vector according to the invention, wherein said host cell is capable of expressing said DNA molecule. Preferred is a host cell selected from the group consisting of a plant cell, a bacterial cell, a yeast cell, and an insect cell.

The present invention is further directed to plants and the progeny thereof, plant tissue and plant seeds tolerant to herbicides that inhibit the naturally occurring protox activity in these plants, wherein the tolerance is conferred by a gene expressing a modified inhibitor-resistant protox enzyme as taught herein. Representative plants include any plants to which these herbicides may be applied for their normally intended purpose. Preferred are agronomically important crops, i.e., angiosperms and gymnosperms such as Arabidopsis, sugar cane, soybean, barley, cotton, tobacco, sugar beet, oilseed rape, maize, wheat, sorghum, rye, oats, turf and forage grasses, millet, forage and rice and the like. More preferred are agronomically important crops, i.e., angiosperms and gymnosperms such as Arabidopsis, cotton, soybean, rape, sugar beet, maize, rice, wheat, barley, oats, rye, sorghum, millet, turf, forage, turf grasses. Particularly preferred are agronomically important crops, i.e., angiosperms and gymnosperms such as Arabidopsis, soybean, cotton, sugar beet, oilseed rape, maize, wheat, sorghum, and rice.

Preferred is a plant comprising the DNA molecule encoding a modified protoporphyrinogen oxidase (protox) comprising a plant protox having a first amino acid substitution and a second amino acid substitution; said first amino acid substitution having the property of conferring resistance to a protox inhibitor; and said second amino acid substitution having the property of enhancing said resistance conferred by said first amino acid substitution, wherein said DNA molecule is expressed in said plant and confers upon said plant tolerance to a herbicide in amounts that inhibit naturally occurring protox activity. Preferred is a plant, wherein said DNA molecule replaces a corresponding naturally occurring protox coding sequence. Comprised by the present invention is a plant and the progeny thereof comprising the chimeric gene according to the invention, wherein said chimeric gene confers upon said plant tolerance to a herbicide in amounts that inhibit naturally occurring protox activity.

Encompassed by the present invention are transgenic plant tissue, including plants and the progeny thereof, seeds, and cultured tissue, stably transformed with at least one chimeric gene according to the invention. Preferred is transgenic plant tissue, including plants, seeds, and cultured tissue, stably transformed with at least one chimeric gene that comprises an expression cassette comprising essentially a promoter, but especially a promoter that is active in a plant, operably linked to the DNA molecule encoding an protoporphyrinogen oxidase (protox) enzyme that is resistant to herbicides at levels that inhibit the corresponding unmodified version of the enzyme in the plant tissue.

The recombinant DNA molecules of the invention can be introduced into the plant cell in a number of art-recognized ways. Those skilled in the art will appreciate that the choice of method might depend on the type of plant, i.e. monocot or dicot, targeted for transformation. Suitable methods of transforming plant cells include microinjection (Crossway et al., *BioTechniques* 4: 320–334 (1986)), electroporation (Riggs et al, *Proc. Natl. Acad. Sci. USA* 83: 5602–5606 (1986), Agrobacterium mediated transformation (Hinchee et al., *Biotechnology* 6: 915–921 (1988)), direct gene transfer (Paszkowski et al., *EMBO J.* 3: 2717–2722 (1984)), ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., *Biotechnology* 6: 923–926 (1988)), and protoplast transformation/regeneration methods (see U.S. Pat. No. 5,350,689 issued Sep. 27, 1994 to Ciba-Geigy Corp.). Also see, Weissinger et al., *Annual Rev. Genet.* 22: 421–477 (1988); Sanford et al., *Particulate Science and Technology* 5: 27–37 (1987)(onion); Christou et al., *Plant Physiol.* 87: 671–674 (1988)(soybean); McCabe et al., *Bio/Technology* 6: 923–926 (1988)(soybean); Datta et al., *Bio/Technology* 8: 736–740 (1990)(rice); Klein et al., *Proc. Natl. Acad. Sci. USA,* 85: 4305–4309 (1988)(maize); Klein et al., *Bio/Technotogy* 6: 559–563 (1988)(maize); Klein et al., *Plant Physiol.* 91: 440–444 (1988)(maize); Fromm et al., *Bio/Technology* 8: 833–839 (1990); and Gordon-Kamm et al., *Plant Cell* 2: 603–618 (1990) (maize).

Comprised within the scope of the present invention are transgenic plants, in particular transgenic fertile plants transformed by means of the aforedescribed processes and their asexual and/or sexual progeny, which still are resistant or at least tolerant to inhibition by a herbicide at levels that normally are inhibitory to the naturally occurring protox activity in the plant. Progeny plants also include plants with a different genetic background than the parent plant, which plants result from a backcrossing program and still comprise in their genome the herbicide resistance trait according to the invention. Very especially preferred are hybrid plants that are resistant or at least tolerant to inhibition by a herbicide at levels that normally are inhibitory to the naturally occurring protox activity in the plant.

The transgenic plant according to the invention may be a dicotyledonous or a monocotyledonous plant. Preferred are monocotyledonous plants of the Graminaceae family involving Lolium, Zea, Triticum, Triticale, Sorghum, Saccharum, Bromus, Orvzae, Avena, Hordeum, Secale and Setaria plants. More preferred are transgenic maize, wheat, barley, sorghum, rye, oats, turf and forage grasses, millet and rice. Especially preferred are maize, wheat, sorghum, rye, oats, turf grasses and rice.

Among the dicotyledonous plants Arabidopsis, soybean, cotton, sugar beet, sugar cane, oilseed rape, tobacco and sunflower are more preferred herein. Especially preferred are soybean, cotton, tobacco, sugar beet and oilseed rape.

The expression 'progeny' is understood to embrace both, "asexually" and "sexually" generated progeny of transgenic plants. This definition is also meant to include all mutants and variants obtainable by means of known processes, such as for example cell fusion or mutant selection and that still exhibit the characteristic properties of the initial transformed plant, together with all crossing and fusion products of the transformed plant material. This also includes progeny plants that result from a backcrossing program, as long as the said progeny plants still contain the herbicide resistant trait according to the invention.

Another object of the invention concerns the proliferation material of transgenic plants. The proliferation material of transgenic plants is defined relative to the invention as any plant material that may be propagated sexually or asexually in vivo or in vitro. Particularly preferred within the scope of the present invention are protoplasts, cells, calli, tissues, organs, seeds, embryos, pollen, egg cells, zygotes, together with any other propagating material obtained from transgenic plants.

Parts of plants, such as for example flowers, stems, fruits, leaves, roots originating in transgenic plants or their progeny previously transformed by means of the process of the invention and therefore consisting at least in part of transgenic cells, are also an object of the present invention.

A further object of the invention is a method of producing plants, protoplasts, cells, calli, tissues, organs, seeds, embryos, pollen, egg cells, zygotes, together with any other propagating material, parts of plants, such as for example flowers, stems, fruits, leaves, roots originating in transgenic plants or their progeny previously transformed by means of the process of the invention, which therefore produce an inhibitor resistant form of a plant protox enzyme by transforming the plant, plant parts with the DNA according to the invention. Preferred is a method of producing a host cell comprising an isolated DNA molecule encoding a protein from a eukaryote having protoporphyrinogen oxidase (protox) activity comprising transforming the said host cell with a recombinant vector molecule according to the invention. Further preferred is a method of producing a plant cell comprising an isolated DNA molecule encoding a protein from a eukaryote having protoporphyrinogen oxidase (protox) activity comprising transforming the said plant cell with a recombinant vector molecule according to the invention. Preferred is a method of producing transgenic progeny of a transgenic parent plant comprising an isolated DNA molecule encoding a protein from a eukaryote having protoporphyrinogen oxidase (protox) activity comprising transforming the said parent plant with a recombinant vector molecule according to the invention and transferring the herbicide tolerant trait to the progeny of the said transgenic parent plant involving known plant breeding techniques.

Preferred is a method for the production of plants, plant tissues, plant seeds and plant parts, which produce an inhibitor-resistant form of the plant protox enzyme, wherein the plants, plant tissues, plant seeds and plant parts have been stably transformed with a structural gene encoding the resistant protox enzyme. Particularly preferred is a method for the production of plants, plant tissues, plant seeds and plant parts, wherein the plants, plant tissues, plant seeds and plant parts have been stably transformed with the DNA according to the invention. Especially preferred is a method for the production of said plants, plant tissues, plant seeds and plant parts, which produce an inhibitor-resistant form of the plant protox enzyme, wherein the plants, plant tissues, plant seeds and plant parts have been prepared by direct selection techniques whereby herbicide resistant lines are isolated, characterized and developed.

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding that aims at the development of plants with improved properties such as tolerance of pests, herbicide tolerance, or stress tolerance, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines that for example increase the effectiveness of conventional methods such as herbicide or pesticide treatment or allow to dispense with said methods due to their modified genetic properties. Alternatively new crops with improved stress tolerance can be obtained that, due to their optimized genetic "equipment", yield harvested product of better quality than products that were not able to tolerate comparable adverse developmental conditions.

In seeds production germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides or mixtures thereof. Customarily used protectant coatings comprise compounds such as captan, carboxin, thiram (TMTD®), methalaxyl (Apron®), and pirimiphos-methyl (Actellic®). If desired these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is thus a further object of the present invention to provide plant propagation material for cultivated plants, but especially plant seed that is treated with an seed protectant coating customarily used in seed treatment.

It is a further aspect of the present invention to provide new agricultural methods such as the methods exemplified above, which are characterized by the use of transgenic plants, transgenic plant material, or transgenic seed according to the present invention. Comprised by the present invention is an agricultural method, wherein a transgenic plant or the progeny thereof is used comprising a chimeric gene according to the invention in an amount sufficient to express herbicide resistant forms of herbicide target proteins in a plant to confer tolerance to the herbicide.

To breed progeny from plants transformed according to the method of the present invention, a method such as that which follows may be used: maize plants produced as described in the examples set forth below are grown in pots in a greenhouse or in soil, as is known in the art, and permitted to flower. Pollen is obtained from the mature tassel and used to pollinate the ears of the same plant, sibling plants, or any desirable maize plant. Similarly, the ear developing on the transformed plant may be pollinated by pollen obtained from the same plant, sibling plants, or any desirable maize plant. Transformed progeny obtained by this method may be distinguished from non-transformed progeny by the presence of the introduced gene(s) and/or accompanying DNA (genotype), or the phenotype conferred. The transformed progeny may similarly be selfed or crossed to other plants, as is normally done with any plant carrying a desirable trait. Similarly, tobacco or other transformed plants produced by this method may be selfed or crossed as is known in the art in order to produce progeny with desired characteristics. Similarly, other transgenic organisms produced by a combination of the methods known in the art and this invention may be bred as is known in the art in order to produce progeny with desired characteristics.

The modified inhibitor-resistant protox enzymes of the invention have at least one amino acid substitution, addition or deletion relative to their naturally occurring counterpart (i.e. inhibitor-sensitive forms that occur naturally in a plant without being manipulated, either directly via recombinant DNA methodology or indirectly via selective breeding, etc., by man). Amino acid positions that may be modified to yield an inhibitor-resistant form of the protox enzyme, or enhance inhibitor resistance, are indicated in bold type in Table 1 in the context of plant protox-1 sequences from Arabidopsis, maize, soybean, cotton, sugar beet, rape, rice, sorghum and wheat. The skilled artisan will appreciate that equivalent changes may be made to any plant protox gene having a structure sufficiently similar to the protox enzyme sequences shown herein to allow alignment and identification of those amino acids that are modified according to the invention to generate inhibitor-resistant forms of the enzyme. Such additional plant protox genes may be obtained using standard techniques as described in International application no. PCT/IB95/00452 filed Jun. 8, 1995, published Dec. 21, 1995 as WO 95/34659 whose relevant parts are herein incorporated by reference.

DNA molecules encoding the herbicide resistant protox coding sequences taught herein may be genetically engineered for optimal expression in a crop plant. This may include altering the coding sequence of the resistance allele for optimal expression in the crop species of interest. Methods for modifying coding sequences to achieve optimal expression in a particular crop species are well known (see, e.g. Perlak et al., *Proc. Natl. Acad. Sci. USA* 88: 3324 (1991); Koziel et al., *Bio/technol.* 11: 194 (1993)).

Genetically engineering a protox coding sequence for optimal expression may also include operably linking the appropriate regulatory sequences (i.e. promoter, signal sequence, transcriptional terminators). Examples of promoters capable of functioning in plants or plant cells (i.e., those capable of driving expression of the associated structural genes such as protox in plant cells) include the cauliflower mosaic virus (CaMV) 19S or 35S promoters and CaMV double promoters; nopaline synthase promoters; pathogenesis-related (PR) protein promoters; small subunit of ribulose bisphosphate carboxylase (ssuRUBISCO) promoters, heat shock protein promoter from Brassica with reference to EPA 0 559 603 (hsp80 promoter), Arabidopsis actin promoter and the SuperMas promoter with reference to WO 95/14098 and the like. Preferred promoters will be those that confer high level constitutive expression or, more preferably, those that confer specific high level expression in the tissues susceptible to damage by the herbicide. Preferred promoters are the rice actin promoter (McElroy et al., *Mol. Gen. Genet.* 231: 150 (1991)), maize ubiquitin promoter (EP 0 342 926; Taylor et al., *Plant Cell Rep.* 12: 491 (1993)), and the PR-1 promoter from tobacco, Arabidopsis, or maize (see U.S. patent application Ser. Nos. EP-332 104 and 08/181, 271 to Ryals et al., incorporated by reference herein in their entirety). The promoters themselves may be modified to manipulate promoter strength to increase protox expression, in accordance with art-recognized procedures.

The inventors have also discovered that another preferred promoter for use with the inhibitor-resistant protox coding sequences is the promoter associated with the native protox gene (i.e. the protox promoter; see copending, co-owned U.S. patent application Ser. No. 08/802,323 entitled "Promoters from Protoporphyrinogen Oxidase Genes", filed on the same day as the present application and incorporated by reference herein in its entirety.) The promoter sequence from an Arabidopsis protox-1 gene is set forth in SEQ ID NO:13, the promoter sequence from a maize protox-1 gene is set forth in SEQ ID NO:14, and the promoter sequence from a sugar beet protox-1 gene is set forth in SEQ ID NO:26.

Since the protox promoter itself is suitable for expression of inhibitor-resistant protox coding sequences, the modifications taught herein may be made directly on the native protox gene present in the plant cell genome without the need to construct a chimeric gene with heterologous regulatory sequences. Such modifications can be made via directed mutagenesis techniques such as homologous recombination and selected for based on the resulting herbicide-resistance phenotype (see, e.g. Example 10, Pazkowski et al., *EMBO J.* 7: 4021–4026 (1988), and U.S. Pat. No. 5,487,992, particularly columns 18–19 and Example 8). An added advantage of this approach is that besides containing the native protox promoter, the resulting modified gene will also include any other regulatory elements, such as signal or transit peptide coding sequences, which are part of the native gene.

Signal or transit peptides may be fused to the protox coding sequence in chimeric DNA constructs of the invention to direct transport of the expressed protox enzyme to the desired site of action. Examples of signal peptides include those natively linked to the plant pathogenesis-related proteins, e.g. PR-1, PR-2, and the like. See, e.g., Payne et al., *Plant Mol. Biol.* 11: 89–94 (1988). Examples of transit peptides include the chloroplast transit peptides such as those described in Von Heijne et al, *Plant Mol. Biol. Rep.* 9: 104–126 (1991); Mazur et al., *Plant Physiol.* 85: 1110 (1987); Vorst et al., *Gene* 65: 59 (1988), and mitochondrial transit peptides such as those described in Boutry et al., *Nature* 328: 340–342 (1987). Chloroplast and mitochondrial transit peptides are contemplated to be particularly useful with the present invention as protox enzymatic activity typically occurs within the mitochondria and chloroplast. Most preferred for use are chloroplast transit peptides as inhibition of the protox enzymatic activity in the chloroplasts is contemplated to be the primary basis for the action of protox-inhibiting herbicides (Witkowski and Hailing, *Plant Physiol.* 87: 632 (1988); Lehnen et al., *Pestic. Biochem. Physiol.* 37:239 (1990); Duke et al., *Weed Sci.* 39: 465 (1991)). Also included are sequences that result in localization of the encoded protein to various cellular compartments such as the vacuole. See, for example, Neuhaus et al., *Proc. Natl. Acad. Sci. USA* 88: 10362–10366 (1991) and Chrispeels, *Ann. Rev. Plant Physiol. Plant Mol. Biol.* 42:21–53 (1991). The relevant disclosures of these publications are incorporated herein by reference in their entirety.

Chimeric DNA construct(s) of the invention may contain multiple copies of a promoter or multiple copies of the protox structural genes. In addition, the construct(s) may include coding sequences for markers and coding sequences for other peptides such as signal or transit peptides, each in proper reading frame with the other functional elements in the DNA molecule. The preparation of such constructs are within the ordinary level of skill in the art.

Useful markers include peptides providing herbicide, antibiotic or drug resistance, such as, for example, resistance to hygromycin, kanamycin, G418, gentamycin, lincomycin, methotrexate, glyphosate, phosphinothricin, or the like. These markers can be used to select cells transformed with the chimeric DNA constructs of the invention from untransformed cells. Other useful markers are peptidic enzymes that can be easily detected by a visible reaction, for example a color reaction, for example luciferase, β-glucuronidase, or β-galactosidase.

The method of positive selection of genetically transformed cells into which a desired nucleotide sequence can be incorporated by providing the transformed cells with a selective advantage is herein incorporated by reference as WO 94/20627.

Plastid expression, in which genes are inserted by homologous recombination into all of the several thousand copies of the circular plastid genome present in each plant cell, takes advantage of the enormous copy number advantage over nuclear-expressed genes to permit expression levels that may exceed 10% of the total soluble plant protein. In addition, plastid expression is desirable because plastid-encoded traits are not pollen transmissable; hence, potential risks of inadvertent transgene escape to wild relatives of transgenic plants is obviated. Plastid transformation technology is extensively described in U.S. Pat. Nos. 5,451,513, 5,545,817, and 5,545,818, all of which are hereby expressly incorporated by reference in their entireties; in PCT application no. WO 95/16783, which is hereby incorporated by reference in its entirety; and in McBride et al., Proc. Natl. Acad. Sci. USA 91: 7301–7305 (1994), which is also hereby incorporated by reference in its entirety. The basic technique for tobacco chloroplast transformation was developed and refined in the laboratory of Dr. Pal Maliga at Rutgers University (Piscataway, N.J.) and involves the particle bombardment of leaf tissue with regions of cloned plastid DNA flanking a selectable antibiotic resistance marker. The 1 to 1.5 kb flanking regions, termed targeting sequences, facilitate homologous recombination with the plastid genome and thus allow the replacement or modification of specific regions of the 156 kb tobacco plastome. Initially, point mutations in the chloroplast 16S rRNA and rps12 genes conferring resistance to spectinomycin and/or streptomycin were utilized as selectable markers for transformation (Svab, Z., Hajdukiewicz, P., and Maliga, P. (1990) Proc. Natl. Acad. Sci. USA 87, 8526–8530, hereby incorporated by reference; Staub, J. M., and Maliga, P. (1992) Plant Cell 4, 39–45, hereby incorporated by reference). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P., *EMBO J.* 12: 601–606 (1993), hereby incorporated by reference). Substantial increases in transformation frequency were obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) Proc. Natl. Acad. Sci. USA 90, 913–917, hereby incorporated by reference). Previously, this marker had been used successfully for high-frequency transformation of the plastid genome of the green alga Chlamydomonas reinhardtii (Goldschmidt-Clermont, M. (1991) Nucl. Acids Res. 19, 4083–4089, hereby incorporated by reference).

Therefore, the present invention further encompasses a chimeric gene comprising a plant plastid promoter operably linked to an isolated DNA molecule that either encodes a native plant protox enzyme or a modified plant protox enzyme, such as a DNA molecule that encodes a native or modified wheat, soybean, cotton, sugar beet, rape, rice, or sorghum protox enzyme. An especially preferred plant plastid promoter is a c/pP gene promoter. The chimeric gene preferably further comprises a 5' untranslated sequence (5'UTR) from the plastid promoter and a plastid gene 3' untranslated sequence (3' UTR) operably linked to the isolated DNA molecule. Preferably, the 3' UTR is a plastid rps16 gene 3' untranslated sequence.

The present invention also encompasses a plastid transformation vector comprising the chimeric gene described immediately above, as well as a plant plastid transformed with such a plastid transformation vector, wherein said modified plant protox enzyme is expressed in said plant plastid. The invention also encompasses a plant or plant cell, including the progeny thereof, comprising this plant plastid, wherein a modified plant protox enzyme is expressed in the plant and confers upon the plant tolerance to a herbicide in amounts that inhibit naturally occurring protox activity.

Where a herbicide resistant protox allele is obtained via directed mutation of the native gene in a crop plant or plant cell culture from which a crop plant can be regenerated, it may be moved into commercial varieties using traditional breeding techniques to develop a herbicide tolerant crop without the need for genetically engineering the modified coding sequence and transforming it into the plant. Alternatively, the herbicide resistant gene may be isolated, genetically engineered for optimal expression and then transformed into the desired variety.

Genes encoding altered protox resistant to a protox inhibitor can also be used as selectable markers in plant cell transformation methods. For example, plants, plant tissue or plant cells transformed with a transgene can also be transformed with a gene encoding an altered protox capable of being expressed by the plant. The thus-transformed cells are transferred to medium containing the protox inhibitor wherein only the transformed cells will survive. Protox inhibitors contemplated to be particularly useful as selective agents are the diphenylethers {e.g. acifluorfen, 5-[2-chloro-4-(trifluoromethyl)phenoxy]-2-nitrobezoic acid; its methyl ester; or oxyfluorfen, 2-chloro-1-(3-ethoxy-4-nitrophenoxy)-4-(trifluorobenzene)}, oxidiazoles, (e.g. oxidiazon, 3-[2,4-dichloro-5-(1-methylethoxy)phenyl]-5-(1, 1-dimethylethyl)-1,3,4-oxadiazol-2-(3H-one), cyclic imides (e.g. S-23142, N-(4-chloro-2-fluoro-5-proparglyoxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-[1-(2,3,4-trichlorophenyl)-4-nitropyrazolyl-5-oxy] propionate; M&B 39279), pyridine derivatives (e.g. LS 82-556), and phenopylate and its O-phenylpyrrolidino- and piperidinocarbamate analogs and bicyclic Triazolones as disclosed in the International patent application WO 92/04827; EP 532146).

The method is applicable to any plant cell capable of being transformed with an altered protox-encoding gene, and can be used with any transgene of interest. Expression of the transgene and the protox gene can be driven by the same promoter functional on plant cells, or by separate promoters.

Modified inhibitor-resistant protox enzymes of the present invention are resistant to herbicides that inhibit the naturally occurring protox activity. The herbicides that inhibit protox include many different structural classes of molecules (Duke et al., *Weed Sci.* 39: 465 (1991); Nandihalli et al., *Pesticide Biochem. Physiol.* 43: 193 (1992); Matringe et al., *FEBS Lett.* 245: 35 (1989); Yanase and Andoh, *Pesticide Biochem. Physiol.* 35: 70 (1989)), including the diphenylethers {e.g. acifluorifen, 5-[2-chloro-4-(trifluoromethyl)phenoxy]-2-nitrobezoic acid; its methyl ester; or oxyfluorfen, 2-chloro-1-(3-ethoxy-4-nitrophenoxy)-4-(trifluorbenzene)}, oxidiazoles (e.g. oxidiazon, 3-[2,4-dichloro-5-(1-methylethoxy)phenyl]-5-(1, 1-dimethylethyl)-1,3,4-oxadiazol-2-(3H-one), cyclic imides (e.g. S-23142, N-(4-chloro-2-fluoro-5-propargyloxyphenyl)-3,4,5,6-tetrahydrophthalimide; chlorophthalim, N-( 4-chlorophenyl)-3,4,5,6-tetrahydrophthalimide), phenyl pyrazoles (e.g. TNPP-ethyl, ethyl 2-[1-(2,3,4-trichlorophenyl)-4-nitropyrazolyl-5-oxy] propionate; M&B 39279), pyridine derivatives (e.g. LS 82-556), and phenopylate and its O-phenylpyrrolidino- and piperidinocarbamate analogs.

The diphenylethers of particular significance are those having the general formula

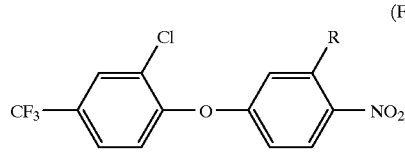
(Formula I)

wherein R equals —COONa (Formula II), —CONHSO$_2$CH$_3$ (Formula III) or —COOCH$_2$COOC$_2$H$_5$ (Formula IV; see Maigrot et al., *Brighton Crop Protection Conference-Weeds:* 47–51 (1989)).

Additional diphenylethers of interest are those where R equals:

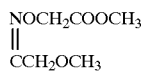

(Formula IVa; see Hayashi et al., *Brighton Crop Protection Conference-Weeds:* 53–58 (1989)).

An additional diphenylether of interest is one having the formula:

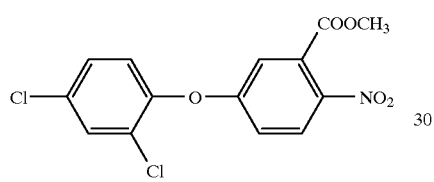

(Formula IVb; bifenox, see Dest et al., *Proc. Northeast Weed Sci. Conf.* 27: 31 (1973)).

A further diphenylether of interest is one having the formula:

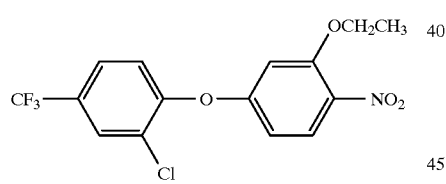

(Formula IVc; oxyfluorfen; see Yih and Swithenbank, *J. Agric. Food Chem.*, 23: 592 (1975))

Yet another diphenylether of interest is one having the formula:

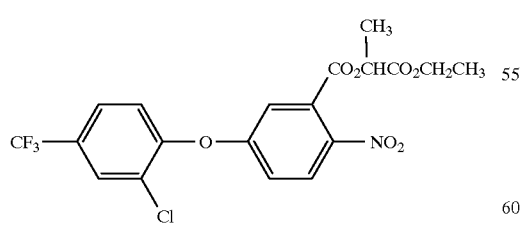

(Formula IVd; lactofen, see page 623 of "The Pesticide Manual", 10$^{th}$ ed., ed. by C. Tomlin, British Crop Protection Council, Surrey (1994))

Also of significance are the class of herbicides known as imides, having the general formula

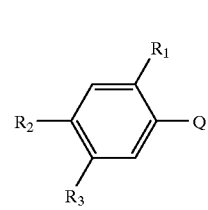
(Formula V)

wherein Q equals

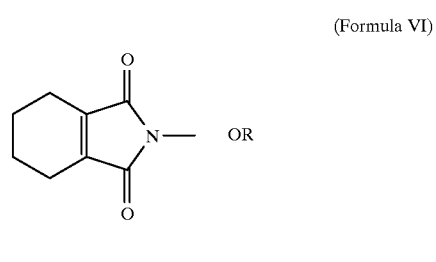
(Formula VI)

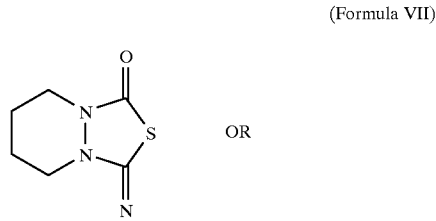
(Formula VII)

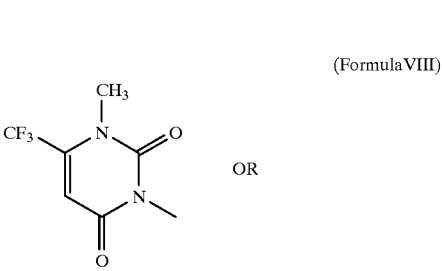
(Formula VIII)

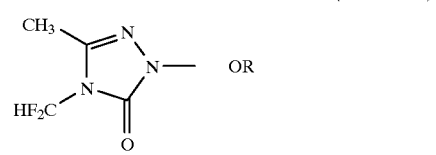
(Formula IX)

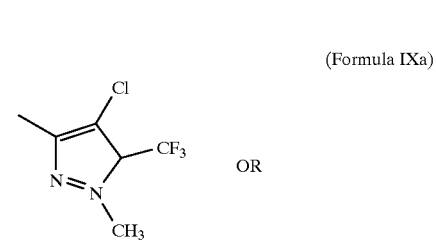
(Formula IXa)

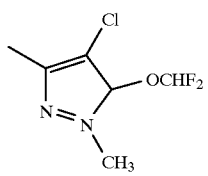

(Formula IXb)

(see Hemper et al. (1995) in "Proceedings of the Eighth International Congress of Pesticide Chemistry", Ragdale et al., eds., Amer. Chem. Soc, Washington, D.C., pp.42–48 (1994)); and $R_1$ equals H, Cl or F, $R_2$ equals Cl and $R_3$ is an optimally substituted ether, thioether, ester, amino or alkyl group. Alternatively, $R_2$ and $R_3$ together may form a 5 or 6 membered heterocyclic ring. Examples of imide herbicides of particular interest are

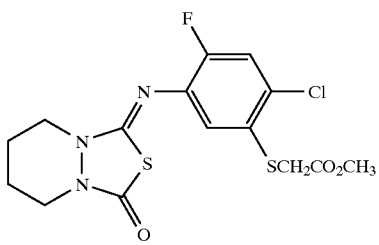

(Formula VIIa; fluthiacet-methyl, see Miyazawa et al., *Brighton Crop Protection Conference-Weeds*, pp. 23–28 (1993))

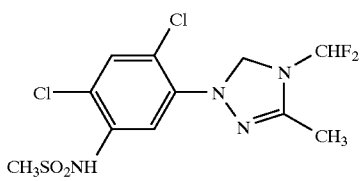

(Formula X sulfentrazone, see Van Saun et al., *Brighton Crop Protection Conference-Weeds*, pp. 77–82 (1991)).

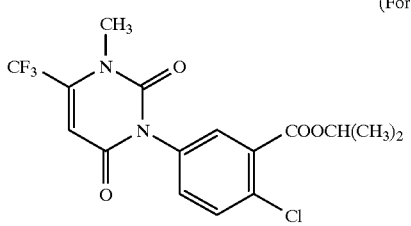

(Formula XI)

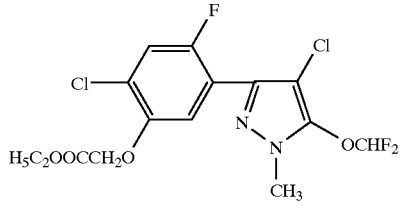

(Formula XII)

(see Miura et al., Brighton Crop Protection Conference-Weeds: 35-40 (1993))

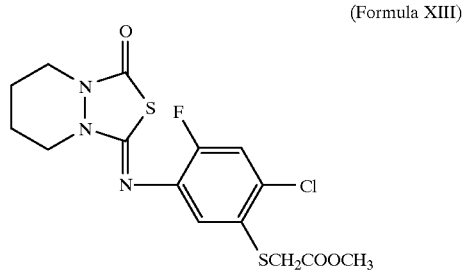

(Formula XIII)

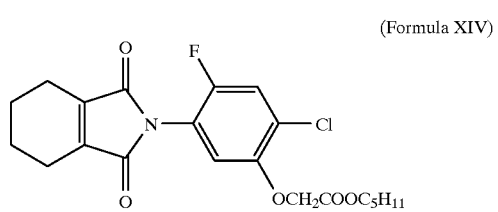

(Formula XIV)

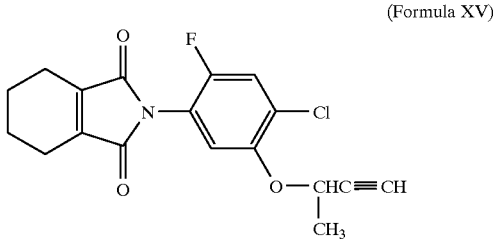

(Formula XV)

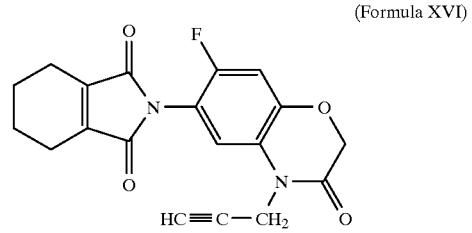

(Formula XVI)

The herbicidal activity of the above compounds is described in the *Proceedings of the* 1991 *Brighton Crop Protection Conference, Weeds* (British Crop Protection Council) (Formulae X and XVI), Proceedings of the 1993 *Brighton Crop Protection Conference, Weeds* (British Crop Protection Council) (Formulae XII and XIII), U.S. Pat. No. 4,746,352 (Formula XI) and *Abstracts of the Weed Science Society of America* vol. 33, pg. 9 (1993)(Formula XIV).

The most preferred imide herbicides are those classified as aryluracils and having the general formula

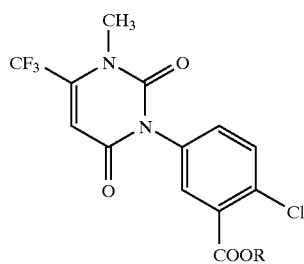

(Formula XVII)

wherein R signifies the group (C$_{2-6}$-alkenyloxy)carbonyl-C$_{1-4}$-alkyl, as disclosed in U.S. Pat. No. 5,183,492, herein incorporated by reference.

Also of significance are herbicides having the general formula:

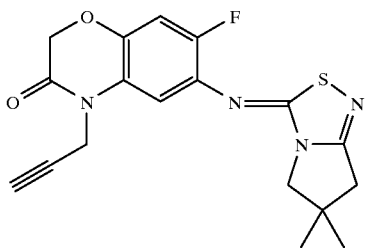

(Formula XVIII; thiadiazimin)
(see Weiler et al., Brighton Crop Protection Conference-Weeds, pp. 29-34 (1993));

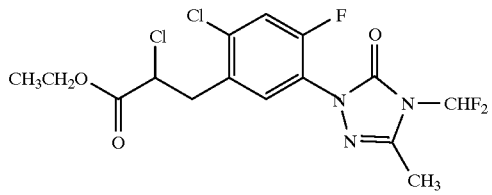

(Formula XIX; carfentrazone)
(see Van Saun et al., Brighton Crop Protection Conference-Weeds: pp. 19-22 (1993));

N-substituted pyrazoles of the general formula:

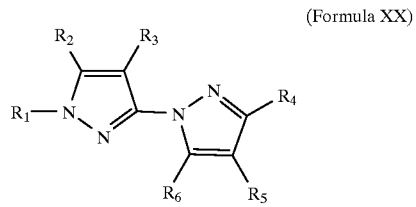

(Formula XX)

wherein

R$_1$ is C$_1$–C$_4$-alkyl, optionally substituted by one or more halogen atoms;

R$_2$ is hydrogen, or a C$_1$–C$_4$-alkoxy, each of which is optionally substituted by one or more halogen atoms, or R$_1$ and R$_2$ together from the group —(CH$_2$)$_n$—X—, where X is bound at R$_2$;

R$_3$ is hydrogen or halogen,

R$_4$ is hydrogen or C$_1$–C$_4$-alkyl,

R$_5$ is hydrogen, nitro, cyano or the group —COOR$_6$ or —CONR$_7$R$_8$, and

R$_6$ is hydrogen, C$_1$–C$_6$-alkyl, C$_2$–C$_6$-alkenyl or C$_2$–C$_6$-alkynyl;

(see international patent publications WO 94/08999, WO 93/10100, and U.S. Pat. No. 5,405,829 assigned to Schering);

N-phenylpyrazoles, such as:

(Formula XXI; nipyraclofen)
(see page 621 of "The Pesticide Manual", 9th ed., ed. by C.R. Worthing, British Crop Protection Council, Surrey (1991));

and 3-substituted-2-aryl-4,5,6,7-tetrahydroindazoles (Lyga et al. *Pesticide Sci.* 42:29–36 (1994)).

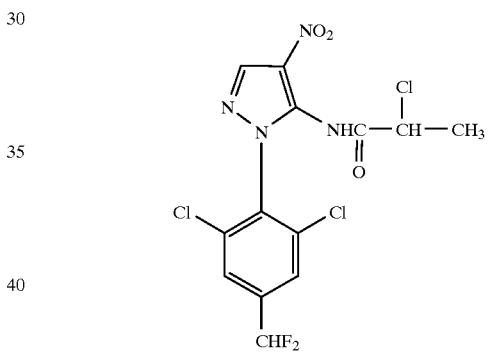

(Formula XXIa; BAY 11340)

Also of significance are phenylpyrazoles of the type described in WO 96/01254 and WO 97/00246, both of which are hereby incorporated by reference. (Formula XXII).

Levels of herbicide that normally are inhibitory to the activity of protox include application rates known in the art, and that depend partly on external factors such as environment, time and method of application. For example, in the case of the imide herbicides represented by Formulae V through IX, and more particularly those represented by Formulae X through XVII, the application rates range from 0.0001 to 10 kg/ha, preferably from 0.005 to 2 kg/ha. This dosage rate or concentration of herbicide may be different, depending on the desired action and particular compound used, and can be determined by methods known in the art.

A further object of the invention is a method for controlling the growth of undesired vegetation that comprises applying to a population of the plant selected from a group consisting of Arabidopsis, sugar cane, soybean, barley, cotton, tobacco, sugar beet, oilseed rape, maize, wheat, sorghum, rye, oats, turf and forage grasses, millet, forage and rice and the like an effective amount of a protox-inhibiting herbicide. Preferred is a method for controlling the growth of undesired vegetation, which comprises applying to a population of the selected from the group consisting of selected from the group consisting of soybean, cotton, tobacco, sugar beet, oilseed rape, maize, wheat, sorghum, rye, oats, turf grasses and rice an effective amount of a protox-inhibiting herbicide. Particularly preferred is a method for controlling the growth of undesired vegetation, which comprises applying to a population of the selected from the group consisting of Arabidopsis, soybean, cotton, sugar beet, oilseed rape, maize, wheat, sorghum, and rice.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by T. Maniatis, E. F. Fritsch and J. Sambrook, *Molecular Cloning: A Laboratory manual*, Cold Spring Harbor laboratory, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984).

Section A. Isolation And Characterization Of Plant Protoporphyrinogen Oxidase (Protox) Genes Example 1

Isolation of a Wheat Protox-1 cDNA Based on Sequence Homology to a Maize Protox-1 Coding Sequence Total RNA prepared from *Triticum aestivum* (cv Kanzler) was submitted to Clontech for custom cDNA library construction in the Lambda Uni-Zap vector. Approximately 50,000 pfu of the cDNA library were plated at a density of approximately 5,000 pfu per 10 cm Petri dish and duplicate filter lifts were made onto nitrocellulose membranes (Schleicher and Schuell). The plaque lifts were probed with the maize Protox-1 cDNA (SEQ ID NO:5; see Example 2 of International application no. PCT/IB95/00452, filed Jun. 8, 1995, published Dec. 21, 1995 as WO 95/34659) labeled with 32P-dCTP by the random priming method (Life Technologies). Hybridization conditions were 7% sodium dodecyl sulfate (SDS), 0.5M NaPO4 pH 7.0, 1 mM EDTA at 50° C. Wash conditions were 2×SSC, 1% SDS at 50° C. (Church and Gilbert, *Proc. Natl. Acad. Sci. USA* 81: 1991–1995 (1984), hereby incorporated by reference in its entirety.) Positively hybridizing plaques were purified and in vivo excised into pBluescript plasmids. The sequences of the cDNA inserts were determined by the chain termination method using dideoxy terminators labeled with fluorescent dyes (Applied Biosystems, Inc.). The longest wheat Protox-1 cDNA obtained from initial screening efforts, designated "wheat Protox-1", was 1489 bp in length. Wheat Protox-1 lacks coding sequence for the transit peptide plus approximately 126 amino acids of the mature coding sequence based on comparison with the other known plant protox peptide sequences.

A second screen was performed to obtain a longer wheat protox cDNA. For this screen, a *Triticum aestivum* (cv Kanzler) cDNA library was prepared internally using the lambda Uni-Zap vector. Approximately 200,000 pfu of the cDNA library was screened as indicated above, except that the wheat Protox-1 cDNA was used as a probe and hybridization and wash conditions were at 65° C. instead of 50° C. The longest wheat cDNA obtained from this screening effort, designated "wheat Protox-1a", was 1811 bp in length. The nucleotide sequence of this cDNA and the amino acid sequence it encodes are set forth in SEQ ID NOs:9 and 10, respectively. Based on comparison with the other known plant protox peptide sequences and with corresponding genomic sequence, this cDNA is either full-length or missing only a few transit peptide codons (Table 1). This wheat protein sequence is 91% identical (95% similar) to the maize Protox-1 protein sequence set forth in SEQ ID NO:6.

Wheat Protox-1a, in the pBluescript SK vector, was deposited Mar. 19, 1996, as pWDC-13 (NRRL #B21545).

Example 2

Isolation of a Soybean Protox-1 cDNA Based on Sequence Homology to an Arabidopsis Protox-1 Coding Sequence A Lambda Uni-Zap cDNA library prepared from soybean (v Williams 82, epicotyls) was purchased from Stratagene. Approximately 50,000 pfu of the library was plated at a density of approximately 5,000 pfu per 10 cm Petri dish and duplicate filter lifts were made onto Colony/Plaque Screen membranes (NEN Dupont). The plaque lifts were probed with the Arabidopsis Protox-1 cDNA (SEQ ID NO:1; see Example 1 of International application no. PCT/IB95/00452, filed Jun. 8, 1995, published Dec. 21, 1995 as WO 95/34659)) labeled with 32P-dCTP by the random priming method (Life Technologies). Hybridization conditions were 7% sodium dodecyl sulfate (SDS), 0.5M NaPO4 pH 7.0, 1 mM EDTA at 50° C. Wash conditions were 2×SSC, 1% SDS at 50° C. (Church and Gilbert (1984)). Positively hybridizing plaques were purified and in vivo excised into pBluescript plasmids. The sequence of the cDNA inserts was determined by the chain termination method using dideoxy terminators labeled with fluorescent dyes (Applied Biosystems, Inc.). The longest soybean cDNA obtained, designated "soybean Protox-1", is full-length based on comparison with the other known plant protox peptide sequences (Table 1). Soybean Protox-1 is 1847 bp in length and encodes a protein of 58.8 kDa. The nucleotide sequence of this cDNA and the amino acid sequence it encodes are set forth in SEQ ID NOs:11 and 12, respectively. The soybean protein is 78% identical (87% similar) to the Arabidopsis Protox-1 protein.

Soybean Protox-1, in the pBluescript SK vector, was deposited Dec. 15, 1995 as pWDC-12 (NRRL #B-21516).

An alignment of the predicted amino acid sequences of the respective proteins encoded by the sequences shown in SEQ ID NOS: 2, 6, 10, 12, 15, 17, 19, 21, 23 and are set forth in Table 1. An alignment of the predicted amino acid sequences of the respective proteins encoded by the sequences shown in SEQ ID NOS: 4 and 8 are set forth in Table 2.

TABLE 1

Comparison of Protox-1 Amino Acid Sequences from Arabidopsis ("Arabpt-1"; SEQ ID NO:2), Maize ("Mzpt-1"; SEQ ID NO:6), Wheat ("Wtpt-1"; SEQ ID NO:10), Soybean ("Soybeanpt-1"; SEQ ID NO:12), Cotton ("Cottonpt-1"; SEQ ID NO:16), Sugar beet ("Sugpt-1"; SEQ ID NO:18), Rape ("Rapet-1"; SEQ ID NO:20), Rice ("Ricept-1"; SEQ ID NO:22), and Sorghum ("Sorghumpt-1"; SEQ ID NO:24)

Alignment is performed using the PileUp program (GCG package, University of Wisconsin, Madison, WI). Positions that may be modified according to the teachings herein to confer or enhance inhibitor resistance are shown in bold type.

```
                 1                                                            50
     Rapept-1    ..........  ..........  MDLSLLRP..  QPFLSPFSNP  FPRSRPYKPL
     Arabpt-1    ..........  ..........  MELSLLRPTT  QSLLPSFSKP  NLRLNVYKPL
   Sorghumpt-1   ..........  ..........  ..........  ..........  ..........
        Mzpt-1   ..........  ..........  ..........  ..........  ..........
        Wtpt-1   ..........  ..........  .........M  ATATVAAASP  LRGRVTGRPH
      Ricept-1   ..........  ..........  ..........  ..........  ..........
    Cottonpt-1   ..........  ......MTAL  IDLSLLRSSP  SVSPFSIPHH  QHPPRFRKPF
    Soybeanpt1   ........MV  SVFNEILFPP  NQTLLRPSLH  SPTSFFTSPT  RKFPRSRPNP
       Sugpt-1   MKSMALSNCI  PQTQCMPLRS  SGHYRGNCIM  LSIPCSLIGR  RGYYSHKKRR 51                                                           100
     Rapept-1    NLRCSVSGGS  VVGSSTIEGG  GGGKTVTADC  VIVGGGISGL  CIAQALVTKH
     Arabpt-1    RLRCSVAGGP  TVGSSKIEGG  GGT.TITTDC  VIVGGGISGL  CIAQALATKH
   Sorghumpt-1   ..........  ..........  ..........  ..........  ..........
        Mzpt-1   ..........  ..........  .......ADC  VVVGGGISGL  CTAQALATRH
        Wtpt-1   RVRPRCATAS  SATETPAAPG  VRL...SAEC  VIVGAGISGL  CTAQALATRY
      Ricept-1   ..........  ..........  ..........  ..........  ..........
    Cottonpt-1   KLRCSLAEGP  TISSSKIDGG  ESS...IADC  VIVGGGISGL  CIAQALATKH
    Soybeanpt1   ILRCSIAEES  TASPPKTR..  DSA...PVDC  VVVGGGVSGL  CIAQALATKH
       Sugpt-1   MSMSCSTSSG  SKSAVKEAGS  GSGAGGLLDC  VIVGGGISGL  CIAQALCTKH 101                                                           150
     Rapept-1    PDA..AKNVM  VTEAKDRVGG  NIIT..REEQ  GFLWEEGPNS  FQPSDPMLTM
     Arabpt-1    PDA..APNLI  VTEAKDRVGG  NIIT..REEN  GFLWEEGPNS  FQPSDPMLTM
   Sorghumpt-1   ..........  ..........  ..STVERPEE  GYLWEEGPNS  FQPSDPVLSM
        Mzpt-1   ..G..VGDVL  VTEARARPGG  NITTVERPEE  GYLWEEGPNS  FQPSDPVLTM
        Wtpt-1   ..G..VSDLL  VTEARDRPGG  NITTVERPDE  GYLWEEGPNS  FQPSDPVLTM
      Ricept-1   ..........  ..........  ..........  ..........  ..........
    Cottonpt-1   RDV..ASNVI  VTEARDRVGG  NITTVER..D  GYLWEEGPNS  FQPSDPILTM
    Soybeanpt1   ..A..NANVV  VTEARDRVGG  NITTMER..D  GYLWEEGPNS  FQPSDPMLTM
       Sugpt-1   SSSSLSPNFI  VTEAKDRVGG  NIVTVE..AD  GYIWEEGPNS  FQPSDAVLTM 151                                                           200
     Rapept-1    VVDSGLKDDL  VLGDPTAPRF  VLWNGKLRPV  PSKLTDLPFF  DLMSIGGKIR
     Arabpt-1    VVDSGLKDDL  VLGDPTAPRF  VLWNGKLRPV  PSKLTDLPFF  DLMSIGGKIR
   Sorghumpt-1   AVDSGLKDDL  VFGDPNAPRF  VLWEGKLRPV  PSKPADLPFF  DLMSIPGKLR
        Mzpt-1   AVDSGLKDDL  VFGDPNAPRF  VLWEGKLRPV  PSKPADLPFF  DLMSIPGKLR
        Wtpt-1   AVDSGLKDDL  VFGDPNAPRF  VLWEGKLRPV  PSKPGDLPFF  SLMSIPGKLR
      Ricept-1   ..........  ..........  ..........  ..........  ..........
    Cottonpt-1   AVDSGLKDDL  VLGDPNAPRF  VLWEGKLRPV  PSKPTDLPFF  DLMSIAGKLR
    Soybeanpt1   VVDSGLKDEL  VLGDPDAPRF  VLWNRKLRPV  PGKLTDLPFF  DLMSIGGKIR
       Sugpt-1   AVDSGLKDEL  VLGDPNAPRF  VLWNDKLRPV  PSSLTDLPFF  DLMTIPGKIR 201                                                           250
     Rapept-1    AGFGAIGIRP  SPPGREESVE  EFVRRNLGDE  VFERLIEPFC  SGVYAGDPAK
     Arabpt-1    AGFGALGIRP  SPPGREESVE  EFVRRNLGDE  VFERLIEPFC  SGVYAGDPSK
   Sorghumpt-1   AGLGALGIRP  PAPGREESVE  EFVRRNLGAE  VFERLIEPFC  SGVYAGDPSK
        Mzpt-1   AGLGALGIRP  PPPGREESVE  EFVRRNLGAE  VFERLIEPFC  SGVYAGDPSK
        Wtpt-1   AGLGALGIRP  PPPGREESVE  EFVRRNLGAE  VFERLIEPFC  SGVYAGDPSK
      Ricept-1   ..........  ..........  ..........  ..........  ..........
    Cottonpt-1   AGFGAIGIRP  PPPGYEESVE  EFVRRNLGAE  VFERFIEPFC  SGVYAGDPSK
    Soybeanpt1   AGFGALGIRP  PPPGHEESVE  EFVRRNLGDE  VFERLIEPFC  SGVYAGDPSK
       Sugpt-1   AALGALGFRP  SPPHEESVE   HFVRRNLGDE  VFERLIEPFC  SGVYAGDPAK 251                                                           300
     Rapept-1    LSMKAAFGKV  WKLEENGGSI  IGGAFKAIQA  KNKAPKTTRD  PRLPKPKGQT
     Arabpt-1    LSMKAAFGKV  WKLEQNGGSI  IGGTFKAIQE  RKNAPKAERD  PRLPKPQGQT
   Sorghumpt-1   LSMKAAFGKV  WRLEEAGGSI  IGGTIKTIQE  RGKNPKPPRD  PRLPKPKGQT
        Mzpt-1   LSMKAAFGKV  WRLEETGGSI  IGGTIKTIQE  RSKNPKPPRD  ARLPKPKGQT
        Wtpt-1   LSMKAAFGKV  WRLEEIGGSI  IGGTIKAIQD  KGKNPKPPRD  PRLPAPKGQT
      Ricept-1   RALKAAFGKV  WRLEDTGGSI  IGGTIKTIQE  RGKNPKPPRD  PRLPTPKGQT
    Cottonpt-1   LSMKAAFGRV  WKLEEIGGSI  IGGTFKTIQE  RNKTPKPPRD  PRLPKPKGQT
    Soybeanpt1   LSMKAAFGKV  WKLEKNGGSI  IGGTFKAIQE  RNGASKPPRD  PRLPKPKGQT
       Sugpt-1   LSMKAAFGKV  WKLEQKGGSI  IGGTLKAIQE  RGSNPKPPRD  QRLPKPKGQT 301                                                           350
     Rapept-1    VGSFRKGLTM  LPEAISARLG  DKVKVSWKLS  SITKLASGEY  SLTYETPEGI
```

TABLE 1-continued

Comparison of Protox-1 Amino Acid Sequences from Arabidopsis ("Arabpt-1"; SEQ ID NO:2), Maize ("Mzpt-1"; SEQ ID NO:6), Wheat ("Wtpt-1"; SEQ ID NO:10), Soybean ("Soybeanpt-1"; SEQ ID NO:12), Cotton ("Cottonpt-1"; SEQ ID NO:16), Sugar beet ("Sugpt-1"; SEQ ID NO:18), Rape ("Rapet-1"; SEQ ID NO:20), Rice ("Ricept-1"; SEQ ID NO:22), and Sorghum ("Sorghumpt-1"; SEQ ID NO:24)

Alignment is performed using the PileUp program (GCG package, University of Wisconsin, Madison, WI). Positions that may be modified according to the teachings herein to confer or enhance inhibitor resistance are shown in bold type.

```
     Arabpt-1  VGSFRKGLRM LPEAISARLG SKVKLSWKLS GITKLESGGY NLTYETPDGL
  Sorghumpt-1  VASFRKGLAM LPNAITSSLG SKVKLSWKLT SMTKSDGKGY VLEYETPEGV
       Mzpt-1  VASFRKGLAM LPNAITSSLG SKVKLSWKLT SITKSDDKGY VLEYETPEGV
       Wtpt-1  VASFRKGLAM LPNAIASRLG SKVKLSWKLT SITKADNQGY VLGYETPEGL
     Ricept-1  VASFRKGLTM LPDAITSRLG SKVKLSWKLT SITKSDNKGY ALVYETPEGV
   Cottonpt-1  VGSFRKGLTM LPEAIANSLG SNVKLSWKLS SITKLGNGGY NLTFETPEGM
   Soybeanpt1  VGSFRKGLTM LPDAISARLG NKVKLSWKLS SISKLDSGEY SLTYETPEGV
       Sugpt-1 VGSFRKGLVM LPTAISARLG SRVKLSWTLS SIVKSLNGEY SLTYDTPDGL 351                                             400
     Rapept-1  VTVQSKSVVM TVPSHVASSL LRPLSDSAAE ALSKLYYPPV AAVSISYAKE
     Arabpt-1  VSVQSKSVVM TVPSHVASGL LRPLSESAAN ALSKLYYPPV AAVSISYPKE
  Sorghumpt-1  VLVQAKSVIM TIPSYVASDI LRPLSGDAAD VLSRFYYPPV AAVTVSYPKE
       Mzpt-1  VSVQAKSVIM TIPSYVASNI LRPLSSDAAD ALSRFYYPPV AAVTVSYPKE
       Wtpt-1  VSVQAKSVIM TIPSYVASDI LRPLSIDAAD ALSKFYYPPV AAVTVSYPKE
     Ricept-1  VSVQAKTVVM TIPSYVASDI LRPLSSDAAD ALSIFYYPPV AAVTVSYPKE
   Cottonpt-1  VSLQSRSVVM TIPSHVASNL LHPLSAAAAD ALSQFYYPPV ASVTVSYPKE
   Soybeanpt1  VSLQCKTVVL TIPSYVASTL LRPLSAAAAD ALSKFYYPPV AAVSISYPKE
       Sugpt-1 VSVRTKSVVM TVPSYVASRL LRPLSDSAAD SLSKFYYPV  AAVSLSPKE 401                                             450
     Rapept-1  AIRSECLIDG ELKGFGQLHP RTQKVETLGT IYSSSLFPNR APPGRVLLLN
     Arabpt-1  AIRTECLIDG ELKGFGQLHP RTQGVETLGT IYSSSLFPNR APPGRILLLN
  Sorghumpt-1  AIRKECLIDG ELQGFGQLHP RSQGVETLGT IYSSSLFPNR APAGRVLLLN
       Mzpt-1  AIRKECLIDG ELQGFGQLHP RSQGVETLGT IYSSSLFPNR APDGRVLLLN
       Wtpt-1  AIRKECLIDG ELQGFGQLHP RSQGVETLGT IYSSSLFPNR APAGRVLLLN
     Ricept-1  AIRKECLIDG ELQGFGQLHP RSQGVETLGT IYSSSLFPNR APAGRVLLLN
   Cottonpt-1  AIRKECLIDG ELKGFGQLHP RSQGIETLGT IYSSSLFPNR APSGRVLLLN
   Soybeanpt1  AIRSECLIDG ELKGFGQLHP RSQGVETLGT IYSSSLFPNR APPGRVLLLN
       Sugpt-1 AIRSECLING ELQGFGQLHP RSQGVETLGT IYSSSLFPGR APPGRILILS 451                                             500
     Rapept-1  YIGGATNTGI LSKSEGELVE AVDRDLRKML IKPSSTDPLV LGVKLWPQAI
     Arabpt-1  YIGGSTNTGI LSKSEGELVE AVDRDLRKML IKPNSTDPLK LGVRVWPQAI
  Sorghumpt-1  YIGGATNTGI VSKTESELVE AVDRDLRKML INPTAVDPLV LGVRVWPQAI
       Mzpt-1  YIGGATNTGI VSKTESELVE AVDRDLRKML INSTAVDPLV LGVRVWPQAI
       Wtpt-1  YIGGSTNTGI VSKTESDLVG AVDRDLRKML INPRAADPLA LGVRVWPQAI
     Ricept-1  YIGGSTNTGI VSKTESELVE AVDRDLRKML INPRAVDPLV LGVRVWPQAI
   Cottonpt-1  YIGGATNTGI LSKTEGELVE AVDRDLRKML INPNAKDPLA LGVRVWPKAI
   Soybeanpt1  YIGGATNTGI LSKTDSELVE TVDRDLRKIL INPNAQDPFV VGVRLWPQAI
       Sugpt-1 YIGGAKNPGI LNKSKDELAK TVDKDLRRML INPAKLPRV  LGVRVWPQAI 501                                             550
     Rapept-1  PQFLIGHIDL VDAAKASLSS SGHEGLFLGG NYVAGVALGR CVEGAYETAT
     Arabpt-1  PQFLVGHFDI LDTAKASLTS SGYEGLFLGG NYVAGVALGR CVEGAYETAI
  Sorghumpt-1  PQFLVGHLDL LEAAKSALDQ GGYNGLFLGG NYVAGVALGR CIEGAYESAA
       Mzpt-1  PQFLVGHLDL LEAAKAALDR GGYDGLFLGG NYVAGVALGR CVEGAYESAS
       Wtpt-1  PQFLIGHLDR LAAAKSALGQ GGYDGLFLGG KYVAGVALGR CIEGAYESAS
     Ricept-1  PQFLIGHLDH LEAAKSALGK GGYDGLFLGG NYVAGVALGR CVEGAYESAS
   Cottonpt-1  PQFLVGHLDL LDSAKMALRD SGFHGLFLGG NYVAGVALGR CVEGAYEVAA
   Soybeanpt1  PQFLVGHLDL LDVAKASIRN TGFEGLFLGG NYVSGVALGR CVEGAYEVAA
       Sugpt-1 PQFSIGHFDL LDAAKAALTD TGVKGLFLGG NYVSGVALGR CIEGAYESAA 551         563
     Rapept-1  QVNDFMSRYA YK*
     Arabpt-1  EVNNFMSRYA YK*
  Sorghumpt-1  QIYDFLTKYA YK*
       Mzpt-1  QISDFLTKYA YK*
       Wtpt-1  QVSDFLTKYA YK*
     Ricept-1  QISDYLTKYA YK*
   Cottonpt-1  EVKEFLSQYA YK*
   Soybeanpt1  EVNDFLTNRV YK*
       Sugpt-1 EVVDFLSQYS DK*
```

Example 3

Isolation of a Cotton Protox-1 cDNA Based on Sequence Homology to a Maize Protox-1 Coding Sequence A Lambda Uni-Zap cDNA library prepared from *Gossypium hirsutum* L. (72 hr. dark grown cotyledons) was obtained from Dr. Dick Trelease, Dept. of Botany, Arizona State University (Ni W. and Trelease R. N., *Arch. Biochem. Biophys.* 289:237–243 (1991)). Approximately 50,000 pfu of the library was plated at a density of approximately 5,000 pfu per 10 cm Petri dish and duplicate filter lifts were made onto Colony/Plaque Screen membranes (NEN Dupont). The plaque lifts were probed with the maize Protox-1 cDNA (SEQ ID NO:5) labeled with 32P-dCTP by the random priming method (Life Technologies). Hybridization conditions were 7% sodium dodecyl sulfate (SDS), 0.5M NaPO4 pH 7.0, 1 mM EDTA at 50° C. Wash conditions were 2×SSC, 1% SDS at 50° C. (Church and Gilbert (1984)). Positively hybridizing plaques were purified and in vivo excised into pBluescript plasmids. The sequence of the cDNA inserts was determined by the chain termination method using dideoxy terminators labeled with fluorescent dyes (Applied Biosystems, Inc.). The longest cotton cDNA obtained, designated "cotton Protox-1", appears to be full-length based on comparison with the other known plant protox peptide sequences (Table 1). Cotton Protox-1 is 1826 bp in length and encodes a protein of 58.2 kDa. The nucleotide sequence of this cDNA and the amino acid sequence it encodes are set forth in SEQ ID NOs:13 and 14, respectively. The cotton protein is 77% identical (86% similar) to the Maize Protox-1 protein.

Cotton Protox-1, in the pBluescript SK vector, was deposited Jul. 1, 1996 as pWDC-15 (NRRL #B-21594).

Example 4

Isolation of a Sugar Beet Protox-1 cDNA Based on Sequence Homology to an Arabidopsis Protox-1 Coding Sequence A Lambda-Zap cDNA library prepared from Beta vulgaris was obtained from Dr. Philip Rea, Dept. of Botany, Plant Science Institute, Philadelphia, Pa. (Yongcheol Kim, Eugene J. Kim, and Philip A. Rea, *Plant Physiol.* 106: 375–382 (1994)). Approximately 50,000 pfu of the cDNA library were plated at a density of approximately 5,000 pfu per 10 cm Petri dish and duplicate filter lifts were made onto nitrocellulose membranes (Schleicher and Schuell). The plaque lifts were probed with the Arabidopsis Protox-1 cDNA (SEQ ID NO:1) labeled with 32P-dCTP by the random priming method (Life Technologies). Hybridization conditions were 7% sodium dodecyl sulfate (SDS), 0.5M NaPO4 pH 7.0, 1 mM EDTA at 50° C. Wash conditions were 2×SSC, 1% SDS at 50° C.; (Church and Gilbert (1984)). Positively hybridizing plaques were purified and in vivo excised into pBluescript plasmids. The sequences of the cDNA inserts were determined by the chain termination method using dideoxy terminators labeled with fluorescent dyes (Applied Biosystems, Inc.). The longest sugar beet Protox-1 cDNA obtained, designated "sugar beet Protox-1", is full-length based on comparison with the other known plant protox peptide sequences (Table 1). Sugar beet Protox-1 is 1910 bp in length and encodes a protein of 60 kDa. The nucleotide sequence of this cDNA and the amino acid sequence it encodes are set forth in SEQ ID NOs:15 and 16, respectively. The sugar beet protein is 73% identical (82% similar) to the Arabidopsis Protox-1 protein.

Sugar beet Protox-1, in the pBluescript SK vector, was deposited Jul. 29, 1996, as pWDC-16 (NRRL #B-21595N).

Example 5

Isolation of a Rape Protox-1 cDNA Based on Sequence Homology to an Arabidopsis Protox-1 Coding Sequence A Lambda Uni-Zap II cDNA library prepared from Brassica napus (3–4 wk. mature green leaves) was obtained from Dr. Guenther Ochs, Institut Fuer Aligemeine Botanik, Johannes Gutenberg-Universitaet Mainz, Germany (Gunther Ochs, Gerald Schock, and Aloysius Wild, *Plant Physiol.* 103: 303–304 (1993)). Approximately 50,000 pfu of the cDNA library were plated at a density of approximately 5,000 pfu per 10 cm Petri dish and duplicate filter lifts were made onto nitrocellulose membranes (Schleicher and Schuell). The plaque lifts were probed with the Arabidopsis Protox-1 cDNA (SEQ ID NO:1) labeled with 32P-dCTP by the random priming method (Life Technologies). Hybridization conditions were 7% sodium dodecyl sulfate (SDS), 0.5M NaPO4 pH 7.0, 1 mM EDTA at 50° C. Wash conditions were 2×SSC, 1% SDS at 50° C. (Church and Gilbert (1984)). Positively hybridizing plaques were purified and in vivo excised into pBluescript plasmids. The sequences of the cDNA inserts were determined by the chain termination method using dideoxy terminators labeled with fluorescent dyes (Applied Biosystems, Inc.). The longest rape Protox-1 cDNA obtained, designated "rape Protox-1", is full-length based on comparison with the other known plant protox peptide sequences (Table 1). Rape Protox-1 is 1784 bp in length and encodes a protein of 57.3 kD. The nucleotide sequence of this cDNA and the amino acid sequence it encodes are set forth in SEQ ID NOs: 17 and 18, respectively. The rape protein is 87% identical (92% similar) to the Arabidopsis Protox-1 protein.

Rape Protox-1, in the pBluescript SK vector, was deposited Aug. 23, 1996, as pWDC-17 (NRRL #B-21615).

Example 6

Isolation of a Rice Protox-1 cDNA Based on Sequence Homology to a Maize Protox-1 Coding Sequence A Lambda gt11 cDNA library prepared from Oryza sativa (5 day etiolated shoots) was purchased from Clontech. Approximately 50,000 pfu of the cDNA library were plated at a density of approximately 5,000 pfu per 10 cm Petri dish and duplicate filter lifts were made onto nitrocellulose membranes (Schleicher and Schuell). The plaque lifts were probed with the maize Protox-1 cDNA (SEQ ID NO:5) labeled with 32P-dCTP by the random priming method (Life Technologies). Hybridization conditions were 7% sodium dodecyl sulfate (SDS), 0.5M NaPO4 pH 7.0, 1 mM EDTA at 50° C. Wash conditions were 2×SSC, 1% SDS at 50° C. (Church and Gilbert (1984)). Positively hybridizing plaques were purified, and lambda DNA was prepared using the Wizard Lambda-Prep kit (Promega). The cDNA inserts were subcloned as EcoRI fragments into the pBluescript SK vector using standard techniques. The sequences of the cDNA inserts were determined by the chain termination method using dideoxy terminators labeled with fluorescent dyes (Applied Biosystems, Inc.). The longest rice Protox-1 cDNA obtained, designated "rice Protox-1", was 1224 bp in length. Rice Protox-1 lacks coding sequence for the transit peptide plus approximately 172 amino acids of the mature coding sequence based on comparison with the other known plant protox peptide sequences (Table 1). The nucleotide sequence of this partial cDNA and the amino acid sequence it encodes are set forth in SEQ ID NOs:19 and 20, respectively.

Rice Protox-1, in the pBluescript SK vector, was deposited Dec. 6, 1996, as pWDC-18 (NRRL #B-21648).

Example 7

Isolation of a Sorghum Protox-1 cDNA Based on Sequence Homology to a Maize Protox-1 Coding Sequence A Lambda-Zap II cDNA library prepared from Sorghum bicolor (3–6 day green seedlings) was obtained from Dr. Klaus Pfizenmaier, Institute of Cell Biology and Immunology, University of Stuttgart, Germany (Harald Wajant, Karl-Wolfgang Mundry, and Klaus Pfizenmaier, Plant Mol. Biol. 26: 735–746 (1994)). Approximately 50,000 pfu of the cDNA library were plated at a density of approximately 5,000 pfu per 10 cm Petri dish and duplicate filter lifts were made onto nitrocellulose membranes (Schleicher and Schuell). The plaque lifts were probed with the maize Protox-1 cDNA (SEQ ID NO:5) labeled with 32P-dCTP by the random priming method (Life Technologies). Hybridization conditions were 7% sodium dodecyl sulfate (SDS), 0.5M NaPO4 pH 7.0, 1 mM EDTA at 50° C. Wash conditions were 2×SSC, 1% SDS at 50° C. (Church and Gilbert (1984)). Positively hybridizing plaques were purified and in vivo excised into pBluescript plasmids. The sequences of the cDNA inserts were determined by the chain termination method using dideoxy terminators labeled with fluorescent dyes (Applied Biosystems, Inc.). The longest sorghum Protox-1 cDNA obtained, designated "sorghum Protox-1", was 1590 bp in length. Sorghum Protox-1 lacks coding sequence for the transit peptide plus approximately 44 amino acids of the mature coding sequence based on comparison with the other known plant protox peptide sequences (Table 1). The nucleotide sequence of this partial cDNA and the amino acid sequence it encodes are set forth in SEQ ID NOs:21 and 22, respectively.

Sorghum Protox-1, in the pBluescript SK vector, was deposited Dec. 6, 1996, as pWDC-19 (NRRL #B-21649).

Example 8

Demonstration of Plant Protox Clone Sensitivity to Protox Inhibitory Herbicides in a Bacterial System Liquid cultures of Protox-1/SASX38, Protox-2/SASX38 and pBluescript/XL1-Blue were grown in L amp$^{100}$. One hundred microliter aliquots of each culture were plated on L amp$^{100}$ media containing various concentrations (1.0 nM–10 mM) of a protox inhibitory aryluracil herbicide of formula XVII. Duplicate sets of plates were incubated for 18 hours at 37° C.

The protox$^+$ E. coli strain XL1-Blue showed no sensitivity to the herbicide at any concentration, consistent with reported resistance of the native bacterial enzyme to similar herbicides. The Protox-1/SASX38 was clearly sensitive, with the lawn of bacteria almost entirely eliminated by inhibitor concentrations as low as 10 nM. The Protox-2/SASX38 was also sensitive, but only at a higher concentration (10 μM) of the herbicide. The herbicide was effective even on plates maintained almost entirely in the dark. The toxicity of the herbicide was entirely eliminated by the addition of 20 μg/ml hematin to the plates.

The different herbicide tolerance between the two plant Protox strains is likely the result of differential expression from these two plasmids, rather than any inherent difference in enzyme sensitivity. Protox-1/SASX38 grows much more slowly than Protox-2/SASX38 in any heme-deficient media. In addition, the MzProtox-2/SASX38 strain, with a growth rate comparable to Arab Protox-1/SASX38; is also very sensitive to herbicide at the lower (10–100 nM) concentrations.

Section B: Identification and Characterization of Plant Protox Genes Resistant to Protox-Inhibitory Herbicides Example 9

Selecting for Plant Protox Genes Resistant to Protox-Inhibitory Herbicides in the E. coli Expression System An Arabidopsis thaliana (Landsberg) cDNA library in the plasmid vector pFL61 (Minet et al., Plant J. 2: 417–422 (1992) was obtained and amplified. The E. coli hemG mutant SASX38 (Sasarman et al., J. Gen. Microbiol. 113:297(1979)) was obtained and maintained on L media containing 20 ug/ml hematin (United States Biochemicals). The plasmid library was transformed into SASX38 by electroporation using the Bio-Rad Gene Pulser and the manufacturer's conditions. The electroporated cells were plated on L agar containing 100 ug/ml ampicillin at a density of approximately 500,000 transformants/10 cm plate. The cells were then incubated at 37° C. for 40 hours in low light and selected for the ability to grow without the addition of exogenous heme. Heme prototrophs were recovered at a frequency of 400/10$^7$ from the pFL61 library. Sequence analysis of twenty-two complementing clones showed that nine are of the type designated "Protox-1," the protox gene expected to express a chloroplastic protox enzyme.

The pFL61 library is a yeast expression library, with the Arabidopsis cDNAs inserted bidirectionally. These cDNAs can also be expressed in bacteria. The protox cDNAs apparently initiate at an in-frame ATG in the yeast PGK 3' sequence approximately 10 amino acids 5' to the NotI cloning site in the vector and are expressed either from the lacZ promoter 300 bp further upstream or from an undefined cryptic bacterial promoter. Because Protox-1 cDNAs that included significant portions of a chloroplast transit sequence inhibited the growth of the E. coli SASX38 strain, the clone with the least amount of chloroplast transit sequence attached was chosen for mutagenesis/herbicide selection experiments. This clone, pSLV19, contains only 17 amino acids of the putative chloroplast transit peptide, with the DNA sequence beginning at bp 151 of the Arabidopsis Protox-1 cDNA (SEQ ID NO:1).

The plasmid pSLV19 was transformed into the random mutagenesis strain XL1-Red (Stratagene, La Jolla, Calif.). The transformation was plated on L media containing 50 ug/ml ampicillin and incubated for 48 hours at 37° C. Lawns of transformed cells were scraped from the plates and plasmid DNA prepared using the Wizard Megaprep kit (Promega, Madison, Wis.). Plasmid DNA isolated from this mutator strain is predicted to contain approximately one random base change per 2000 nucleotides (see Greener et al., Strategies 7(2):32–34 (1994).

The mutated plasmid DNA was transformed into the hemG mutant SASX38 (Sasarman et al., J. Gen. Microbiol. 113:297 (1979) and plated on L media containing various concentrations of protox-inhibiting herbicide. The plates were incubated for 2 days at 37° C. Plasmid DNA was isolated from all colonies that grew in the presence of herbicide concentrations that effectively killed the wild type strain. The isolated DNA was then transformed into SASX38 and plated again on herbicide to ensure that the resistance observed was plasmid-borne. The protox coding sequence from plasmids passing this screen was excised by NotI digestion, recloned into an unmutagenized vector, and tested again for the ability to confer herbicide tolerance. The DNA sequence of protox cDNAs that conferred herbicide resistance was then determined and mutations identified by comparison with the wild type Arabidopsis Protox-1 sequence (SEQ ID NO:1).

A single coding sequence mutant was recovered from the first mutagenesis experiment. This mutant leads to enhanced herbicide "resistance" only by increasing growth rate. It contains a C to A mutation at nucleotide 197 in SEQ ID NO:1 in the truncated chloroplast transit sequence of pSLV19, converting an ACG codon for threonine to an AAG codon for lysine at amino acid 56 of SEQ ID NO:2, and resulting in better complementation of the bacterial mutant. This plasmid also contains a silent coding sequence mutation at nucleotide 1059, with AGT (Ser) changing to AGC (Ser). This plasmid was designated pMut-1.

The pMut-1 plasmid was then transformed into the mutator XL1-Red strain as described above and the mutated DNA was isolated and plated on an herbicide concentration that is lethal to the unmutagenized pMut-1 protox gene. Herbicide tolerant colonies were isolated after two days at 37° C. and analyzed as described above. Multiple plasmids were shown to contain herbicide resistant protox coding sequences. Sequence analysis indicated that the resistant genes fell into two classes. One resistance mutation identified was a C to T change at nucleotide 689 in the Arabidopsis Protox-1 sequence set forth in SEQ ID NO:1. This change converts a GCT codon for alanine at amino acid 220 of SEQ ID NO:2 to a GTT codon for valine, and was designated pAraC-1 Val.

A second class of herbicide resistant mutant contains an A to G change at nucleotide 1307 in the Arabidopsis Protox-1 sequence. This change converts a TAC codon for tyrosine at amino acid 426 to a TGC codon for cysteine, and was designated pAraC-2Cys.

A third resistant mutant has a G to A change at nucleotide 691 in the Arabidopsis Protox-1 sequence. This mutation converts a GGT codon for glycine at amino acid 221 to an AGT codon for serine at the codon position adjacent to the mutation in pAraC-1. This plasmid was designated pAraC-3Ser.

Resistant mutant pAraC-2Cys, in the pMut-1 plasmid, was deposited on Nov. 14, 1994 under the designation pWDC-7 with the Agricultural Research Culture Collection and given the deposit designation NRRL #21339N.

Example 10

Additional Herbicide-Resistant Codon Substitutions at Positions Identified in the Random Screen The amino acids identified as herbicide resistance sites in the random screen are replaced by other amino acids and tested for function and for herbicide tolerance in the bacterial system. Oligonucleotide-directed mutagenesis of the Arabidopsis Protox-1 sequence is performed using the Transformer Site-Directed Mutagenesis Kit (Clontech, Palo Alto, Calif.). After amino acid changes are confirmed by sequence analysis, the mutated plasmids are transformed into SASX38 and plated on L-amp$^{100}$ media to test for function and on various concentrations of protox-inhibiting herbicide to test for tolerance.

This procedure is applied to the alanine codon at nucleotides 688–690 and to the tyrosine codon at nucleotides 1306–1308 of the Arabidopsis Protox-1 sequence (SEQ ID NO:1). The results demonstrate that the alanine codon at nucleotides 688–690 can be changed to a codon for valine, threonine, leucine, cysteine, or isoleucine to yield an herbicide-resistant protox enzyme that retains function. The results further demonstrate that the tyrosine codon at nucleotides 1306–1308 can be changed to a codon for cysteine, isoleucine, leucine, threonine, methionine, valine, or alanine to yield an herbicide-resistant protox enzyme that retains function.

Example 11

Isolation of Additional Mutations that Increase Enzyme Function and/or Herbicide Tolerance of Previously Identified Resistant Mutants Plasmids containing herbicide resistant protox genes are transformed into the mutator strain XL1-Red and mutated DNA is isolated as described above. The mutated plasmids are transformed into SASX38 and the transformants are screened on herbicide concentrations sufficient to inhibit growth of the original "resistant" mutant. Tolerant colonies are isolated and the higher tolerance phenotype is verified as being coding sequence dependent as described above. The sequence of these mutants is determined and mutations identified by comparison to the progenitor sequence.

This procedure was applied to the pAraC-1 Val mutant described above. The results demonstrate that the serine codon at amino acid 305 (SEQ ID NO:2) can be changed to a codon for leucine to yield an enzyme with higher tolerance to protox-inhibiting herbicides than the pAraC-1 Val mutant alone. This second site mutation is designated AraC305Leu. The same results are demonstrated for the threonine codon at amino acid 249, where a change to either isoleucine or to alanine leads to a more tolerant enzyme. These changes are designated AraC249Ile and AraC249Ala, respectively.

The procedure was also applied to the pAraC-2Cys mutant described above. The results demonstrate that the proline codon at amino acid 118 (SEQ ID NO:2) can be changed to a codon for leucine to yield an enzyme with higher tolerance to protox-inhibiting herbicides than the pAraC-1 Cys mutant alone. This mutation is designated AraC118Leu. The same results are demonstrated for the serine codon at amino acid 305, where a change to leucine leads to a more tolerant pAraC-2Cys enzyme. This change was also isolated with the pAraC-1 Val mutant as described above and is designated AraC305Leu. Additional mutations that enhance the herbicide resistance of the pAraC-2Cys mutant include an asparagine to serine change at amino acid 425, designated AraC425Ser, and a tyrosine to cysteine at amino acid 498, designated AraC498Cys.

These changes are referred to as "second site" mutations, because they are not sufficient to confer herbicide tolerance alone, but rather enhance the function and/or the herbicide tolerance of an already mutant enzyme. This does not preclude the possibility that other amino acid substitutions at these sites could suffice to produce an herbicide tolerant enzyme since exhaustive testing of all possible replacements has not been performed.

Example 12

Combining Identified Resistance Mutations with Identified Second Site Mutations to Create Highly Functional/Highly Tolerant Protox Enzymes The AraC305Leu mutation described above was found to enhance the function/herbicide resistance of both the AraC-1

Val and the AraC-2Cys mutant plasmids. In an effort to test the general usefulness of this second site mutation, it was combined with the AraC-2Leu, AraC-2Val, and AraC-2Ile mutations and tested for herbicide tolerance. In each case, the AraC305Leu change significantly increased the growth rate of the resistant protox mutant on protox-inhibiting herbicide. Combinations of the AraC-2Ile resistant mutant with either the second site mutant AraC249Ile or AraC118Leu also produced more highly tolerant mutant protox enzymes. The AraC249Ile mutation demonstrates that a second site mutation identified as enhancing an AraC-1 mutant may also increase the resistance of an AraC-2 mutant. A three mutation plasmid containing AraC-2Ile, AraC305Leu, and AraC249Ile has also been shown to produce a highly functional, highly herbicide tolerant protox-1 enzyme.

Example 13

Identification of Sites in the Maize Protox-1 Gene that can be Mutated to Give Herbicide Tolerance The pMut-1 Arabidopsis Protox-1 plasmid described above is very effective when used in mutagenesis/screening experiments in that it gives a high frequency of genuine coding sequence mutants, as opposed to the frequent up-promoter mutants that are isolated when other plasmids are used. In an effort to create an efficient plasmid screening system for maize Protox-1, the maize cDNA was engineered into the pMut-1 vector in approximately the same sequence context as the Arabidopsis cDNA. Using standard methods of overlapping PCR fusion, the 5' end of the pMut-1 Arabidopsis clone (including 17 amino acids of chloroplast transit peptide with one mis-sense mutation as described above) was fused to the maize Protox-1 cDNA sequence starting at amino acid number 14 (SEQ ID NO:6) of the maize sequence. The 3' end of the maize cDNA was unchanged. NotI restriction sites were placed on both ends of this fusion, and the chimeric gene was cloned into the pFL61 plasmid backbone from pMut-1. Sequence analysis revealed a single nucleotide PCR-derived silent mutation that converts the ACG codon at nucleotides 745–747 (SEQ ID NO:5) to an ACT codon, both of which encode threonine. This chimeric Arab-maize Protox-1 plasmid is designated pMut-3.

The pMut-3 plasmid was transformed into the mutator XL1-Red strain as described above and the mutated DNA was isolated and plated on an herbicide concentration that was lethal to the unmutagenized pMut-3 maize protox gene. Herbicide tolerant colonies were isolated after two days at 37° C. and analyzed as described above. This analysis revealed multiple plasmids containing herbicide resistant protox coding sequences. Sequence analysis showed 5 single base changes that individually result in an herbicide tolerant maize Protox-1 enzyme. Three of these mutations correspond to amino acid changes previously shown to confer tolerance at the homologous position in the Arabidopsis Protox-1 gene. Two of the three are pMzC-1Val and pMzC-1Thr, converting the alanine (GCT) at amino acid 164 (SEQ ID NO:6) to either valine (GAT) or to threonine (ACT). This position corresponds to the pAraC-1 mutations described above. The third analogous change converts the glycine (GGT) at amino acid 165 to Serine (AGT), corresponding to the AraC-3Ser mutation described above. These results serve to validate the expectation that herbicide-tolerant mutations identified in one plant protox gene may also confer herbicide tolerance in an equivalent plant protox gene from another species.

Two of the mutations isolated from the maize Protox-1 screen result in amino acid changes at residues not previously identified as herbicide resistance sites. One change converts cysteine (TGC) to phenylalanine (TTC) at amino acid 159 of the maize Protox-1 sequence (SEQ ID NO:6). The second converts isoleucine (ATA) to threonine (ACA) at amino acid 419.

Additional amino acid substitutions were made and tested at three of the maize mutant sites. Tolerance was demonstrated when glycine 165 was changed to leucine or when cysteine 159 was changed to either leucine or to lysine. Tolerant enzymes were also created by changing isoleucine 419 to histidine, glycine, or asparagine.

Individual amino acid changes that produced highly herbicide tolerant Arabidopsis Protox-1 enzymes were engineered into the maize Protox-1 gene by site-directed mutagenesis as described above. Bacterial testing demonstrated that changing the alanine (GCT) at amino acid 164 (SEQ ID NO:6) to leucine (CTT) produced a highly tolerant maize enzyme. No mutation analogous to the AraC-2 site in Arabidopsis was isolated in the maize random screen. However, changing this site, tyrosine 370 in the maize enzyme (SEQ ID NO:6), to either isoleucine or methionine did produce an herbicide tolerant enzyme.

Example 14

Identification of Sites in the Wheat Protox-1 Gene that can be Mutated to Give Herbicide Tolerance To create an efficient plasmid screening system for wheat Protox-1, the wheat cDNA was engineered into the pMut-1 vector as described above for the maize cDNA. This chimeric Arab-wheat Protox-1 plasmid is designated pMut-4. The pMut-4 DNA was mutated and screened for herbicide tolerance as described above. This analysis revealed multiple plasmids containing herbicide resistant protox coding sequences. Sequence analysis showed 7 single base changes that individually result in an herbicide tolerant wheat Protox-1 enzyme. Four of these mutations correspond to amino acid changes previously shown to confer tolerance at the homologous position in the Arabidopsis and/or in the maize Protox-1 gene. Two convert the alanine (GCT) at amino acid 211 (SEQ ID NO:10) to either valine (GAT) or to threonine (ACT). This position corresponds to the pAraC-1 mutations described above. The third analogous change converts the glycine (GGT) at amino acid 212 to Serine (AGT), corresponding to the AraC-3Ser mutation described above. The fourth converts isoleucine (ATA) to threonine (ACA) at amino acid 466, corresponding to the Mz419Thr mutant from maize.

Three of the mutations isolated from the wheat Protox-1 screen result in amino acid changes at residues not previously identified as herbicide resistance sites. One change converts valine (GTT) to leucine (CTT) at amino acid 356 of the wheat Protox-1 sequence (SEQ ID NO:10). A second converts serine (TCT) to proline (CCT.) at amino acid 421. The third converts valine (GTT) to alanine (GCT) at amino acid 502.

Example 15

Identification of Sites in the Soybean Protox-1 Gene that can be Mutated to Give Herbicide Tolerance To create an efficient plasmid screening system for soybean Protox-1, the soybean cDNA was engineered into the pMut-1 vector as described above for the maize cDNA. This chimeric Arab-soybean Protox-1 plasmid is designated pMut-5. The pMut-5 DNA was mutated and screened for herbicide tolerance as described above. This analysis revealed multiple plasmids containing herbicide resistant protox coding sequences. Sequence analysis showed 4 single base changes that individually result in an herbicide tolerant soybean Protox-1 enzyme. Two of these mutations correspond to amino acid changes previously shown to confer tolerance at the homologous position in the Arabidopsis and/or in the wheat Protox-1 gene. One converts the alanine (GCA) at amino acid 226 (SEQ ID NO:12) to threonine (ACA). This position corresponds to the pAraC-1Thr mutation described above. The second analogous change converts the valine (GTT) at amino acid 517 to alanine (GCT), corresponding to the Wht502Val mutation from wheat.

Two of the mutations isolated from the soybean Protox-1 screen result in amino acid changes at a residue not previously identified as an herbicide resistance site. One change converts proline (CCT) to serine (TCT) at amino acid 369 of the soybean Protox-1 sequence (SEQ ID NO:12). A second converts this same proline369 to histidine (CAT).

Individual amino acid changes that produced highly herbicide tolerant Arabidopsis Protox-1 enzymes were engineered into the soybean Protox-1 gene by site directed mutagenesis as described above. Bacterial testing demonstrated that changing the alanine (GCA) at amino acid 226 (SEQ ID NO:12) to leucine produced a tolerant soybean enzyme.

Changing the tyrosine (TAC) at amino acid 432 (SEQ ID NO:12) to either leucine or isoleucine also produced an herbicide tolerant enzyme.

Example 16

Identification of Sites in the Sugar Beet Protox-1 Gene that can be Mutated to Give Herbicide Tolerance To create an efficient plasmid screening system for sugar beet Protox-1, the sugar beet cDNA was engineered into the pMut-1 vector as described above for the maize cDNA. This chimeric Arab-sugar beet Protox-1 plasmid is designated pMut-6. The pMut-6 DNA was mutated and screened for herbicide tolerance as described above, This analysis revealed multiple plasmids containing herbicide resistant protox coding sequences. Sequence analysis showed a single base change that results in an herbicide tolerant sugar beet Protox-1 enzyme. This change converts tyrosine (TAC) at amino acid 449 to cysteine (TGC) and is analogous to the AraC-2 mutation in Arabidopsis.

Individual amino acid changes that produced highly herbicide tolerant Arabidopsis Protox-1 enzymes were engineered into the sugar beet Protox-1 gene by site directed mutagenesis as described above. Bacterial testing demonstrated that changing the tyrosine (TAC) at amino acid 449 to either leucine, isoleucine, valine, or methionine produced an herbicide tolerant sugar beet enzyme.

Example 17

Identification of Sites in the Cotton Protox-1 Gene that can be Mutated to Give Herbicide Tolerance In an effort to create an efficient plasmid screening system for cotton Protox-1, the cotton cDNA was engineered into the pMut-1 vector as described above for the maize cDNA. This chimeric Arab-cotton Protox-1 plasmid is designated pMut-7. The pMut-7 DNA was mutated and screened for herbicide tolerance as described above. This analysis revealed multiple plasmids containing herbicide resistant protox coding sequences. Sequence analysis showed 3 single base changes that individually result in an herbicide tolerant cotton Protox-1 enzyme. Two mutants change tyrosine (TAC) at amino acid 428 (SEQ ID NO:16) to cysteine (TGC) and to arginine (CGC), respectively. Arginine is a novel substitution giving tolerance at this previously identified AraC-2 site. The third mutation converts proline (CCC) to serine (TCC) at amino acid 365. This change corresponds to the soybean mutant Soy369Ser.

Example 18

Demonstration of Resistant Mutations' Cross-Tolerance to Various Protox-Inhibiting Compounds Resistant mutant plasmids, originally identified based on resistance against a single protox inhibitory herbicide, were tested against a spectrum of other protox inhibiting compounds. For this test, the SASX38 strain containing the wild-type plasmid is plated on a range of concentrations of each compound to determine the lethal concentration for each one. Resistant mutant plasmids in SASX38 are plated and scored for the ability to survive on a concentration of each compound at least 10 fold higher than the concentration that is lethal to the SASX38 strain containing the wild-type plasmid.

Results from bacterial cross-tolerance testing, illustrated in Tables 3A and 3B below, show that each of the mutations identified confers tolerance to a variety of protox inhibiting compounds.

TABLE 3A

Cross Tolerance of Plant Protox Mutants to Various Protox Inhibitors

| Formula | AraC-1Val | AraC-2Cys | AraC-1Thr | AraC-3Thr | MzC-1Val |
|---|---|---|---|---|---|
| XVII | + | + | + | + | + |
| VIIa | + | + | + | − | + |
| IV | ++ | − | ++ | ++ | − |
| XV | + | + | + | + | + |
| XI | − | + | + | ++ | + |
| XVI | − | − | − | − | + |
| XII | + | − | ++ | ++ | ++ |
| XIV | + | − | + | + | + |
| *X | | | | | |

+ = 10 × or more tolerant than WT
++ = 100 × or more tolerant than WT
− = no cross tolerance
* = this compound was tested but provided no information

TABLE 3B

Cross Tolerance of Plant Protox Mutants to Various Protox Inhibitors

| | AraC-1Leu | AraC-2IIe | AraC-1Leu + AraC-2Met | AraC-1Leu + AraC-2Leu | AraC-2IIe + AraC305Leu | AraC-2Cys + AraC425Ser | AraC-2Leu + AraC425Ser | AraC-2Met + AraC425Ser |
|---|---|---|---|---|---|---|---|---|
| XVII | + | + | + | + | + | + | + | + |
| VIIa | ++ | ++ | ++ | ++ | ++ | ++ | ++ | ++ |
| IV | ++ | − | + | ++ | + | − | + | + |
| XV | ++ | +++ | +++ | +++ | +++ | ++ | +++ | ++ |
| XI | ++ | ++ | ++ | ++ | ++ | ++ | ++ | ++ |
| XVI | +++ | +++ | +++ | +++ | +++ | + | ++ | ++ |
| XII | | | | | | | | |
| XIV | ++ | ++ | ++ | ++ | ++ | − | ++ | ++ |

Section C: Expression of Herbicide-Resistant Protox Genes in Transgenic Plants

Example 19

Engineering of Plants Tolerant to Protox-inhibiting Herbicides by Homologous Recombination or Gene Conversion Because the described mutant coding sequences effectively confer herbicide tolerance when expressed under the control of the native protox promoter, targeted changes to the protox coding sequence in its native chromosomal location represent an alternative means for generating herbicide tolerant plants and plant cells. A fragment of protox DNA containing the desired mutations, but lacking its own expression signals (either promoter or 3′ untranslated region) can be introduced by any of several art-recognized methods (for instance, Agrobacterium transformation, direct gene transfer to protoplasts, microprojectile bombardment), and herbicide-tolerant transformants selected. The introduced DNA fragment also contains a diagnostic restriction enzyme site or other sequence polymorphism that is introduced by site-directed mutagenesis in vitro without changing the encoded amino acid sequence (i.e. a silent mutation). As has been previously reported for various selectable marker and herbicide tolerance genes (see, e.g., Paszkowski et al., *EMBO J.* 7: 4021–4026 (1988); Lee et al., Plant Cell 2: 415–425 (1990); Risseeuw et al., Plant J. 7: 109–119 (1995)). some transformants are found to result from homologous integration of the mutant DNA into the protox chromosomal locus, or from conversion of the native protox chromosomal sequence to the introduced mutant sequence. These transformants are recognized by the combination of their herbicide-tolerant phenotype, and the presence of the diagnostic restriction enzyme site in their protox chromosomal locus.

Example 20

Construction of Plant Transformation Vectors

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra, *Gene* 19:259–268 (1982); Bevan et al., *Nature* 304: 184–187 (1983)), the bar gene, which confers resistance to the herbicide phosphinothricin (White et al., *Nucl Acids Res* 18: 1062 (1990), Spencer et al. *Theor Appl Genet* 79: 625–631(1990)), the hph gene, which confers resistance to the antibiotic hygromycin (Blochinger & Diggelmann, *Mol Cell Biol* 4:2929–2931), and the dhfr gene, which confers resistance to methotrexate (Bourouis et al., *EMBO J.* 2(7) :1099–1104 (1983)).

I. Construction of Vectors Suitable for Agrobacterium Transformation

Many vectors are available for transformation using *Agrobacterium tumefaciens*. These typically carry at least one T-DNA border sequence and include vectors such as pBIN19 (Bevan, *Nucl. Acids Res.* (1984)) and pXYZ. Below the construction of two typical vectors is described.

Construction of pCIB200 and pCIB2001: The binary vectors pCIB200 and pCIB2001 are used for the construction of recombinant vectors for use with Agrobacterium and was constructed in the following manner. pTJS75kan was created by NarI digestion of pTJS75 (Schmidhauser & Helinski, *J Bacteriol.* 164: 446–455 (1985)) allowing excision of the tetracycline-resistance gene, followed by insertion of an AccI fragment from pUC4K carrying an NPTII (Messing & Vierra, *Gene* 19:259–268 (1982); Bevan et al., *Nature* 304: 184–187 (1983); McBride et al., *Plant Molecular Biology* 14:266–276 (1990)). XhoI linkers were ligated to the EcoRV fragment of pCIB7, which contains the left and right T-DNA borders, a plant selectable nos/nptII chimeric gene and the pUC polylinker (Rothstein et al., *Gene* 53: 153–161 (1987)), and the XhoI-digested fragment was cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200, which is created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

Construction of pCIB10 and Hygromycin Selection Derivatives Thereof: The binary vector pCIB10 contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al., *Gene* 53: 153–161 (1987). Various derivatives of pCIB10 have been constructed that incorporate the gene for hygromycin B phosphotransferase described by Gritz et al., *Gene* 25: 179–188 (1983)). These derivatives enable selection of transgenic plant cells on hygromycin only (pCIB743), or hygromycin and kanamycin (pCIB715, pCIB717).

II. Construction of Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above that contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Below, the construction of some typical vectors is described.

Construction of pCIB3064: pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites were mutated using standard PCR techniques in such a way as to remove the ATG's and generate the restriction sites SspI and PvuII. The new restriction sites were 96 and 37 bp away from the unique SalI site and 101 and 42 bp away from the actual start site. The resultant derivative of pCIB246 was designated pCIB3025. The GUS gene was then excised from pCIB3025 by digestion with SalI and SacI, the termini rendered blunt and religated to generate plasmid pCIB3060. The plasmid pJIT82 was obtained from the John Innes Centre, Norwich and the a 400 bp SmaI fragment containing the bar gene from *Streptomyces viridochromogenes* was excised and inserted into the HpaI site of pCIB3060 (Thompson et al. *EMBO J* 6:2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

Construction of pSOG19 and pSOG35: pSOG35 is a transformation vector that utilizes the *E. coli* gene dihydrofolate reductase (DHFR) as a selectable marker conferring resistance to methotrexate. PCR was used to amplify the 35S promoter (~800 bp), intron 6 from the maize Adh1 gene (~550 bp) and 18 bp of the GUS untranslated leader sequence from pSOG10. A 250 bp fragment encoding the *E. coli* dihydrofolate reductase type II gene was also amplified by PCR and these two PCR fragments were assembled with a SacI-PstI fragment from pBI221 (Clontech), which comprised the pUC19 vector backbone and the nopaline synthase terminator. Assembly of these fragments generated pSOG19, which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences.

Example 21

Construction of Plant Expression Cassettes

Gene sequences intended for expression in transgenic plants are firstly assembled in expression cassettes behind a suitable promoter and upstream of a suitable transcription terminator. These expression cassettes can then be easily transferred to the plant transformation vectors described above in Example 20.

I. Promoter Selection

The selection of a promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and this selection will reflect the desired location of expression of the transgene. Alternatively, the selected promoter may drive expression of the gene under a light-induced or other temporally regulated promoter. A further alternative is that the selected promoter be chemically regulated. This would provide the possibility of inducing expression of the transgene only when desired and caused by treatment with a chemical inducer.

II. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator, the pea rbcS E9 terminator, as well as terminators naturally associated with the plant protox gene (i.e. "protox terminators"). These can be used in both monocotyledons and dicotyledons.

III. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183–1200 (1987)). In the same experimental system, the intron from the maize bronze1 gene had a similar effect in enhancing expression (Callis et al., supra). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693–8711 (1987); Skuzeski et al. *Plant Molec. Biol.* 15: 65–79 (1990))

IV. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence that is found at the amino terminal end of various proteins and that is cleaved during chloroplast import yielding the mature protein (e.g. Comai et al. *J. Biol. Chem.* 263: 15104–15109 (1988)). These signal sequences can be fused to heterologous gene products to effect the import of heterologous products into the chloroplast (van den Broeck et al. *Nature* 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins that are known to be chloroplast localized.

Other gene products are localized to other organelles such as the mitochondrion and the peroxisome (e.g. Unger et al. *Plant Molec. Biol.* 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting to cellular protein bodies has been described by Rogers et al., *Proc. Natl. Acad. Sci. USA* 82: 6512–6516 (1985)).

In addition, sequences have been characterized that cause the targeting of gene products to other cell compartments. Amino terminal sequences are responsible for targeting to the ER, the apoplast, and extracellular secretion from aleurone cells (Koehler & Ho, *Plant Cell* 2: 769–783 (1990)). Additionally, amino terminal sequences in conjunction with carboxy terminal sequences are responsible for vacuolar targeting of gene products (Shinshi et al., *Plant Molec. Biol.* 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site and the fusion constructed should take into account any amino acids after the cleavage site that are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) *Methods in Chloroplast Molecular Biology*, Elsevier. pp. 1081–1091 (1982); Wasmann et al. *Mol. Gen. Genet* 205: 446–453 (1986)). These construction techniques are well known in the art and are equally applicable to mitochondria and peroxisomes. The choice of targeting that may be required for expression of the transgenes will depend on the cellular localization of the precursor required as the starting point for a given pathway. This will usually be cytosolic or chloroplastic, although it may is some cases be mitochondrial or peroxisomal. The products of transgene expression will not normally require targeting to the ER, the apoplast or the vacuole.

The above described mechanisms for cellular targeting can be utilized not only in conjunction with their cognate promoters, but also in conjunction with heterologous promoters so as to effect a specific cell targeting goal under the transcriptional regulation of a promoter that has an expression pattern different to that of the promoter from which the targeting signal derives.

Example 22

Transformation of Dicotyledons

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., *EMBO J* 3:2717–2722 (1984), Potrykus et al., *Mol. Gen. Genet.* 199: 169–177 (1985), Reich et al., *Biotechnology* 4: 1001–1004 (1986), and Klein et al., *Nature* 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. The many crop species that are routinely transformable by Agrobacterium include tobacco, tomato, sunflower, cotton, oilseed rape, potato, soybean, alfalfa and poplar (EP 0 317 511 (cotton), EP 0 249 432 (tomato, to Calgene), WO 87/07299 (Brassica, to Calgene), U.S. Pat. No. 4,795,855 (poplar)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Example 23

Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. *Biotechnology* 4: 1093–1096 (1986)).

Patent Applications EP 0 292 435 (to Ciba-Geigy), EP 0 392 225 (to Ciba-Geigy) and WO 93107278 (to Ciba-Geigy) describe techniques for the preparation of callus and protoplasts from an elite inbred line of maize, transformation of protoplasts using PEG or electroporation, and the regeneration of maize plants from transformed protoplasts. Gordon-Kamm et al., *Plant Cell* 2: 603–618 (1990)) and Fromm et al., *Biotechnology* 8: 833–839 (1990)) have published techniques for transformation of A188-derived maize line using particle bombardment. Furthermore, application WO 93/07278 (to Ciba-Geigy) and Koziel et al., *Biotechnology* 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediate transformation has been described for Japonica-types and Indica-types (Zhang et al., *Plant Cell Rep* 7: 379–384 (1988); Shimamoto et al. *Nature* 338:274–277 (1989); Datta et al. *Biotechnology* 8: 736–740 (1990)). Both types are also routinely transformable using particle bombardment (Christou et al. *Biotechnology* 9: 957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation was been described by Vasil et al., *Biotechnology* 10: 667–674 (1992)) using particle bombardment into cells of type C long-term regenerable callus, and also by Vasil et al., *Biotechnology* 11: 1553–1558 (1993)) and Weeks et al., *Plant Physiol.* 102: 1077–1084 (1993) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashige & Skoog, *Physiologia Plantarum* 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics, helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" that contained half-strength MS, 2% sucrose, and the same concentration of selection agent. Patent application WO 94/13822 describes methods for wheat transformation and is hereby incorporated by reference.

Example 24

Isolation of the Arabidopsis thaliana Protox-1 Promoter Sequence

A Lambda Zap II genomic DNA library prepared from *Arabidopsis thaliana* (Columbia, whole plant) was purchased from Stratagene. Approximately 125,000 phage were plated at a density of 25,000 pfu per 15 cm Petri dish and duplicate lifts were made onto Colony/Plaque Screen membranes (NEN Dupont). The plaque lifts were probed with the Arabidopsis Protox-1 cDNA (SEQ ID NO:1 labeled with 32P-dCTP by the random priming method (Life Technologies). Hybridization and wash conditions were at 65° C. as described in Church and Gilbert, *Proc. Natl. Acad. Sci. USA* 81: 1991–1995 (1984). Positively hybridizing plaques were purified and in vivo excised into pBluescript plasmids. Sequence from the genomic DNA inserts was determined by the chain termination method using dideoxy terminators labeled with fluorescent dyes (Applied Biosystems, Inc.). One clone, AraPT1Pro, was determined to contain 580 bp of Arabidopsis sequence upstream from the initiating methionine (ATG) of the Protox-1 protein coding sequence. This clone also contains coding sequence and introns that extend to bp 1241 of the Protox-1 cDNA sequence. The 580 bp 5' noncoding fragment is the putative Arabidopsis Protox-1 promoter, and the sequence is set forth in SEQ ID NO:13.

AraPt1Pro was deposited Dec. 15, 1995, as pWDC-11 (NRRL #B-21515)

Example 25

Construction of Plant Transformation Vectors Expressing Altered Protox-1 Genes Behind the Native Arabidopsis Protox-1 Promoter A full-length cDNA of the appropriate altered Arabidopsis Protox-1 cDNA was isolated as an EcoRI-XhoI partial digest fragment and cloned into the plant expression vector pCGN1761ENX (see Example 9 of International application no. PCT/IB95/00452 filed Jun. 8, 1995, published Dec. 21, 1995 as WO 95/34659). This plasmid was digested with NcoI and BamHI to produce a fragment comprised of the complete Protox-1 cDNA plus a transcription terminator from the 3' untranslated sequence of the tml gene of *Agrobacterium tumefaciens*. The AraPT1Pro plasmid described above was digested with NcoI and BamHI to produce a fragment comprised of pBluescript and the 580 bp putative Arabidopsis Protox-1 promoter. Ligation of these two fragments produced a fusion of the altered protox cDNA to the native protox promoter. The expression cassette containing the Protox-1 promoter/Protox-1 cDNA/tml terminator fusion was excised by digestion with KpnI and cloned into the binary vector pCIB200. The binary plasmid was transformed by electroporation into Agrobacterium and then into Arabidopsis using the vacuum infiltration method (Bechtold et al., C.R. *Acad. Sci. Paris* 316: 1194–1199 (1993). Transformants expressing altered protox genes were selected on kanamycin or on various concentrations of protox inhibiting herbicide.

Example 26

Production of Herbicide Tolerant Plants by Expression of a Native Protox-1 Promoter/Altered Protox-1 Fusion Using the procedure described above, an Arabidopsis Protox-1 cDNA containing a TAC to ATG (Tyrosine to Methionine) change at nucleotides 1306–1308 in the Protox-1 sequence (SEQ ID NO:1) was fused to the native Protox-1 promoter fragment and transformed into *Arabidopsis thaliana*. This altered Protox-1 enzyme (AraC-2Met) has been shown to be >10-fold more tolerant to various protox-inhibiting herbicides than the naturally occurring enzyme when tested in the previously described bacterial expression system. Seed from the vacuum infiltrated plants was collected and plated on a range (10.0 nM–1.0 uM) of a protox inhibitory aryluracil herbicide of formula XVII. Multiple experiments with wild type Arabidopsis have shown that a 10.0 nM concentration of this compound is sufficient to prevent normal seedling germination. Transgenic seeds expressing the AraC-2Met altered enzyme fused to the native Protox-1 promoter produced normal Arabidopsis seedlings at herbicide concentrations up to 500 nM, indicating at least 50-fold higher herbicide tolerance when compared to wild-type Arabidopsis. This promoter/altered protox enzyme fusion therefore functions as an effective selectable marker for plant transformation. Several of the plants that germinated on 100.0 nM of protox-inhibiting herbicide were transplanted to soil, grown 2–3 weeks, and tested in a spray assay with various concentrations of the protox-inhibiting herbicide. When compared to empty vector control transformants, the AraPT1Pro/AraC-2Met transgenics were >10-fold more tolerant to the herbicide spray.

Example 27

Demonstration of resistant mutations' cross-tolerance to various protox-inhibiting compounds in an Arabidopsis germination assay.

Using the procedure described above, an Arabidopsis Protox-1 cDNA containing both a TAC to ATC (tyrosine to isoleucine) change at nucleotides 1306–1308 and a TCA to TTA (serine to leucine) change at nucleotides 945–947 in the Protox-1 sequence (SEQ ID NO:1) was fused to the native Protox-1 promoter fragment and transformed into *Arabidopsis thaliana*. This altered Protox-1 enzyme (AraC-2Ile+ AraC305Leu) has been shown to be >10-fold more tolerant to a protox inhibitory aryluracil herbicide of formula XVII than the naturally occurring enzyme when tested in a bacterial system (see Examples 8–12). Homozygous Arabidopsis lines containing this fusion were generated from transformants that showed high tolerance to a protox inhibiting herbicide in a seedling germination assay as described above. The seed from one line was tested for cross-tolerance to various protox-inhibitory compounds by repeating the germination assay on concentrations of the compounds that had been shown to inhibit germination of wild-type Arabidopsis. The results from these experiments are shown in Table 4.

TABLE 4

Cross Tolerance to Various Protox Inhibitors in a Seed Germination Assay

| Formula | Common name | Tolerance |
| --- | --- | --- |
| II | acifluorofen | + |
| III | fomasafen | + |
| IV | fluoroglycofen | ± |
| IVb | bifenox | + |
| IVc | oxyfluorofen | + |
| IVd | lactofen | ± |
| VIIa | fluthiacet-methyl | ++ |
| X | sulfentrazone | + |
| XI | flupropazil | ++ |

TABLE 4-continued

Cross Tolerance to Various Protox Inhibitors in a Seed Germination Assay

| Formula | Common name | Tolerance |
| --- | --- | --- |
| XIV | flumiclorac | + |
| XVI | flumioxazin | +++ |
| XVII | | ++ |
| XXIa | BAY 11340 | + |
| XXII | | ++ |

± ≦ 10 × more tolerant than wt
+ ≧ 10 × more tolerant than wt
++ ≧ 100 × more tolerant than wt
+++ ≧ 1000 × more tolerant than wt Example 28

Isolation of a Maize Protox-1 Promoter Sequence

A Zea Mays (Missouri 17 inbred, etiolated seedlings) genomic DNA library in the Lambda FIX II vector was purchased from Stratagene. Approximately 250,000 pfu of the library was plated at a density of 50,000 phage per 15 cm plate and duplicate lifts were made onto Colony/Plaque screen membranes (NEN Dupont). The plaque lifts were probed with the maize Protox-1 cDNA (SEQ ID NO:5) labeled with 32P-dCTP by the random priming method (Life Technologies). Hybridization and wash conditions were at 65° C. as described in Church and Gilbert, *Proc. Natl. Acad. Sci. USA* 81: 1991–1995 (1984). Lambda phage DNA was isolated from three positively hybridizing phage using the Wizard Lambda Preps DNA Purification System (Promega). Analysis by restriction digest, hybridization patterns, and DNA sequence analysis identified a lambda clone containing approximately 3.5 kb of maize genomic DNA located 5' to the maize Protox-1 coding sequence previously isolated as a cDNA clone. This fragment includes the maize Protox-1 promoter. The sequence of this fragment is set forth in SEQ ID NO:14. From nucleotide 1 to 3532, this sequence is comprised of 5' noncoding sequence. From nucleotide 3533 to 3848, this sequence encodes the 5' end of the maize Protox-1 protein.

A plasmid containing the sequence of SEQ ID NO:14 fused to the remainder of the maize Protox-1 coding sequence was deposited Mar. 19, 1996 as pWDC-14 (NRRL #B-21546).

Example 29

Construction of Plant Transformation Vectors Expressing Altered Protox-1 Genes Behind the Native Maize Protox-1 Promoter The 3848 bp maize genomic fragment (SEQ ID NO:14) was excised from the isolated lambda phage clone as a SalI-KpnI partial digest product and ligated to a KpnI-NotI fragment derived from an altered maize Protox-1 cDNA that contained an alanine to leucine change at amino acid 164 (SEQ ID NO:6). This created a fusion of the native maize Protox-1 promoter to a full length cDNA that had been shown to confer herbicide tolerance in a bacterial system (Examples 8–13). This fusion was cloned into a pUC18 derived vector containing the CaMV 35S terminator sequence to create a protox promoter/altered protox cDNA/terminator cassette. The plasmid containing this cassette was designated pWCo-1.

A second construct for maize transformation was created by engineering the first intron found in the coding sequence from the maize genomic clone back into the maize cDNA. The insertion was made using standard overlapping PCR fusion techniques. The intron (SEQ ID NO:25) was 93 bp long and was inserted between nucleotides 203 and 204 of SEQ ID NO:6, exactly as it appeared in natural context in the lambda clone described in Example 28. This intron-containing version of the expression cassette was designated pWCo-2.

Example 30

Demonstration of Maize Protox-1 Promoter Activity in Transgenic Maize Plants

Maize plants transformed with maize protox promoter/altered protox fusions were identified using PCR analysis with primers specific for the transgene. Total RNA was prepared from the PCR positive plants and reverse-transcribed using Superscript M-MLV (Life Technologies) under recommended conditions. Two microliters of the reverse transcription reaction was used in a PCR reaction designed to be specific for the altered protox sequence. While untransformed controls give no product in this reaction, approximately 85% of plants transformed with pWCo-1 gave a positive result, indicating the presence of mRNA derived from the transgene. This demonstrates some level of activity for the maize protox promoter. The RNA's from the transgenic maize plants were also subjected to standard northern blot analysis using the radiolabeled maize protox cDNA fragment from SEQ ID NO:6 as a probe. Protox-1 mRNA levels significantly above those of untransformed controls were detected in some of the transgenic maize plants. This elevated mRNA level is presumed to be due to expression of altered protox-1 mRNA from the cloned maize protox promoter.

Example 31

Isolation of a Sugar Beet Protox-1 Promoter Sequence

A genomic sugar beet library was prepared by Stratagene in the Lambda Fix II vector. Approximately 300,000 pfu of the library was plated and probed with the sugar beet protox-1 cDNA sequence (SEQ ID NO:17) as described for maize in Example 28. Analysis by restriction digest, hybridization patterns and DNA sequence analysis identified a lambda clone containing approximately 7 kb of sugar beet genomic DNA located 5' to the sugar beet coding sequence previously isolated as a cDNA clone. A PstI-SalI fragment of 2606 bb was subcloned from the lambda clone into a pBluescript vector. This fragment contains 2068 bp of 5' noncoding sequence and includes the sugar beet protox-1 promoter sequence. It also includes the first 453 bp of the protox-1 coding sequence and the 85 bp first intron contained in the coding sequence. The sequence of this fragment is set forth in SEQ ID NO:26.

A plasmid containing the sequence of SEQ ID NO:26 was deposited Dec. 6, 1996 as pWDC-20 (NRRL #B-21650).

Example 32

Construction of Plant Transformation Vectors Expressing Altered Sugar Beet Protox-1 Genes Behind the Native Sugar Beet Protox-1 Promoter The sugar beet genomic fragment (SEQ ID NO:26) was excised from the genomic subclone described in Example 31 as a SacI-BsrGI fragment that includes 2068 bp of 5' noncoding sequence and the first 300 bp of the sugar beet Protox-1 coding sequence. This fragment was ligated to a BsrGI-NotI fragment derived from an altered sugar beet Protox-1 cDNA that contained a tyrosine to methionine change at amino acid 449 (SEQ ID NO:18). This created a fusion of the native sugar beet Protox-1 promoter to a full length cDNA that had been shown to confer herbicide tolerance in a bacterial system (Examples 8–13). This fusion was cloned into a pUC18 derived vector containing the CaMV 35S terminator sequence to create a protox promoter/altered protox cDNA/terminator cassette. The plasmid containing this cassette was designated pWCo-3.

Example 33

Production of Herbicide Tolerant Plants by Expression of a Native Sugar Beet Protox-1 Promoter/Altered Sugar Beet Protox-1 Fusion The expression cassette from pWCo-3 is transformed into sugar beet using any of the transformation methods applicable to dicot plants, including Agrobacterium, protoplast, and biolistic transformation techniques. Transgenic sugar beets expressing the altered protox-1 enzyme are identified by RNA-PCR and tested for tolerance to protox-inhibiting herbicides at concentrations that are lethal to untransformed sugar beets.

Section D: Expression of Protox Genes in Plant Plastids

Example 34

Preparation of a Chimeric Gene Containing the Tobacco Plastid cIpP Gene Promoter and Native cIpP 5' Untranslated Sequence Fused to a GUS Reporter Gene and Plastid rps16 Gene 3' Untranslated Sequence in a Plastid Transformation Vector I. Amplification of the Tobacco Plastid cIpP Gene Promoter and Complete 5' Untranslated RNA (5' UTR).

Total DNA from *N. tabacum* c.v. "Xanthi NC" was used as the template for PCR with a left-to-right "top strand" primer comprising an introduced EcoRI restriction site at position-197 relative to the ATG start codon of the constitutively expressed plastid cIpP gene (primer PcIp_P1a: 5'-gcggaattcatacttatttatcattagaaag-3' (SEQ ID NO:27); EcoRI restriction site underlined) and a right-to-left "bottom strand" primer homologous to the region from −21 to −1 relative to the ATG start codon of the cIpP promoter that incorporates an introduced NcoI restriction site at the start of translation (primer PcIp_P2b: 5'-gcggaattcatacttatttatcattagaaag-3' (SEQ ID NO:28); NcoI restriction site underlined). This PCR reaction was undertaken with Pfu thermostable DNA polymerase (Stratagene, La Jolla, Calif.) in a Perkin Elmer Thermal Cycler 480 according to the manufacturer's recommendations (Perkin Elmer/Roche, Branchburg, N.J.) as follows: 7 min 95° C., followed by 4 cycles of 1 min 95° C./2 min 43° C./1 min 72° C., then 25 cycles of 1 min 95° C./2 min 55° C./1 min 72° C. The 213 bp amplification product comprising the promoter and 5' untranslated region of the cIpP gene containing an EcoRI site at its left end and an NcoI site at its right end and corresponding to nucleotides 74700 to 74505 of the *N. tabacum* plastid DNA sequence (Shinozaki et al., *EMBO J.* 5:2043–2049 (1986)) was gel purified using standard procedures and digested with EcoRI and NcoI (all restriction enzymes were purchased from New England Biolabs, Beverly, Mass.).

II. Amplification of the Tobacco Plastid rps16 Gene 3' Untranslated RNA Sequence (3'UTR).

Total DNA from *N. tabacum* c.v. "Xanthi NC" was used as the template for PCR as described above with a left-to-right "top strand" primer comprising an introduced XbaI restriction site immediately following the TAA stop codon of the plastid rps16 gene encoding ribosomal protein S16 (primer rps16P_1a (5'-GCG TCTAGATCAACCGAAATTCAATTAAGG-3' (SEQ ID NO:30); XbaI restriction site underlined) and a right-to-left "bottom strand" primer homologous to the region from +134 to +151 relative to the TAA stop codon of rps16 that incorporates an introduced HindIII restriction site at the 3' end of the rps16 3' UTR (primer rps16P_1b (5'-CGC AAGCTTCAATGGAAGCAATGATAA-3' (SEQ ID NO:31); HindIII restriction site underlined). The 169 bp amplification product comprising the 3' untranslated region of the rps16 gene containing an XbaI site at its left end and a HindIII site at its right end and containing the region corresponding to nucleotides 4943 to 5093 of the *N. tabacum* plastid DNA sequence (Shinozaki et al., 1986) was gel purified and digested with XbaI and HindIII.

III. Ligation of a GUS Reporter Gene Fragment to the cIpP Gene Promoter and 5' and 3' UTR's An 1864 bp b-galacturonidase (GUS) reporter gene fragment derived from plasmid pRAJ275 (Clontech) containing an NcoI restriction site at the ATG start codon and an XbaI site following the native 3' UTR was produced by digestion with NcoI and XbaI. This fragment was ligated in a four-way reaction to the 201 bp EcoRI/NcoI cIpP promoter fragment, the 157 bp XbaI/HindIII rps16 3'UTR fragment, and a 3148 bp EcoRI/HindIII fragment from cloning vector pGEM3Zf (−) (Promega, Madison Wis.) to construct plasmid pPH138. Plastid transformation vector pPH140 was constructed by digesting plasmid pPRV111a (Zoubenko et al. 1994) with EcoRI and HindIII and ligating the resulting 7287 bp fragment to a 2222 bp EcoRI/HindIII fragment of pPH138.

Example 35

Preparation of a Chimeric Gene Containing the Tobacco Plastid cIpP Gene Promoter Plus Tobacco Plastid psbA Gene Minimal 5' Untranslated Sequence Fused to a GUS Reporter Gene and Plastid rps16 Gene 3' Untranslated Sequence in a Plastid Transformation Vector Amplification of the tobacco plastid cIpP gene promoter and truncated 5' untranslated RNA (5' UTR): Total DNA from *N. tabacum* c.v. "Xanthi NC" was used as the template for PCR as described above with the left-to-right "top strand" primer PcIp_P1a (SEQ ID NO:27) and a right-to-left "bottom strand" primer homologous to the region from −34 to −11 relative to the ATG start codon of the cIpP promoter that incorporates an introduced XbaI restriction site in the cIpP 5' UTR at position −11 (primer PcIp_P1b: 5'-gcgtctagaaagaactaaatactatatttcac-3' (SEQ ID NO:29); XbaI restriction site underlined). The 202 bp amplification product comprising the promoter and truncated 5' UTR of the cIpP gene containing an EcoRI site at its left end and an XbaI site at its right end was gel purified and digested with XbaI. The XbaI site was subsequently filled in with Klenow DNA polymerase (New England Biolabs) and the fragment digested with EcoRI. This was ligated in a five-way reaction to a double stranded DNA fragment corresponding to the final 38 nucleotides and ATG start codon of the tobacco plastid psbA gene 5' UTR (with an NcoI restriction site overhang introduced into the ATG start codon) that was created by annealing the synthetic oligonucleotides minpsb_U (top strand: 5'-gggagtccctgatgattaaataaaccaagattttac-3' (SEQ ID NO:32)) and minpsb_L (bottom strand: 5'-catggtaaaatcttggtttatttaatcatcagggactccc-3' (SEQ ID NO:33); NcoI restriction site 5' overhang underlined), the NcoI/XbaI GUS reporter gene fragment described above, the XbaI/HindIII rps16 3'UTR fragment described above, and the EcoRI/HindIII pGEM3Zf(−) fragment described above to construct plasmid pPH139. Plastid transformation vector pPH144 was constructed by digesting plasmid pPRV111a (Zoubenko, et al., *Nucleic Acids Res* 22: 3819–3824 (1994)) with EcoRI and HindIII and ligating the resulting 7287 bp fragment to a 2251 bp EcoRI/HindIII fragment of pPH139.

Example 36

Preparation of a Chimeric Gene Containing the Tobacco Plastid cIpP Gene Promoter and Complete 5' Untranslated Sequence Fused to the *Arabidopsis thaliana* Protox-1 Coding Sequence and Plastid rps16 Gene 3' Untranslated Sequence in a Vector for Tobacco Plastid Transformation Miniprep DNA from plasmid AraC-2Met carrying an *Arabidopsis thaliana* NotI insert that includes cDNA sequences from the Protoporphyrinogen IX Oxidase ("PROTOX") gene encoding a portion of the amino terminal plastid transit peptide, the full-length cDNA and a portion of the 3' untranslated region was used as the template for PCR as described above using a left-to-right "top strand" primer (with homology to nucleotides +172 to +194 relative to the ATG start codon of the full length precursor protein) comprising an introduced NcoI restriction site and new ATG start codon at the deduced start of the mature PROTOX protein coding sequence (primer APRTXP1a: 5'-GGGA CCATGGATTGTGTGATTGTCGGCGGAGG-3' (SEQ ID NO:34); NcoI restriction site underlined) and a right-to-left "bottom strand" primer homologous to nucleotides +917 to +940 relative to the native ATG start codon of the PROTOX precursor protein (primer APRTXP1b: 5'-CTCCGCTCTCCAGCTTAGTGATAC-3' (SEQ ID NO:35)). The 778 bp product was digested with NcoI and SfuI and the resulting 682 bp fragment ligated to an 844 bp SfuI/NotI DNA fragment of AraC-2Met comprising the 3' portion of the PROTOX coding sequence and a 2978 bp NcoI/NotI fragment of the cloning vector pGEM5Zf(+) (Promega, Madison Wis.) to construct plasmid pPH141. Plastid transformation vector pPH143 containing the cIpP promoter driving the 276'854-resistance SV1-Met PRO-TOX gene with the rps16 3' UTR was constructed by digesting pPH141 with NcoI and SspI and isolating the 1491 bp fragment containing the complete PROTOX coding sequence, digesting the rps16P_1a and rps16P_1b PCR product described above with HindIII, and ligating these to a 7436 bp NcoI/HindIII fragment of pPH140.

Example 37

Preparation of a Chimeric Gene Containing the Tobacco Plastid cIpP Gene Promoter Plus Tobacco Plastid psbA Gene Minimal 5' Untranslated Sequence Fused to the *Arabidopsis thaliana* Protox-1 Coding Sequence and Plastid rps16 Gene 3' Untranslated Sequence in a Vector for Tobacco Plastid Transformation Plastid transformation vector pPH145 containing the cIpP promoter/psbA 5' UTR fusion driving the 276'854- resistance SV1-Met PROTOX gene with the rps16 3' UTR was constructed by digesting pPH141 with NcoI and SspI and isolating the 1491 bp fragment containing the complete PROTOX coding sequence, digesting the rps16P__1a and rps16P__1b PCR product described above with HindIII, and ligating these to a 7465 bp NcoI/HindIII fragment of pPH144.

Example 38

Biolistic Transformation of the Tobacco Plastid Genome

Seeds of *Nicotiana tabacum* c.v. 'Xanthi nc' were germinated seven per plate in a 1" circular array on T agar medium and bombarded 12–14 days after sowing with 1 μm tungsten particles (M10, Biorad, Hercules, Calif.) coated with DNA from plasmids pPH143 and pPH145 essentially as described (Svab, Z. and Maliga, P. (1993) *PNAS* 90, 913–917). Bombarded seedlings were incubated on T medium for two days after which leaves were excised and placed abaxial side up in bright light (350–500 μmol photons/m$^2$/s) on plates of RMOP medium (Svab, Z., Hajdukiewicz, P. and Maliga, P. (1990) *PNAS* 87, 8526–8530) containing 500 μg/ml spectinomycin dihydrochloride (Sigma, St. Louis, Mo.). Resistant shoots appearing underneath the bleached leaves three to eight weeks after bombardment were subcloned onto the same selective medium, allowed to form callus, and secondary shoots isolated and subcloned. Complete segregation of transformed plastid genome copies (homoplasmicity) in independent subclones was assessed by standard techniques of Southern blotting (Sambrook et al., (1989) *Molecular Cloning: A Laboratory Manual*, Cold Spring Harbor Laboratory, Cold Spring Harbor). BamHI/EcoRI-digested total cellular DNA (Mettler, I. J. (1987) *Plant Mol Biol Reporter* 5, 346–349) was separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) *PNAS* 91, 7301–7305) and transferred to the greenhouse.

Various modifications of the invention described herein will become apparent to those skilled in the art. Such modifications are intended to fall within the scope of the appended claims.

What is claimed is:

1. A modified plant DNA molecule encoding a modified enzyme having protoporphyrinogen oxidase activity, wherein said modified enzyme has at least one amino acid modification compared to a naturally occurring protox enzyme, wherein said at least one amino acid modification confers resistance to an inhibitor of the naturally occurring protox enzyme, and wherein said at least one amino acid modification comprises an amino acid substitution occurring at a position corresponding to position 240, 245, 246, 388, 390, 451, 455, 500, or 536 of the comparative alignment shown in Table 1.

2. A DNA molecule according to claim 1, wherein said amino acid substitution occurs at a position corresponding to position 240 of the comparative alignment shown in Table 1.

3. A DNA molecule according to claim 2, wherein a cysteine occurring at the position corresponding to position 240 of the comparative alignment shown in Table 1 is replaced with phenylalanine, leucine, or lysine.

4. A DNA molecule according to claim 1, wherein said amino acid substitution occurs at a position corresponding to position 245 of the comparative alignment shown in Table 1.

5. A DNA molecule according to claim 4, wherein an alanine occurring at the position corresponding to position 245 of the comparative alignment shown in Table 1 is replaced with valine, threonine, leucine, cysteine, or isoleucine.

6. A DNA molecule according to claim 1, wherein said amino acid substitution occurs at a position corresponding to position 246 of the comparative alignment shown in Table 1.

7. A DNA molecule according to claim 6, wherein a glycine occurring at the position corresponding to position 246 of the comparative alignment shown in Table 1 is replaced with serine or leucine.

8. A DNA molecule according to claim 1, wherein said amino acid substitution occurs at a position corresponding to position 388 of the comparative alignment shown in Table 1.

9. A DNA molecule according to claim 8, wherein a proline occurring at the position corresponding to position 388 of the comparative alignment shown in Table 1 is replaced with serine or histidine.

10. A DNA molecule according to claim 1, wherein said amino acid substitution occurs at a position corresponding to position 390 of the comparative alignment shown in Table 1.

11. A DNA molecule according to claim 10, wherein a valine occurring at the position corresponding to position 390 of the comparative alignment shown in Table 1 is replaced with leucine.

12. A DNA molecule according to claim 1, wherein said amino acid substitution occurs at a position corresponding to position 451 of the comparative alignment shown in Table 1.

13. A DNA molecule according to claim 12, wherein a tyrosine occurring at the position corresponding to position 451 of the comparative alignment shown in Table 1 is replaced with cysteine, isoleucine, leucine, threonine, methionine, valine, alanine, or arginine.

14. A DNA molecule according to claim 1, wherein said amino acid substitution occurs at a position corresponding to position 455 of the comparative alignment shown in Table 1.

15. A DNA molecule according to claim 14, wherein an amino acid occurring at the position corresponding to position 455 of the comparative alignment shown in Table 1 is replaced with proline.

16. A DNA molecule according to claim 1, wherein said amino acid substitution occurs at a position corresponding to position 500 of the comparative alignment shown in Table 1.

17. A DNA molecule according to claim 16, wherein an isoleucine occurring at the position corresponding to position 500 of the comparative alignment shown in Table 1 is replaced with threonine, histidine, glycine, or asparagine.

18. A DNA molecule according to claim 1, wherein said amino acid substitution occurs at a position corresponding to position 536 of the comparative alignment shown in Table 1.

19. A DNA molecule according to claim 18, wherein a valine occurring at the position corresponding to position 536 of the comparative alignment shown in Table 1 is replaced with alanine.

20. A DNA molecule according to claim 1, wherein said at least one amino acid modification further comprises an additional amino acid substitution occuring at a position corresponding to position 143, 274, 330, 450, or 523 of the comparative alignment shown in Table 1.

21. A DNA molecule according to claim 1, wherein said at least one amino acid modification comprises an amino acid substitution occurring at a position corresponding to position 245 or 451 of the comparative alignment shown in Table 1 and an additional amino acid substitution occurring at a position corresponding to position 143, 274, 330, 450, or 523 of the comparative alignment shown in Table 1.

22. A DNA molecule according to claim 21, wherein a proline occurring at the position corresponding to position 143 of the comparative alignment shown in Table 1 is replaced with leucine.

23. A DNA molecule according to claim 21, wherein an amino acid occurring at the position corresponding to position 274 of the comparative alignment shown in Table 1 is replaced with isoleucine or alanine.

24. A DNA molecule according to claim 21, wherein an amino acid occurring at the position corresponding to position 330 of the comparative alignment shown in Table 1 is replaced with leucine.

25. A DNA molecule according to claim 21, wherein an amino acid occurring at the position corresponding to position 450 of the comparative alignment shown in Table 1 is replaced with serine.

26. A DNA molecule according to claim 21, wherein an amino acid occurring at the position corresponding to position 523 of the comparative alignment shown in Table 1 is replaced with cysteine.

27. A DNA molecule according to claim 1, wherein said DNA molecule is isolated from a plant selected from the group consisting of: Arabidopsis, maize, wheat, soybean, cotton, sugar beet, rape, rice, and sorghum.

28. A DNA molecule according to claim 27, wherein said DNA molecule is isolated from Arabidopsis and wherein said amino acid substitution occurs at a position corresponding to position 215, 220, 221, 363, 365, 426, 430, 475, or 511 of SEQ ID NO:2.

29. A DNA molecule according to claim 28, wherein a cysteine occurring at the position corresponding to position 215 of SEQ ID NO:2 is replaced with phenylalanine, leucine, or lysine.

30. A DNA molecule according to claim 28, wherein an alanine occurring at the position corresponding to position 220 of SEQ ID NO:2 is replaced with valine, threonine, leucine, cysteine, or isoleucine.

31. A DNA molecule according to claim 28, wherein a glycine occurring at the position corresponding to position 221 of SEQ ID NO:2 is replaced with serine or leucine.

32. A DNA molecule according to claim 28, wherein a proline occurring at the position corresponding to position 363 of SEQ ID NO:2 is replaced with serine or histidine.

33. A DNA molecule according to claim 28, wherein a valine occurring at the position corresponding to position 365 of SEQ ID NO:2 is replaced with leucine.

34. A DNA molecule according to claim 28, wherein a tyrosine occurring at the position corresponding to position 426 of SEQ ID NO:2 is replaced with cysteine, isoleucine, leucine, threonine, methionine, valine, alanine, or arginine.

35. A DNA molecule according to claim 28, wherein a serine occurring at the position corresponding to position 430 of SEQ ID NO:2 is replaced with proline.

36. A DNA molecule according to claim 28, wherein a isoleucine occurring at the position corresponding to position 475 of SEQ ID NO:2 is replaced with threonine, histidine, glycine, or asparagine.

37. A DNA molecule according to claim 28, wherein a valine occurring at the position corresponding to position 511 of SEQ ID NO:2 is replaced with alanine.

38. A DNA molecule according to claim 28, wherein said at least one amino acid modification further comprises an additional amino acid substitution occuring at a position corresponding to position 118, 249, 305, 425, or 498 of SEQ ID NO:2.

39. A DNA molecule according to claim 28, wherein said at least one amino acid modification comprises an amino acid substitution occurring at a position corresponding to position 220 or 426 of SEQ ID NO:2 and an additional amino acid substitution occurring at a position corresponding to position 118, 249, 305, 425, or 498 of SEQ ID NO:2.

40. A DNA molecule according to claim 39, wherein a proline occurring at the position corresponding to position 118 of SEQ ID NO:2 is replaced with leucine.

41. A DNA molecule according to claim 39, wherein a threonine occurring at the position corresponding to position 249 of SEQ ID NO:2 is replaced with isoleucine or alanine.

42. A DNA molecule according to claim 39, wherein a serine occurring at the position corresponding to position 305 of SEQ ID NO:2 is replaced with leucine.

43. A DNA molecule according to claim 39, wherein an asparagine occurring at the position corresponding to position 425 of SEQ ID NO:2 is replaced with serine.

44. A DNA molecule according to claim 39, wherein a tyrosine occurring at the position corresponding to position 498 of SEQ ID NO:2 is replaced with cysteine.

45. A DNA molecule according to claim 27, wherein said DNA molecule is isolated from maize and wherein said amino acid substitution occurs at a position corresponding to position 159, 164, 165, 307, 309, 370, 374, 419, or 455 of SEQ ID NO:6.

46. A DNA molecule according to claim 45, wherein a cysteine occurring at the position corresponding to position 159 of SEQ ID NO:6 is replaced with phenylalanine, leucine, or lysine.

47. A DNA molecule according to claim 45, an alanine occurring at the position corresponding to position 164 of SEQ ID NO:6 is replaced with valine, threonine, leucine, cysteine, or isoleucine.

48. A DNA molecule according to claim 45, wherein a glycine occurring at the position corresponding to position 165 of SEQ ID NO:6 is replaced with serine or leucine.

49. A DNA molecule according to claim 45, wherein a proline occurring at the position corresponding to position 307 of SEQ ID NO:6 is replaced with serine or histidine.

50. A DNA molecule according to claim 45, wherein a valine occurring at the position corresponding to position 309 of SEQ ID NO:6 is replaced with leucine.

51. A DNA molecule according to claim 45, wherein a tyrosine occurring at the position corresponding to position 370 of SEQ ID NO:6 is replaced with cysteine, isoleucine, leucine, threonine, methionine, valine, alanine, or arginine.

52. A DNA molecule according to claim 45, wherein an alanine occurring at the position corresponding to position 374 of SEQ ID NO:6 is replaced with proline.

53. A DNA molecule according to claim 45, wherein a isoleucine occurring at the position corresponding to position 419 of SEQ ID NO:6 is replaced with threonine, histidine, glycine, or asparagine.

54. A DNA molecule according to claim 45, wherein a valine occurring at the position corresponding to position 455 of SEQ ID NO:6 is replaced with alanine.

55. A DNA molecule according to claim 27, wherein said DNA molecule is isolated from wheat and wherein said amino acid substitution occurs at a position corresponding to position 206, 211, 212, 354, 356, 417, 421, 466, or 502 of SEQ ID NO:10.

56. A DNA molecule according to claim 55, wherein a cysteine occurring at the position corresponding to position 206 of SEQ ID NO:10 is replaced with phenylalanine, leucine, or lysine.

57. A DNA molecule according to claim 55, wherein an alanine occurring at the position corresponding to position 211 of SEQ ID NO:10 is replaced with valine, threonine, leucine, cysteine, or isoleucine.

58. A DNA molecule according to claim 55, wherein a glycine occurring at the position corresponding to position 212 of SEQ ID NO:10 is replaced with serine or leucine.

59. A DNA molecule according to claim 55, wherein a proline occurring at the position corresponding to position 354 of SEQ ID NO:10 is replaced with serine or histidine.

60. A DNA molecule according to claim 55, wherein a valine occurring at the position corresponding to position 356 of SEQ ID NO:10 is replaced with leucine.

61. A DNA molecule according to claim 55, wherein a tyrosine occurring at the position corresponding to position 417 of SEQ ID NO:10 is replaced with cysteine, isoleucine, leucine, threonine, methionine, valine, alanine, or arginine.

62. A DNA molecule according to claim 55, wherein a serine occurring at the position corresponding to position 421 of SEQ ID NO:10 is replaced with proline.

63. A DNA molecule according to claim 55, wherein a isoleucine occurring at the position corresponding to position 466 of SEQ ID NO:10 is replaced with threonine, histidine, glycine, or asparagine.

64. A DNA molecule according to claim 55, wherein a valine occurring at the position corresponding to position 502 of SEQ ID NO:10 is replaced with alanine.

65. A DNA molecule according to claim 27, wherein said DNA molecule is isolated from soybean and wherein said amino acid substitution occurs at a position corresponding to position 221, 226, 227, 369, 371, 432, 436, 481, or 517 of SEQ ID NO:12.

66. A DNA molecule according to claim 65, wherein a cysteine occurring at the position corresponding to position 221 of SEQ ID NO:12 is replaced with phenylalanine, leucine, or lysine.

67. A DNA molecule according to claim 65, an alanine occurring at the position corresponding to position 226 of SEQ ID NO:12 is replaced with valine, threonine, leucine, cysteine, or isoleucine.

68. A DNA molecule according to claim 65, wherein a glycine occurring at the position corresponding to position 227 of SEQ ID NO:12 is replaced with serine or leucine.

69. A DNA molecule according to claim 65, wherein a proline occurring at the position corresponding to position 369 of SEQ ID NO:12 is replaced with serine or histidine.

70. A DNA molecule according to claim 65, wherein a valine occurring at the position corresponding to position 371 of SEQ ID NO:12 is replaced with leucine.

71. A DNA molecule according to claim 65, wherein a tyrosine occurring at the position corresponding to position 432 of SEQ ID NO:12 is replaced with cysteine, isoleucine, leucine, threonine, methionine, valine, alanine, or arginine.

72. A DNA molecule according to claim 65, wherein an alanine occurring at the position corresponding to position 436 of SEQ ID NO:12 is replaced with proline.

73. A DNA molecule according to claim 65, wherein a isoleucine occurring at the position corresponding to position 481 of SEQ ID NO:12 is replaced with threonine, histidine, glycine, or asparagine.

74. A DNA molecule according to claim 65, wherein a valine occurring at the position corresponding to position 517 of SEQ ID NO:12 is replaced with alanine.

75. A DNA molecule according to claim 27, wherein said DNA molecule is isolated from cotton and wherein said amino acid substitution occurs at a position corresponding to position 217, 222, 223, 365, 367, 428, 432, 477, or 513 of SEQ ID NO:16.

76. A DNA molecule according to claim 75, wherein a cysteine occurring at the position corresponding to position 217 of SEQ ID NO:16 is replaced with phenylalanine, leucine, or lysine.

77. A DNA molecule according to claim 75, an alanine occurring at the position corresponding to position 222 of SEQ ID NO:16 is replaced with valine, threonine, leucine, cysteine, or isoleucine.

78. A DNA molecule according to claim 75, wherein a glycine occurring at the position corresponding to position 223 of SEQ ID NO:16 is replaced with serine or leucine.

79. A DNA molecule according to claim 75, wherein a proline occurring at the position corresponding to position 365 of SEQ ID NO:16 is replaced with serine or histidine.

80. A DNA molecule according to claim 75, wherein a valine occurring at the position corresponding to position 367 of SEQ ID NO:16 is replaced with leucine.

81. A DNA molecule according to claim 75, wherein a tyrosine occurring at the position corresponding to position 428 of SEQ ID NO:16 is replaced with cysteine, isoleucine, leucine, threonine, methionine, valine, alanine, or arginine.

82. A DNA molecule according to claim 75, wherein an alanine occurring at the position corresponding to position 432 of SEQ ID NO:16 is replaced with proline.

83. A DNA molecule according to claim 75, wherein a isoleucine occurring at the position corresponding to position 477 of SEQ ID NO:16 is replaced with threonine, histidine, glycine, or asparagine.

84. A DNA molecule according to claim 75, wherein a valine occurring at the position corresponding to position 513 of SEQ ID NO:16 is replaced with alanine.

85. A DNA molecule according to claim 27, wherein said DNA molecule is isolated from sugar beet and wherein said amino acid substitution occurs at a position corresponding to position 238, 243, 244, 386, 388, 449, 453, 498, or 534 of SEQ ID NO:18.

86. A DNA molecule according to claim 85, wherein a cysteine occurring at the position corresponding to position 238 of SEQ ID NO:18 is replaced with phenylalanine, leucine, or lysine.

87. A DNA molecule according to claim 85, an alanine occurring at the position corresponding to position 243 of SEQ ID NO:18 is replaced with valine, threonine, leucine, cysteine, or isoleucine.

88. A DNA molecule according to claim 85, wherein a glycine occurring at the position corresponding to position 244 of SEQ ID NO:18 is replaced with serine or leucine.

89. A DNA molecule according to claim 85, wherein a proline occurring at the position corresponding to position 386 of SEQ ID NO:18 is replaced with serine or histidine.

90. A DNA molecule according to claim 85, wherein a valine occurring at the position corresponding to position 388 of SEQ ID NO:18 is replaced with leucine.

91. A DNA molecule according to claim 85, wherein a tyrosine occurring at the position corresponding to position 449 of SEQ ID NO:18 is replaced with cysteine, isoleucine, leucine, threonine, methionine, valine, alanine, or arginine.

92. A DNA molecule according to claim 85, wherein an alanine occurring at the position corresponding to position 453 of SEQ ID NO:18 is replaced with proline.

93. A DNA molecule according to claim 85, wherein a isoleucine occurring at the position corresponding to position 498 of SEQ ID NO:18 is replaced with threonine, histidine, glycine, or asparagine.

94. A DNA molecule according to claim 85, wherein a valine occurring at the position corresponding to position 534 of SEQ ID NO:18 is replaced with alanine.

95. A DNA molecule according to claim 27, wherein said DNA molecule is isolated from rape and wherein said amino acid substitution occurs at a position corresponding to position 214, 219, 220, 362, 364, 425, 429, 474, or 510 of SEQ ID NO:20.

96. A DNA molecule according to claim 95, wherein a cysteine occurring at the position corresponding to position 214 of SEQ ID NO:20 is replaced with phenylalanine, leucine, or lysine.

97. A DNA molecule according to claim 95, an alanine occurring at the position corresponding to position 219 of SEQ ID NO:20 is replaced with valine, threonine, leucine, cysteine, or isoleucine.

98. A DNA molecule according to claim 95, wherein a glycine occurring at the position corresponding to position 220 of SEQ ID NO:20 is replaced with serine or leucine.

99. A DNA molecule according to claim 95, wherein a proline occurring at the position corresponding to position 362 of SEQ ID NO:20 is replaced with serine or histidine.

100. A DNA molecule according to claim 95, wherein a valine occurring at the position corresponding to position 364 of SEQ ID NO:20 is replaced with leucine.

101. A DNA molecule according to claim 95, wherein a tyrosine occurring at the position corresponding to position 425 of SEQ ID NO:20 is replaced with cysteine, isoleucine, leucine, threonine, methionine, valine, alanine, or arginine.

102. A DNA molecule according to claim 95, wherein an alanine occurring at the position corresponding to position 429 of SEQ ID NO:20 is replaced with proline.

103. A DNA molecule according to claim 95, wherein a isoleucine occurring at the position corresponding to position 474 of SEQ ID NO:20 is replaced with threonine, histidine, glycine, or asparagine.

104. A DNA molecule according to claim 95, wherein a valine occurring at the position corresponding to 510 of SEQ ID NO:20 is replaced with alanine.

105. A DNA molecule according to claim 27, wherein said DNA molecule is isolated from rice and wherein said amino acid substitution occurs at a position corresponding to position 138, 140, 201, 205, 250, or 286 of SEQ ID NO:22.

106. A DNA molecule according to claim 105, wherein a proline occurring at the position corresponding to position 138 of SEQ ID NO:22 is replaced with serine or histidine.

107. A DNA molecule according to claim 105, wherein a valine occurring at the position corresponding to position 140 of SEQ ID NO:22 is replaced with leucine.

108. A DNA molecule according to claim 105, wherein a tyrosine occurring at the position corresponding to position 201 of SEQ ID NO:22 is replaced with cysteine, isoleucine, leucine, threonine, methionine, valine, alanine, or arginine.

109. A DNA molecule according to claim 105, wherein a serine occurring at the position corresponding to position 205 of SEQ ID NO:22 is replaced with proline.

110. A DNA molecule according to claim 105, wherein a isoleucine occurring at the position corresponding to position 250 of SEQ ID NO:22 is replaced with threonine, histidine, glycine, or asparagine.

111. A DNA molecule according to claim 105, wherein a valine occurring at the position corresponding to 286 of SEQ ID NO:22 is replaced with alanine.

112. A DNA molecule according to claim 27, wherein said DNA molecule is isolated from sorghum and wherein said amino acid substitution occurs at a position corresponding to position 118, 123, 124, 266, 268, 329, 333, 378, or 414 of SEQ ID NO:24.

113. A DNA molecule according to claim 112, wherein a cysteine occurring at the position corresponding to position 118 of SEQ ID NO:24 is replaced with phenylalanine, leucine, or lysine.

114. A DNA molecule according to claim 112, an alanine occurring at the position corresponding to position 123 of SEQ ID NO:24 is replaced with valine, threonine, leucine, cysteine, or isoleucine.

115. A DNA molecule according to claim 112, wherein a glycine occurring at the position corresponding to position 124 of SEQ ID NO:24 is replaced with serine or leucine.

116. A DNA molecule according to claim 112, wherein a proline occurring at the position corresponding to position 266 of SEQ ID NO:24 is replaced with serine or histidine.

117. A DNA molecule according to claim 112, wherein a valine occurring at the position corresponding to position 268 of SEQ ID NO:24 is replaced with leucine.

118. A DNA molecule according to claim 112, wherein a tyrosine occurring at the position corresponding to position 329 of SEQ ID NO:24 is replaced with cysteine, isoleucine, leucine, threonine, methionine, valine, alanine, or arginine.

119. A DNA molecule according to claim 112, wherein an alanine occurring at the position corresponding to position 333 of SEQ ID NO:24 is replaced with proline.

120. A DNA molecule according to claim 112, wherein a isoleucine occurring at the position corresponding to position 378 of SEQ ID NO:24 is replaced with threonine, histidine, glycine, or asparagine.

121. A DNA molecule according to claim 112, wherein a valine occurring at the position corresponding to 414 of SEQ ID NO:24 is replaced with alanine.

122. A chimeric gene comprising a promoter that is active in a plant operably linked to the DNA molecule of claim 1.

123. A chimeric gene according to claim 122, additionally comprising a signal sequence operably linked to said DNA molecule, wherein said signal sequence targets the protox enzyme encoded by said DNA molecule into the chloroplast.

124. A chimeric gene according to claim 122, additionally comprising a signal sequence operably linked to said DNA molecule, wherein said signal sequence targets the protox enzyme encoded by said DNA molecule into the mitochondria.

125. A recombinant vector comprising a chimeric gene according to claim 122.

126. A host cell comprising a vector according to claim 125, wherein said host cell expresses said DNA molecule.

127. A host cell according to claim 126, wherein said host cell is selected from the group consisting of a plant cell, a bacterial cell, a yeast cell, and an insect cell.

128. A chimeric gene comprising a plant plastid promoter operably linked to the DNA molecule of claim 1.

129. The chimeric gene of claim 128, wherein said plant plastid promoter is a clpP gene promoter.

130. The chimeric gene of claim 128, further comprising a 5' untranslated sequence (5' UTR) from said plastid promoter and a plastid gene 3' untranslated sequence (3' UTR) operably linked to said DNA molecule.

131. The chimeric gene of claim 130, wherein said plant plastid promoter is a clpP gene promoter, and wherein said 3' UTR is a plastid rps 6 gene 3' untranslated sequence.

132. A plastid transformation vector comprising the chimeric gene of claim 128.

133. A plant plastid comprising the plastid transformation vector of claim 132, wherein said modified enzyme is expresses in said plant plastid.

134. A plant, plant tissue, or plant cell comprising the plant plastid of claim 133, wherein said modified enzyme is expressed in said plant, plant tissue, or plant cell and confers upon said plant, plant tissue or plant cell tolerance to an inhibitor of naturally occurring protox activity.

135. A plant, plant tissue, or plant cell, transformed with the DNA molecule of claim 1, wherein said DNA molecule is expressed in said plant, plant tissue, or plant cell and confers tolerance thereupon to an inhibitor of naturally occurring protox activity.

136. Progeny of a plant according to claim 135.

137. The plant, plant tissue, or plant cell, of claim 135, wherein said plant, plant tissue, or plant cell is selected from the group consisting of Arahidopsis, sugar cane, soybean, barley, cotton, tobacco, sugar beet, rape, maize, wheat, sorghum, rye, oats, turf and forage grasses, millet, forage and rice.

138. The plant, plant tissue, or plant cell, of claim 137, wherein said plant, plant tissue, or plant cell is selected from the group consisting of Arabidopsis, soybean, cotton, sugar beet, rape, maize, wheat, sorghum, and rice.

139. A method for controlling the growth of undesired vegetation, which comprises applying to a plant population comprising a plant according to claim 135 or progeny of said plant an effective amount of a protox-inhibiting herbicide.

140. The method of claim 139, wherein said plant is selected from the group consisting of Arabidopsis, sugar cane, soybean, barley, cotton, tobacco, sugar beet, oilseed rape, maize, wheat, sorghum, rye, oats, turf and forage grasses, millet, forage and rice.

141. The method of claim 139, wherein said protox-inhibiting herbicide is selected from the group consisting of an aryluracil, a diphienylether, an oxidiazole, an imide, a phenyl pyrazole, a pyridine derivative, a 3-substituted-2-aryl-4,5,6,7-tetrahydroindazole, a phenopylate, O-phenylpyrrolidino-analogs of said phenopylate, and piperidinocarbamate analogs of said phenopylate.

142. The method of claim 141, wherein said protox-inhibiting herbicide is an imide having the formula (Formula V)

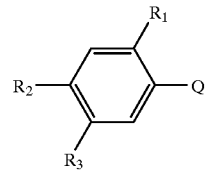

wherein Q equals (Formula VI)

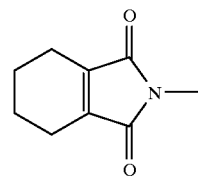

OR (Formula VII)

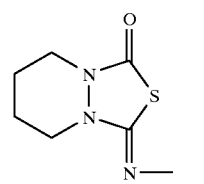

OR (Formula VIII)

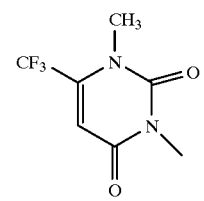

OR (Formula IX)

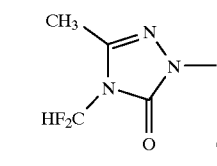

OR (Formula IXa)

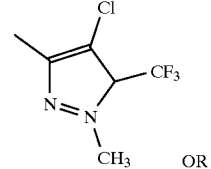

OR (Formula IXb)

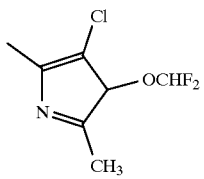

and wherein $R_1$ equals H, Cl or F, $R_2$ equals Cl and $R_3$ is an optimally substituted ether, thioether, ester, amino or alkyl group, and wherein $R_2$ and $R_3$ together may form a 5 or 6 membered heterocyclic ring, or wherein said protox-inhibiting herbicide is an imide having the formula (Formula VIIa)

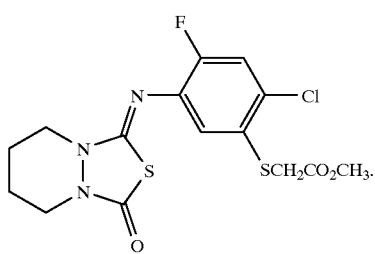

143. The method of claim 142, wherein said imide is selected from the group consisting of (Formula X)

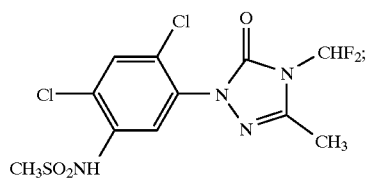

(Formula XI)

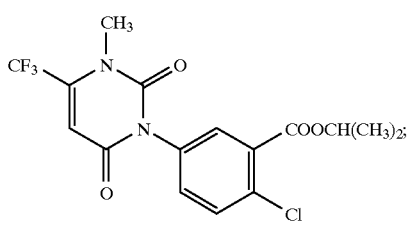

(Formula XII)

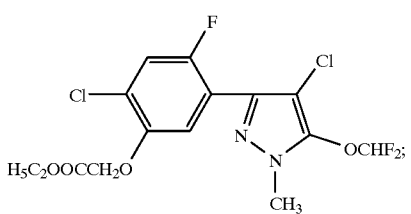

(Formula XIII)

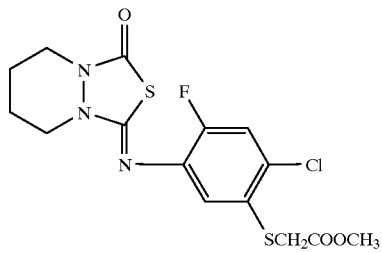

(Formula XIV)

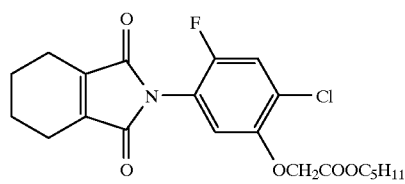

(Formula XV)

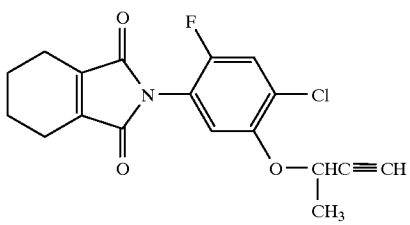

(Formula XVI)

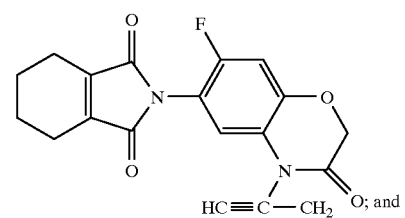

(Formula XVII)

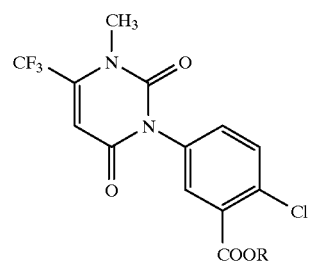

where R signifies ($C_{2-6}$-alkenyloxy)carbonyl-$C_{1-4}$-alkyl.

144. The method of claim 139, wherein said protox-inhibiting herbicide has the formula selected from the group consisting of (Formula XVIII)
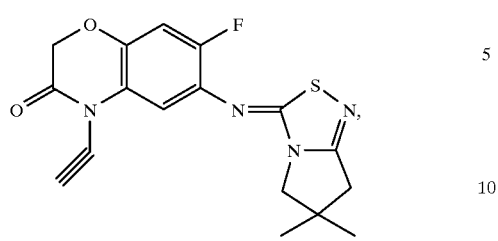
(Formula XIX)
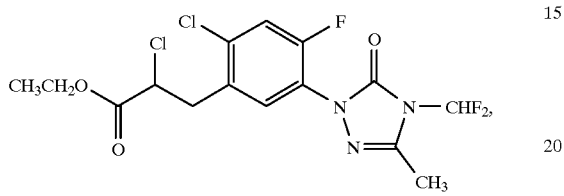
(Formula XX)
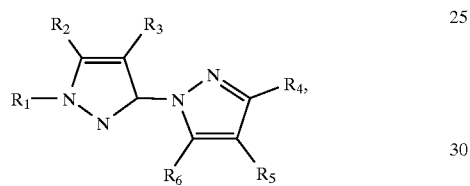
(Formula XXI)
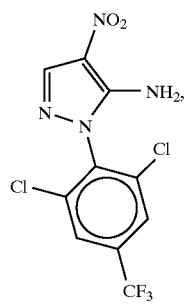
(Formula XXIa)
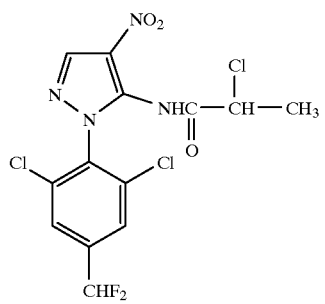
* * * * *

UNITED STATES PATENT AND TRADEMARK OFFICE
CERTIFICATE OF CORRECTION

PATENT NO. : 5,939,602
DATED : August 17, 1999
INVENTOR(S) : Volrath et al.

Page 1 of 4

It is certified that error appears in the above-identified patent and that said Letters Patent is hereby corrected as shown below:

At column 5, line 8, change "PcIp" to -- PcIp --; and, change "cIpP" to -- clpP --.

At column 5, line 10, change "PcIp" to -- PcIp --; and, change "cIpP" to -- clpP --.

At column 5, line 12, change "PcIp" to -- PcIp --; and, change "cIpP" to -- clpP --.

At column 27, line 52, change "c/pP" to -- clpP --.

At columns 39-40, Table 1, line which begins Sugpt-1, amino acid positions 381 to 400, change "SLSKFYYPV AAVSLSPKE" to -- SLSKFYYPPV AAVSLSYPKE --.

At columns 39-40, Table 1, line which begins Sugpt-1, amino acid positions 481 to 500, change "INPAKLPRV LGVRVWPQAI" to -- INPDAKLPRV LGVRVWPQAI --.

At column 44, line 40, change "NotI" to -- NotI --.

At column 62, lines 33, 34, 38, 44, 48, and 60, change every instance of "cIpP" to -- clpP --.

At column 62, line 44, change "PcIp" to -- PcIp --.

At column 62, line 50, change "PcIp" to -- PcIp --.

At column 63, lines 23, 30, 42, 47, 53, 55, and 59, change every instance of "cIpP" to -- clpP --.

At column 63, line 51, change "PcIp" to -- PcIp --.

At column 63, line 55, change "PcIp" to -- PcIp --.

At column 64, lines 19, 48, 60 and 66, change every instance of "cIpP" to -- clpP --.

At column 66, line 4, change "subcdoned" to -- subcloned --.

UNITED STATES PATENT AND TRADEMARK OFFICE
CERTIFICATE OF CORRECTION

PATENT NO. : 5,939,602
DATED : August 17, 1999
INVENTOR(S) : Volrath et al.

Page 2 of 4

It is certified that error appears in the above-identified patent and that said Letters Patent is hereby corrected as shown below:

Beneath Table 1 at columns 39-40, please insert Table 2 as follows:

-- TABLE 2

Comparison of the Arabidopsis (SEQ ID NO:4) and
Maize (SEQ ID NO:8) Protox-2 Amino Acid Sequences Identical residues are denoted by the vertical bar between the two sequences. Alignment is performed using the GAP program described in Deveraux *et al.*, *Nucleic Acids Res.* 12:387-395 (1984).

Percent Similarity: 75.889  Percent Identity: 57.905
Protox-2.Pep x Mzprotox-2.Pep

```
  1 ........................MASGAVAD.HQIEAVSGKRVAV  21
                           .|  |:|: .:  |..::.|||
  1 MLALTASASSASSHPYRHASAHTRRPRLRAVLAMAGSDDPRAAPARSVAV  50

22 VGAGVSGLAAAYKLKSRGLNVTVFEADGRVGGKLRSVMQNGLIWDEGANT  71
    |||||||||||:|: .|:|||||||.:|.|||:|.  :.|::|||||||
 51 VGAGVSGLAAAYRLRQSGVNVTVFEAADRAGGKIRTNSEGGFVWDEGANT 100

72 MTEAEPEVGSLLDDLGLREKQQFPISQKKRYIVRNGVPVMLPTNPIELVT 121
    |||:| |.:.|:|||||.:|||:| ||.||||::|.|.::|.:||.|:.
101 MTEGEWEASRLIDDLGLQDKQQYPNSQHKRYIVKDGAPALIPSDPISLMK 150

122 SSVLSTQSKFQILLEPPFLWKK....KSSKVSDASAEESVSEFFQRHFGQE 167
    |||||.||:.:::|||||:||   .|:|||:. .|||:.| :||||.|
151 SSVLSTKSKIALFFEPPFLYKKANTRNSGKVSEEHLSESVGSFCERHFGRE 200

168 VVDYLIDPFVGGTSAADPDSLSMKHSFPDLWNVEKSPGSIIVGAIRTKFA 217
    ||||::|||||:||||:||:|||::|.||.|||:|:.:||:||||| .|:|
```

UNITED STATES PATENT AND TRADEMARK OFFICE
CERTIFICATE OF CORRECTION

PATENT NO. : 5,939,602
DATED : August 17, 1999
INVENTOR(S) : Volrath et al.

Page 3 of 4

It is certified that error appears in the above-identified patent and that said Letters Patent is hereby corrected as shown below:

```
201 VVDYFVDPFVAGTSAGDPESLSIRHAFPALWNLERKYGSVIVGAILSKLA 250

218 AKGGKSRDTKSSPGTKKGSRGSFSFKGGMQILPDTLCKSLSHDEINLDSK 267
    |||:. :. ..|.|.:..|.||||.|||| | :.| ..::.|::.|:..
251 AKGDPVKTRHDSSGKRRNRRVSFSFHGGMQSLINALHNEVGDDNVKLGTE 300

268 VLSLS..YNSGSRQENWSLSCVSHNETQRQ...NPHYDAVIMTAPLCNVK 312
    ||||. ::::.. :.||:|. |.:..::: |. :||||||||:||:
301 VLSLACTFDGVPALGRWSISVDSKDSGDKDLASNQTFDAVIMTAPLSNVR 350

313 EMKVMKGGQPFQLNFLPEINYMPLSVLITTFTKEKVKRPLEGFGVLIPSK 362
    ||. |||.|. |:|||.::|:|||:::|.|.|:.||:|||||||||| |
351 RMKFTKGGAPVVLDFLPKMDYLPLSLMVTAFKKDDVKKPLEGFGVLIPYK 400

363 E.QKHGFKTLGTLFSSMMFPDRSPSDVHLYTTFIGGSRNQELAKASTDEL 411
    | ||||:||||||||||||||.|.| .|||||:|||:|.:|| |.|. |
401 EQQKHGLKTLGTLFSSMMFPDRAPDDQYLYTTFVGGSHNRDLAGAPTSIL 450
```

UNITED STATES PATENT AND TRADEMARK OFFICE
CERTIFICATE OF CORRECTION

PATENT NO. : 5,939,602
DATED : August 17, 1999
INVENTOR(S) : Volrath et al.

It is certified that error appears in the above-identified patent and that said Letters Patent is hereby corrected as shown below:

TABLE 2-continued

```
412 KQVVTSDLQRLLGVEGEPVSVNHYYWRKAFPLYDSSYDSVMEAIDKMEND 461
    ||:||||.:||||||:|. |.| || .|||||: .|.||:|||:|||..
451 KQLVTSDLKKLLGVEGQPTFVKHVYWGNAFPLYGHDYSSVLEAIEKMEKN 500

462 LPGFFYAGNHRGGLSVGKSIASGCKAADLVISYLESCSNDKKPNDSL* 509
    |||||||| ::||.||. ||||:||||.||||||  ......:
501 LPGFFYAGNSKDGLAVGSVIASGSKAADLAISYLESHTKHNNSH*... 545
```

Signed and Sealed this

Ninth Day of May, 2000

Attest:

Q. TODD DICKINSON

*Attesting Officer*    *Director of Patents and Trademarks*

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
      (A) LENGTH: 1719 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Arabidopsis thaliana (vii) IMMEDIATE SOURCE:
      (B) CLONE: pWDC-2 (NRRL B-21238)

(ix) FEATURE:
      (A) NAME/KEY: CDS
      (B) LOCATION: 31..1644
      (D) OTHER INFORMATION: /product= "Arabidopsis protox-1"

(xi) SEQUENCE DESCRIPTION: SEQ ID NO:1:

```
TGACAAAATT CCGAATTCTC TGCGATTTCC ATG GAG TTA TCT CTT CTC CGT CCG       54
                                Met Glu Leu Ser Leu Leu Arg Pro
                                 1               5

ACG ACT CAA TCG CTT CTT CCG TCG TTT TCG AAG CCC AAT CTC CGA TTA       102
Thr Thr Gln Ser Leu Leu Pro Ser Phe Ser Lys Pro Asn Leu Arg Leu
     10                  15                  20

AAT GTT TAT AAG CCT CTT AGA CTC CGT TGT TCA GTG GCC GGT GGA CCA       150
Asn Val Tyr Lys Pro Leu Arg Leu Arg Cys Ser Val Ala Gly Gly Pro
 25                  30                  35                  40

ACC GTC GGA TCT TCA AAA ATC GAA GGC GGA GGA GGC ACC ACC ATC ACG       198
Thr Val Gly Ser Ser Lys Ile Glu Gly Gly Gly Gly Thr Thr Ile Thr
```

-continued

```
                 45                    50                    55
ACG GAT TGT GTG ATT GTC GGC GGA GGT ATT AGT GGT CTT TGC ATC GCT      246
Thr Asp Cys Val Ile Val Gly Gly Gly Ile Ser Gly Leu Cys Ile Ala
            60                    65                    70

CAG GCG CTT GCT ACT AAG CAT CCT GAT GCT GCT CCG AAT TTA ATT GTG      294
Gln Ala Leu Ala Thr Lys His Pro Asp Ala Ala Pro Asn Leu Ile Val
        75                    80                    85

ACC GAG GCT AAG GAT CGT GTT GGA GGC AAC ATT ATC ACT CGT GAA GAG      342
Thr Glu Ala Lys Asp Arg Val Gly Gly Asn Ile Ile Thr Arg Glu Glu
    90                    95                   100

AAT GGT TTT CTC TGG GAA GAA GGT CCC AAT AGT TTT CAA CCG TCT GAT      390
Asn Gly Phe Leu Trp Glu Glu Gly Pro Asn Ser Phe Gln Pro Ser Asp
105                   110                   115                   120

CCT ATG CTC ACT ATG GTG GTA GAT AGT GGT TTG AAG GAT GAT TTG GTG      438
Pro Met Leu Thr Met Val Val Asp Ser Gly Leu Lys Asp Asp Leu Val
                125                   130                   135

TTG GGA GAT CCT ACT GCG CCA AGG TTT GTG TTG TGG AAT GGG AAA TTG      486
Leu Gly Asp Pro Thr Ala Pro Arg Phe Val Leu Trp Asn Gly Lys Leu
            140                   145                   150

AGG CCG GTT CCA TCG AAG CTA ACA GAC TTA CCG TTC TTT GAT TTG ATG      534
Arg Pro Val Pro Ser Lys Leu Thr Asp Leu Pro Phe Phe Asp Leu Met
        155                   160                   165

AGT ATT GGT GGG AAG ATT AGA GCT GGT TTT GGT GCA CTT GGC ATT CGA      582
Ser Ile Gly Gly Lys Ile Arg Ala Gly Phe Gly Ala Leu Gly Ile Arg
    170                   175                   180

CCG TCA CCT CCA GGT CGT GAA GAA TCT GTG GAG GAG TTT GTA CGG CGT      630
Pro Ser Pro Pro Gly Arg Glu Glu Ser Val Glu Glu Phe Val Arg Arg
185                   190                   195                   200

AAC CTC GGT GAT GAG GTT TTT GAG CGC CTG ATT GAA CCG TTT TGT TCA      678
Asn Leu Gly Asp Glu Val Phe Glu Arg Leu Ile Glu Pro Phe Cys Ser
                205                   210                   215

GGT GTT TAT GCT GGT GAT CCT TCA AAA CTG AGC ATG AAA GCA GCG TTT      726
Gly Val Tyr Ala Gly Asp Pro Ser Lys Leu Ser Met Lys Ala Ala Phe
            220                   225                   230

GGG AAG GTT TGG AAA CTA GAG CAA AAT GGT GGA AGC ATA ATA GGT GGT      774
Gly Lys Val Trp Lys Leu Glu Gln Asn Gly Gly Ser Ile Ile Gly Gly
        235                   240                   245

ACT TTT AAG GCA ATT CAG GAG AGG AAA AAC GCT CCC AAG GCA GAA CGA      822
Thr Phe Lys Ala Ile Gln Glu Arg Lys Asn Ala Pro Lys Ala Glu Arg
    250                   255                   260

GAC CCG CGC CTG CCA AAA CCA CAG GGC CAA ACA GTT GGT TCT TTC AGG      870
Asp Pro Arg Leu Pro Lys Pro Gln Gly Gln Thr Val Gly Ser Phe Arg
265                   270                   275                   280

AAG GGA CTT CGA ATG TTG CCA GAA GCA ATA TCT GCA AGA TTA GGT AGC      918
Lys Gly Leu Arg Met Leu Pro Glu Ala Ile Ser Ala Arg Leu Gly Ser
                285                   290                   295

AAA GTT AAG TTG TCT TGG AAG CTC TCA GGT ATC ACT AAG CTG GAG AGC      966
Lys Val Lys Leu Ser Trp Lys Leu Ser Gly Ile Thr Lys Leu Glu Ser
            300                   305                   310

GGA GGA TAC AAC TTA ACA TAT GAG ACT CCA GAT GGT TTA GTT TCC GTG     1014
Gly Gly Tyr Asn Leu Thr Tyr Glu Thr Pro Asp Gly Leu Val Ser Val
        315                   320                   325

CAG AGC AAA AGT GTT GTA ATG ACG GTG CCA TCT CAT GTT GCA AGT GGT     1062
Gln Ser Lys Ser Val Val Met Thr Val Pro Ser His Val Ala Ser Gly
    330                   335                   340

CTC TTG CGC CCT CTT TCT GAA TCT GCT GCA AAT GCA CTC TCA AAA CTA     1110
Leu Leu Arg Pro Leu Ser Glu Ser Ala Ala Asn Ala Leu Ser Lys Leu
345                   350                   355                   360

TAT TAC CCA CCA GTT GCA GCA GTA TCT ATC TCG TAC CCG AAA GAA GCA     1158
Tyr Tyr Pro Pro Val Ala Ala Val Ser Ile Ser Tyr Pro Lys Glu Ala
```

```
                                 365                 370                 375
ATC CGA ACA GAA TGT TTG ATA GAT GGT GAA CTA AAG GGT TTT GGG CAA        1206
Ile Arg Thr Glu Cys Leu Ile Asp Gly Glu Leu Lys Gly Phe Gly Gln
        380                 385                 390

TTG CAT CCA CGC ACG CAA GGA GTT GAA ACA TTA GGA ACT ATC TAC AGC        1254
Leu His Pro Arg Thr Gln Gly Val Glu Thr Leu Gly Thr Ile Tyr Ser
        395                 400                 405

TCC TCA CTC TTT CCA AAT CGC GCA CCG CCC GGA AGA ATT TTG CTG TTG        1302
Ser Ser Leu Phe Pro Asn Arg Ala Pro Pro Gly Arg Ile Leu Leu Leu
        410                 415                 420

AAC TAC ATT GGC GGG TCT ACA AAC ACC GGA ATT CTG TCC AAG TCT GAA        1350
Asn Tyr Ile Gly Gly Ser Thr Asn Thr Gly Ile Leu Ser Lys Ser Glu
425                 430                 435                 440

GGT GAG TTA GTG GAA GCA GTT GAC AGA GAT TTG AGG AAA ATG CTA ATT        1398
Gly Glu Leu Val Glu Ala Val Asp Arg Asp Leu Arg Lys Met Leu Ile
        445                 450                 455

AAG CCT AAT TCG ACC GAT CCA CTT AAA TTA GGA GTT AGG GTA TGG CCT        1446
Lys Pro Asn Ser Thr Asp Pro Leu Lys Leu Gly Val Arg Val Trp Pro
        460                 465                 470

CAA GCC ATT CCT CAG TTT CTA GTT GGT CAC TTT GAT ATC CTT GAC ACG        1494
Gln Ala Ile Pro Gln Phe Leu Val Gly His Phe Asp Ile Leu Asp Thr
        475                 480                 485

GCT AAA TCA TCT CTA ACG TCT TCG GGC TAC GAA GGG CTA TTT TTG GGT        1542
Ala Lys Ser Ser Leu Thr Ser Ser Gly Tyr Glu Gly Leu Phe Leu Gly
        490                 495                 500

GGC AAT TAC GTC GCT GGT GTA GCC TTA GGC CGG TGT GTA GAA GGC GCA        1590
Gly Asn Tyr Val Ala Gly Val Ala Leu Gly Arg Cys Val Glu Gly Ala
505                 510                 515                 520

TAT GAA ACC GCG ATT GAG GTC AAC AAC TTC ATG TCA CGG TAC GCT TAC        1638
Tyr Glu Thr Ala Ile Glu Val Asn Asn Phe Met Ser Arg Tyr Ala Tyr
        525                 530                 535

AAG TAAATGTAAA ACATTAAATC TCCCAGCTTG CGTGAGTTTT ATTAAATATT            1691
Lys

TTGAGATATC CAAAAAAAAA AAAAAAA                                          1719

(2) INFORMATION FOR SEQ ID NO:2:

(i) SEQUENCE CHARACTERISTICS:
        (A) LENGTH: 537 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Leu Ser Leu Leu Arg Pro Thr Thr Gln Ser Leu Leu Pro Ser
  1               5                  10                  15

Phe Ser Lys Pro Asn Leu Arg Leu Asn Val Tyr Lys Pro Leu Arg Leu
                 20                  25                  30

Arg Cys Ser Val Ala Gly Gly Pro Thr Val Gly Ser Ser Lys Ile Glu
             35                  40                  45

Gly Gly Gly Gly Thr Thr Ile Thr Thr Asp Cys Val Ile Val Gly Gly
         50                  55                  60

Gly Ile Ser Gly Leu Cys Ile Ala Gln Ala Leu Ala Thr Lys His Pro
 65                  70                  75                  80

Asp Ala Ala Pro Asn Leu Ile Val Thr Glu Ala Lys Asp Arg Val Gly
                 85                  90                  95

Gly Asn Ile Ile Thr Arg Glu Glu Asn Gly Phe Leu Trp Glu Glu Gly
            100                 105                 110
```

```
Pro Asn Ser Phe Gln Pro Ser Asp Pro Met Leu Thr Met Val Val Asp
    115                 120                 125

Ser Gly Leu Lys Asp Asp Leu Val Leu Gly Asp Pro Thr Ala Pro Arg
130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Leu Gly Ile Arg Pro Ser Pro Gly Arg Glu Glu
                180                 185                 190

Ser Val Glu Glu Phe Val Arg Arg Asn Leu Gly Asp Glu Val Phe Glu
    195                 200                 205

Arg Leu Ile Glu Pro Phe Cys Ser Gly Val Tyr Ala Gly Asp Pro Ser
    210                 215                 220

Lys Leu Ser Met Lys Ala Ala Phe Gly Lys Val Trp Lys Leu Glu Gln
225                 230                 235                 240

Asn Gly Gly Ser Ile Ile Gly Gly Thr Phe Lys Ala Ile Gln Glu Arg
                245                 250                 255

Lys Asn Ala Pro Lys Ala Glu Arg Asp Pro Arg Leu Pro Lys Pro Gln
                260                 265                 270

Gly Gln Thr Val Gly Ser Phe Arg Lys Gly Leu Arg Met Leu Pro Glu
    275                 280                 285

Ala Ile Ser Ala Arg Leu Gly Ser Lys Val Lys Leu Ser Trp Lys Leu
290                 295                 300

Ser Gly Ile Thr Lys Leu Glu Ser Gly Gly Tyr Asn Leu Thr Tyr Glu
305                 310                 315                 320

Thr Pro Asp Gly Leu Val Ser Val Gln Ser Lys Ser Val Val Met Thr
                325                 330                 335

Val Pro Ser His Val Ala Ser Gly Leu Leu Arg Pro Leu Ser Glu Ser
                340                 345                 350

Ala Ala Asn Ala Leu Ser Lys Leu Tyr Tyr Pro Pro Val Ala Ala Val
                355                 360                 365

Ser Ile Ser Tyr Pro Lys Glu Ala Ile Arg Thr Glu Cys Leu Ile Asp
    370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Leu Phe Pro Asn Arg Ala
                405                 410                 415

Pro Pro Gly Arg Ile Leu Leu Leu Asn Tyr Ile Gly Gly Ser Thr Asn
                420                 425                 430

Thr Gly Ile Leu Ser Lys Ser Glu Gly Glu Leu Val Gly Ala Val Asp
                435                 440                 445

Arg Asp Leu Arg Lys Met Leu Ile Lys Pro Asn Ser Thr Asp Pro Leu
450                 455                 460

Lys Leu Gly Val Arg Val Trp Pro Gln Ala Ile Pro Gln Phe Leu Val
465                 470                 475                 480

Gly His Phe Asp Ile Leu Asp Thr Ala Lys Ser Ser Leu Thr Ser Ser
                485                 490                 495

Gly Tyr Glu Gly Leu Phe Leu Gly Gly Asn Tyr Val Ala Gly Val Ala
                500                 505                 510

Leu Gly Arg Cys Val Glu Gly Ala Tyr Glu Thr Ala Ile Glu Val Asn
                515                 520                 525

Asn Phe Met Ser Arg Tyr Ala Tyr Lys
530                 535
```

(2) INFORMATION FOR SEQ ID NO:3:

(i) SEQUENCE CHARACTERISTICS:
        (A) LENGTH: 1738 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Arabidopsis thaliana (vii) IMMEDIATE SOURCE:
        (B) CLONE: pWDC-1 (NRRL B-21237)

(ix) FEATURE:
        (A) NAME/KEY: CDS
        (B) LOCATION: 70..1596
        (D) OTHER INFORMATION: /product= "Arabidopsis protox-2"

(xi) SEQUENCE DESCRIPTION: SEQ ID NO:3:

```
TTTTTTACTT ATTTCCGTCA CTGCTTTCGA CTGGTCAGAG ATTTTGACTC TGAATTGTTG          60

CAGATAGCA ATG GCG TCT GGA GCA GTA GCA GAT CAT CAA ATT GAA GCG            108
          Met Ala Ser Gly Ala Val Ala Asp His Gln Ile Glu Ala
            1               5                  10

GTT TCA GGA AAA AGA GTC GCA GTC GTA GGT GCA GGT GTA AGT GGA CTT          156
Val Ser Gly Lys Arg Val Ala Val Val Gly Ala Gly Val Ser Gly Leu
 15                  20                  25

GCG GCG GCT TAC AAG TTG AAA TCG AGG GGT TTG AAT GTG ACT GTG TTT          204
Ala Ala Ala Tyr Lys Leu Lys Ser Arg Gly Leu Asn Val Thr Val Phe
 30                  35                  40                  45

GAA GCT GAT GGA AGA GTA GGT GGG AAG TTG AGA AGT GTT ATG CAA AAT          252
Glu Ala Asp Gly Arg Val Gly Gly Lys Leu Arg Ser Val Met Gln Asn
                 50                  55                  60

GGT TTG ATT TGG GAT GAA GGA GCA AAC ACC ATG ACT GAG GCT GAG CCA          300
Gly Leu Ile Trp Asp Glu Gly Ala Asn Thr Met Thr Glu Ala Glu Pro
         65                  70                  75

GAA GTT GGG AGT TTA CTT GAT GAT CTT GGG CTT CGT GAG AAA CAA CAA          348
Glu Val Gly Ser Leu Leu Asp Asp Leu Gly Leu Arg Glu Lys Gln Gln
     80                  85                  90

TTT CCA ATT TCA CAG AAA AAG CGG TAT ATT GTG CGG AAT GGT GTA CCT          396
Phe Pro Ile Ser Gln Lys Lys Arg Tyr Ile Val Arg Asn Gly Val Pro
 95                 100                 105

GTG ATG CTA CCT ACC AAT CCC ATA GAG CTG GTC ACA AGT AGT GTG CTC          444
Val Met Leu Pro Thr Asn Pro Ile Glu Leu Val Thr Ser Ser Val Leu
110                 115                 120                 125

TCT ACC CAA TCT AAG TTT CAA ATC TTG TTG GAA CCA TTT TTA TGG AAG          492
Ser Thr Gln Ser Lys Phe Gln Ile Leu Leu Glu Pro Phe Leu Trp Lys
                130                 135                 140

AAA AAG TCC TCA AAA GTC TCA GAT GCA TCT GCT GAA GAA AGT GTA AGC          540
Lys Lys Ser Ser Lys Val Ser Asp Ala Ser Ala Glu Glu Ser Val Ser
            145                 150                 155

GAG TTC TTT CAA CGC CAT TTT GGA CAA GAG GTT GTT GAC TAT CTC ATC          588
Glu Phe Phe Gln Arg His Phe Gly Gln Glu Val Val Asp Tyr Leu Ile
        160                 165                 170

GAC CCT TTT GTT GGT GGA ACA AGT GCT GCG GAC CCT GAT TCC CTT TCA          636
Asp Pro Phe Val Gly Gly Thr Ser Ala Ala Asp Pro Asp Ser Leu Ser
    175                 180                 185

ATG AAG CAT TCT TTC CCA GAT CTC TGG AAT GTA GAG AAA AGT TTT GGC          684
```

```
            Met Lys His Ser Phe Pro Asp Leu Trp Asn Val Glu Lys Ser Phe Gly
            190             195                 200                 205
TCT ATT ATA GTC GGT GCA ATC AGA ACA AAG TTT GCT GCT AAA GGT GGT              732
Ser Ile Ile Val Gly Ala Ile Arg Thr Lys Phe Ala Ala Lys Gly Gly
            210                 215                 220

AAA AGT AGA GAC ACA AAG AGT TCT CCT GGC ACA AAA AAG GGT TCG CGT              780
Lys Ser Arg Asp Thr Lys Ser Ser Pro Gly Thr Lys Lys Gly Ser Arg
            225                 230                 235

GGG TCA TTC TCT TTT AAG GGG GGA ATG CAG ATT CTT CCT GAT ACG TTG              828
Gly Ser Phe Ser Phe Lys Gly Gly Met Gln Ile Leu Pro Asp Thr Leu
            240                 245                 250

TGC AAA AGT CTC TCA CAT GAT GAG ATC AAT TTA GAC TCC AAG GTA CTC              876
Cys Lys Ser Leu Ser His Asp Glu Ile Asn Leu Asp Ser Lys Val Leu
            255                 260                 265

TCT TTG TCT TAC AAT TCT GGA TCA AGA CAG GAG AAC TGG TCA TTA TCT              924
Ser Leu Ser Tyr Asn Ser Gly Ser Arg Gln Glu Asn Trp Ser Leu Ser
270                 275                 280                 285

TGT GTT TCG CAT AAT GAA ACG CAG AGA CAA AAC CCC CAT TAT GAT GCT              972
Cys Val Ser His Asn Glu Thr Gln Arg Gln Asn Pro His Tyr Asp Ala
            290                 295                 300

GTA ATT ATG ACG GCT CCT CTG TGC AAT GTG AAG GAG ATG AAG GTT ATG             1020
Val Ile Met Thr Ala Pro Leu Cys Asn Val Lys Glu Met Lys Val Met
            305                 310                 315

AAA GGA GGA CAA CCC TTT CAG CTA AAC TTT CTC CCC GAG ATT AAT TAC             1068
Lys Gly Gly Gln Pro Phe Gln Leu Asn Phe Leu Pro Glu Ile Asn Tyr
            320                 325                 330

ATG CCC CTC TCG GTT TTA ATC ACC ACA TTC ACA AAG GAG AAA GTA AAG             1116
Met Pro Leu Ser Val Leu Ile Thr Thr Phe Thr Lys Glu Lys Val Lys
            335                 340                 345

AGA CCT CTT GAA GGC TTT GGG GTA CTC ATT CCA TCT AAG GAG CAA AAG             1164
Arg Pro Leu Glu Gly Phe Gly Val Leu Ile Pro Ser Lys Glu Gln Lys
350                 355                 360                 365

CAT GGT TTC AAA ACT CTA GGT ACA CTT TTT TCA TCA ATG ATG TTT CCA             1212
His Gly Phe Lys Thr Leu Gly Thr Leu Phe Ser Ser Met Met Phe Pro
            370                 375                 380

GAT CGT TCC CCT AGT GAC GTT CAT CTA TAT ACA ACT TTT ATT GGT GGG             1260
Asp Arg Ser Pro Ser Asp Val His Leu Tyr Thr Thr Phe Ile Gly Gly
            385                 390                 395

AGT AGG AAC CAG GAA CTA GCC AAA GCT TCC ACT GAC GAA TTA AAA CAA             1308
Ser Arg Asn Gln Glu Leu Ala Lys Ala Ser Thr Asp Glu Leu Lys Gln
            400                 405                 410

GTT GTG ACT TCT GAC CTT CAG CGA CTG TTG GGG GTT GAA GGT GAA CCC             1356
Val Val Thr Ser Asp Leu Gln Arg Leu Leu Gly Val Glu Gly Glu Pro
            415                 420                 425

GTG TCT GTC AAC CAT TAC TAT TGG AGG AAA GCA TTC CCG TTG TAT GAC             1404
Val Ser Val Asn His Tyr Tyr Trp Arg Lys Ala Phe Pro Leu Tyr Asp
430                 435                 440                 445

AGC AGC TAT GAC TCA GTC ATG GAA GCA ATT GAC AAG ATG GAG AAT GAT             1452
Ser Ser Tyr Asp Ser Val Met Glu Ala Ile Asp Lys Met Glu Asn Asp
            450                 455                 460

CTA CCT GGG TTC TTC TAT GCA GGT AAT CAT CGA GGG GGC CTC TCT GTT             1500
Leu Pro Gly Phe Phe Tyr Ala Gly Asn His Arg Gly Gly Leu Ser Val
            465                 470                 475

GGG AAA TCA ATA GCA TCA GGT TGC AAA GCA GCT GAC CTT GTG ATC TCA             1548
Gly Lys Ser Ile Ala Ser Gly Cys Lys Ala Ala Asp Leu Val Ile Ser
            480                 485                 490

TAC CTG GAG TCT TGC TCA AAT GAC AAG AAA CCA AAT GAC AGC TTA TAACATTG       1603
Tyr Leu Glu Ser Cys Ser Asn Asp Lys Lys Pro Asn Asp Ser Leu
            495                 500                 505

AAGGTTCGTC CCTTTTTATC ACTTACTTTG TAAACTTGTA AAATGCAACA AGCCGCCGTG          1663
```

```
CGATTAGCCA ACAACTCAGC AAAACCCAGA TTCTCATAAG GCTCACTAAT TCCAGAATAA    1723

ACTATTTATG TAAAA                                                     1738
```

(2) INFORMATION FOR SEQ ID NO:4:

(i) SEQUENCE CHARACTERISTICS:
        (A) LENGTH: 508 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Ser Gly Ala Val Ala Asp His Gln Ile Glu Ala Val Ser Gly
  1               5                  10                  15

Lys Arg Val Ala Val Val Gly Ala Gly Val Ser Gly Leu Ala Ala Ala
                 20                  25                  30

Tyr Lys Leu Lys Ser Arg Gly Leu Asn Val Thr Val Phe Glu Ala Asp
             35                  40                  45

Gly Arg Val Gly Gly Lys Leu Arg Ser Val Met Gln Asn Gly Leu Ile
 50                  55                  60

Trp Asp Glu Gly Ala Asn Thr Met Thr Glu Ala Glu Pro Glu Val Gly
 65                  70                  75                  80

Ser Leu Leu Asp Asp Leu Gly Leu Arg Glu Lys Gln Gln Phe Pro Ile
                 85                  90                  95

Ser Gln Lys Lys Arg Tyr Ile Val Arg Asn Gly Val Pro Val Met Leu
             100                 105                 110

Pro Thr Asn Pro Ile Glu Leu Val Thr Ser Ser Val Leu Ser Thr Gln
         115                 120                 125

Ser Lys Phe Gln Ile Leu Leu Glu Pro Phe Leu Trp Lys Lys Lys Ser
130                 135                 140

Ser Lys Val Ser Asp Ala Ser Ala Glu Glu Ser Val Ser Glu Phe Phe
145                 150                 155                 160

Gln Arg His Phe Gly Gln Glu Val Val Asp Tyr Leu Ile Asp Pro Phe
                 165                 170                 175

Val Gly Gly Thr Ser Ala Ala Asp Pro Asp Ser Leu Ser Met Lys His
             180                 185                 190

Ser Phe Pro Asp Leu Trp Asn Val Glu Lys Ser Phe Gly Ser Ile Ile
         195                 200                 205

Val Gly Ala Ile Arg Thr Lys Phe Ala Ala Lys Gly Gly Lys Ser Arg
     210                 215                 220

Asp Thr Lys Ser Ser Pro Gly Thr Lys Lys Gly Ser Arg Gly Ser Phe
225                 230                 235                 240

Ser Phe Lys Gly Gly Met Gln Ile Leu Pro Asp Thr Leu Cys Lys Ser
                 245                 250                 255

Leu Ser His Asp Glu Ile Asn Leu Asp Ser Lys Val Leu Ser Leu Ser
             260                 265                 270

Tyr Asn Ser Gly Ser Arg Gln Glu Asn Trp Ser Leu Ser Cys Val Ser
         275                 280                 285

His Asn Glu Thr Gln Arg Gln Asn Pro His Tyr Asp Ala Val Ile Met
     290                 295                 300

Thr Ala Pro Leu Cys Asn Val Lys Glu Met Lys Val Met Lys Gly Gly
305                 310                 315                 320

Gln Pro Phe Gln Leu Asn Phe Leu Pro Glu Ile Asn Tyr Met Pro Leu
                 325                 330                 335
```

```
Ser Val Leu Ile Thr Thr Phe Thr Lys Glu Lys Val Lys Arg Pro Leu
            340                 345                 350

Glu Gly Phe Gly Val Leu Ile Pro Ser Lys Glu Gln Lys His Gly Phe
            355                 360                 365

Lys Thr Leu Gly Thr Leu Phe Ser Ser Met Met Phe Pro Asp Arg Ser
    370                 375                 380

Pro Ser Asp Val His Leu Tyr Thr Thr Phe Ile Gly Gly Ser Arg Asn
385                 390                 395                 400

Gln Glu Leu Ala Lys Ala Ser Thr Asp Glu Leu Lys Gln Val Val Thr
                405                 410                 415

Ser Asp Leu Gln Arg Leu Leu Gly Val Glu Gly Pro Val Ser Val
                420                 425                 430

Asn His Tyr Tyr Trp Arg Lys Ala Phe Pro Leu Tyr Asp Ser Ser Tyr
            435                 440                 445

Asp Ser Val Met Glu Ala Ile Asp Lys Met Glu Asn Asp Leu Pro Gly
450                 455                 460

Phe Phe Tyr Ala Gly Asn His Arg Gly Gly Leu Ser Val Gly Lys Ser
465                 470                 475                 480

Ile Ala Ser Gly Cys Lys Ala Ala Asp Leu Val Ile Ser Tyr Leu Glu
                485                 490                 495

Ser Cys Ser Asn Asp Lys Lys Pro Asn Asp Ser Leu
                500                 505

(2) INFORMATION FOR SEQ ID NO:5:

(i) SEQUENCE CHARACTERISTICS:
        (A) LENGTH: 1691 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Zea mays (maize)

(vii) IMMEDIATE SOURCE:
        (B) CLONE: pWDC-4 (NRRL B-21260)

(ix) FEATURE:
        (A) NAME/KEY: CDS
        (B) LOCATION: 1..1443
        (D) OTHER INFORMATION: /product= "Maize protox-1 cDNA (not
                               full-length); first seven nucleotides
                               removed vs. serial no. 60/012,705"

(xi) SEQUENCE DESCRIPTION: SEQ ID NO:5:

GCG GAC TGC GTC GTG GTG GGC GGA GGC ATC AGT GGC CTC TGC ACC GCG       48
Ala Asp Cys Val Val Val Gly Gly Gly Ile Ser Gly Leu Cys Thr Ala
 1               5                  10                  15

CAG GCG CTG GCC ACG CGG CAC GGC GTG GGG GAC GTG CTT GTC ACG GAG       96
Gln Ala Leu Ala Thr Arg His Gly Val Gly Asp Val Leu Val Thr Glu
                20                  25                  30

GCC CGC GCC CGC CCC GGC GGC AAC ATT ACC ACC GTC GAG CGC CCC GAG      144
Ala Arg Ala Arg Pro Gly Gly Asn Ile Thr Thr Val Glu Arg Pro Glu
            35                  40                  45

GAA GGG TAC CTC TGG GAG GAG GGT CCC AAC AGC TTC CAG CCC TCC GAC      192
Glu Gly Tyr Leu Trp Glu Glu Gly Pro Asn Ser Phe Gln Pro Ser Asp
        50                  55                  60

CCC GTT CTC ACC ATG GCC GTG GAC AGC GGA CTG AAG GAT GAC TTG GTT      240
```

```
              Pro Val Leu Thr Met Ala Val Asp Ser Gly Leu Lys Asp Asp Leu Val
              65              70                  75                  80

TTT GGG GAC CCA AAC GCG CCG CGT TTC GTG CTG TGG GAG GGG AAG CTG         288
Phe Gly Asp Pro Asn Ala Pro Arg Phe Val Leu Trp Glu Gly Lys Leu
                85                  90                  95

AGG CCC GTG CCA TCC AAG CCC GCC GAC CTC CCG TTC TTC GAT CTC ATG         336
Arg Pro Val Pro Ser Lys Pro Ala Asp Leu Pro Phe Phe Asp Leu Met
            100                 105                 110

AGC ATC CCA GGG AAG CTC AGG GCC GGT CTA GGC GCG CTT GGC ATC CGC         384
Ser Ile Pro Gly Lys Leu Arg Ala Gly Leu Gly Ala Leu Gly Ile Arg
            115                 120                 125

CCG CCT CCT CCA GGC CGC GAA GAG TCA GTG GAG GAG TTC GTG CGC CGC         432
Pro Pro Pro Pro Gly Arg Glu Glu Ser Val Glu Glu Phe Val Arg Arg
            130                 135                 140

AAC CTC GGT GCT GAG GTC TTT GAG CGC CTC ATT GAG CCT TTC TGC TCA         480
Asn Leu Gly Ala Glu Val Phe Glu Arg Leu Ile Glu Pro Phe Cys Ser
145                 150                 155                 160

GGT GTC TAT GCT GGT GAT CCT TCT AAG CTC AGC ATG AAG GCT GCA TTT         528
Gly Val Tyr Ala Gly Asp Pro Ser Lys Leu Ser Met Lys Ala Ala Phe
                165                 170                 175

GGG AAG GTT TGG CGG TTG GAA GAA ACT GGA GGT AGT ATT ATT GGT GGA         576
Gly Lys Val Trp Arg Leu Glu Glu Thr Gly Gly Ser Ile Ile Gly Gly
                180                 185                 190

ACC ATC AAG ACA ATT CAG GAG AGG AGC AAG AAT CCA AAA CCA CCG AGG         624
Thr Ile Lys Thr Ile Gln Glu Arg Ser Lys Asn Pro Lys Pro Pro Arg
            195                 200                 205

GAT GCC CGC CTT CCG AAG CCA AAA GGG CAG ACA GTT GCA TCT TTC AGG         672
Asp Ala Arg Leu Pro Lys Pro Lys Gly Gln Thr Val Ala Ser Phe Arg
            210                 215                 220

AAG GGT CTT GCC ATG CTT CCA AAT GCC ATT ACA TCC AGC TTG GGT AGT         720
Lys Gly Leu Ala Met Leu Pro Asn Ala Ile Thr Ser Ser Leu Gly Ser
225                 230                 235                 240

AAA GTC AAA CTA TCA TGG AAA CTC ACG AGC ATT ACA AAA TCA GAT GAC         768
Lys Val Lys Leu Ser Trp Lys Leu Thr Ser Ile Thr Lys Ser Asp Asp
                245                 250                 255

AAG GGA TAT GTT TTG GAG TAT GAA ACG CCA GAA GGG GTT GTT TCG GTG         816
Lys Gly Tyr Val Leu Glu Tyr Glu Thr Pro Glu Gly Val Val Ser Val
                260                 265                 270

CAG GCT AAA AGT GTT ATC ATG ACT ATT CCA TCA TAT GTT GCT AGC AAC         864
Gln Ala Lys Ser Val Ile Met Thr Ile Pro Ser Tyr Val Ala Ser Asn
            275                 280                 285

ATT TTG CGT CCA CTT TCA AGC GAT GCT GCA GAT GCT CTA TCA AGA TTC         912
Ile Leu Arg Pro Leu Ser Ser Asp Ala Ala Asp Ala Leu Ser Arg Phe
            290                 295                 300

TAT TAT CCA CCG GTT GCT GCT GTA ACT GTT TCG TAT CCA AAG GAA GCA         960
Tyr Tyr Pro Pro Val Ala Ala Val Thr Val Ser Tyr Pro Lys Glu Ala
305                 310                 315                 320

ATT AGA AAA GAA TGC TTA ATT GAT GGG GAA CTC CAG GGC TTT GGC CAG        1008
Ile Arg Lys Glu Cys Leu Ile Asp Gly Glu Leu Gln Gly Phe Gly Gln
                325                 330                 335

TTG CAT CCA CGT AGT CAA GGA GTT GAG ACA TTA GGA ACA ATA TAC AGT        1056
Leu His Pro Arg Ser Gln Gly Val Glu Thr Leu Gly Thr Ile Tyr Ser
            340                 345                 350

TCC TCA CTC TTT CCA AAT CGT GCT CCT GAC GGT AGG GTG TTA CTT CTA        1104
Ser Ser Leu Phe Pro Asn Arg Ala Pro Asp Gly Arg Val Leu Leu Leu
            355                 360                 365

AAC TAC ATA GGA GGT GCT ACA AAC ACA GGA ATT GTT TCC AAG ACT GAA        1152
Asn Tyr Ile Gly Gly Ala Thr Asn Thr Gly Ile Val Ser Lys Thr Glu
370                 375                 380

AGT GAG CTG GTC GAA GCA GTT GAC CGT GAC CTC CGA AAA ATG CTT ATA        1200
```

```
Ser Glu Leu Val Glu Ala Val Asp Arg Asp Leu Arg Lys Met Leu Ile
385                 390                 395                 400

AAT TCT ACA GCA GTG GAC CCT TTA GTC CTT GGT GTT CGA GTT TGG CCA          1248
Asn Ser Thr Ala Val Asp Pro Leu Val Leu Gly Val Arg Val Trp Pro
                    405                 410                 415

CAA GCC ATA CCT CAG TTC CTG GTA GGA CAT CTT GAT CTT CTG GAA GCC          1296
Gln Ala Ile Pro Gln Phe Leu Val Gly His Leu Asp Leu Leu Glu Ala
                420                 425                 430

GCA AAA GCT GCC CTG GAC CGA GGT GGC TAC GAT GGG CTG TTC CTA GGA          1344
Ala Lys Ala Ala Leu Asp Arg Gly Gly Tyr Asp Gly Leu Phe Leu Gly
            435                 440                 445

GGG AAC TAT GTT GCA GGA GTT GCC CTG GGC AGA TGC GTT GAG GGC GCG          1392
Gly Asn Tyr Val Ala Gly Val Ala Leu Gly Arg Cys Val Glu Gly Ala
        450                 455                 460

TAT GAA AGT GCC TCG CAA ATA TCT GAC TTC TTG ACC AAG TAT GCC TAC          1440
Tyr Glu Ser Ala Ser Gln Ile Ser Asp Phe Leu Thr Lys Tyr Ala Tyr
465                 470                 475                 480

AAG TGATGAAAGA AGTGGAGCGC TACTTGTTAA TCGTTTATGT TGCATAGATG               1493
Lys

AGGTGCCTCC GGGAAAAAAA AAGCTTGAAT AGTATTTTTT ATTCTTATTT TGTAAATTGC        1553

ATTTCTGTTC TTTTTTCTAT CAGTAATTAG TTATATTTTA GTTCTGTAGG AGATTGTTCT        1613

GTTCACTGCC CTTCAAAAGA AATTTTATTT TTCATTCTTT TATGAGAGCT GTGCTACTTA        1673

AAAAAAAAAA AAAAAAAA                                                      1691

(2) INFORMATION FOR SEQ ID NO:6:

(i) SEQUENCE CHARACTERISTICS:
        (A) LENGTH: 481 amino acids
        (B) TYPE: amino acid
        (D) TOPOLOGY: linear (ii) MOLECULE TYPE: protein (xi) SEQUENCE DESCRIPTION: SEQ ID NO:6:

Ala Asp Cys Val Val Gly Gly Gly Ile Ser Gly Leu Cys Thr Ala
1               5                   10                  15

Gln Ala Leu Ala Thr Arg His Gly Val Gly Asp Val Leu Val Thr Glu
            20                  25                  30

Ala Arg Ala Arg Pro Gly Gly Asn Ile Thr Thr Val Glu Arg Pro Glu
        35                  40                  45

Glu Gly Tyr Leu Trp Glu Glu Gly Pro Asn Ser Phe Gln Pro Ser Asp
    50                  55                  60

Pro Val Leu Thr Met Ala Val Asp Ser Gly Leu Lys Asp Asp Leu Val
65                  70                  75                  80

Phe Gly Asp Pro Asn Ala Pro Arg Phe Val Leu Trp Glu Gly Lys Leu
                85                  90                  95

Arg Pro Val Pro Ser Lys Pro Ala Asp Leu Pro Phe Phe Asp Leu Met
            100                 105                 110

Ser Ile Pro Gly Lys Leu Arg Ala Gly Leu Gly Ala Leu Gly Ile Arg
        115                 120                 125

Pro Pro Pro Pro Gly Arg Glu Glu Ser Val Glu Glu Phe Val Arg Arg
    130                 135                 140

Asn Leu Gly Ala Glu Val Phe Glu Arg Leu Ile Glu Pro Phe Cys Ser
145                 150                 155                 160

Gly Val Tyr Ala Gly Asp Pro Ser Lys Leu Ser Met Lys Ala Ala Phe
                165                 170                 175

Gly Lys Val Trp Arg Leu Glu Glu Thr Gly Gly Ser Ile Ile Gly Gly
```

```
                180                 185                 190
Thr Ile Lys Thr Ile Gln Glu Arg Ser Lys Asn Pro Lys Pro Pro Arg
            195                 200                 205
Asp Ala Arg Leu Pro Lys Pro Lys Gly Gln Thr Val Ala Ser Phe Arg
210                 215                 220
Lys Gly Leu Ala Met Leu Pro Asn Ala Ile Thr Ser Ser Leu Gly Ser
225                 230                 235                 240
Lys Val Lys Leu Ser Trp Lys Leu Thr Ser Ile Thr Lys Ser Asp Asp
                245                 250                 255
Lys Gly Tyr Val Leu Glu Tyr Glu Thr Pro Glu Gly Val Val Ser Val
            260                 265                 270
Gln Ala Lys Ser Val Ile Met Thr Ile Pro Ser Tyr Val Ala Ser Asn
        275                 280                 285
Ile Leu Arg Pro Leu Ser Ser Asp Ala Ala Asp Ala Leu Ser Arg Phe
290                 295                 300
Tyr Tyr Pro Pro Val Ala Ala Val Thr Val Ser Tyr Pro Lys Glu Ala
305                 310                 315                 320
Ile Arg Lys Glu Cys Leu Ile Asp Gly Glu Leu Gln Gly Phe Gly Gln
                325                 330                 335
Leu His Pro Arg Ser Gln Gly Val Glu Thr Leu Gly Thr Ile Tyr Ser
            340                 345                 350
Ser Ser Leu Phe Pro Asn Arg Ala Pro Asp Gly Arg Val Leu Leu Leu
        355                 360                 365
Asn Tyr Ile Gly Gly Ala Thr Asn Thr Gly Ile Val Ser Lys Thr Glu
370                 375                 380
Ser Glu Leu Val Glu Ala Val Asp Arg Asp Leu Arg Lys Met Leu Ile
385                 390                 395                 400
Asn Ser Thr Ala Val Asp Pro Leu Val Leu Gly Val Arg Val Trp Pro
                405                 410                 415
Gln Ala Ile Pro Gln Phe Leu Val Gly His Leu Asp Leu Leu Glu Ala
            420                 425                 430
Ala Lys Ala Ala Leu Asp Arg Gly Gly Tyr Asp Gly Leu Phe Leu Gly
        435                 440                 445
Gly Asn Tyr Val Ala Gly Val Ala Leu Gly Arg Cys Val Glu Gly Ala
450                 455                 460
Tyr Glu Ser Ala Ser Gln Ile Ser Asp Phe Leu Thr Lys Tyr Ala Tyr
465                 470                 475                 480
Lys (2) INFORMATION FOR SEQ ID NO:7:

(i) SEQUENCE CHARACTERISTICS:
        (A) LENGTH: 2061 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Zea mays (maize)

(vii) IMMEDIATE SOURCE:
        (B) CLONE: pWDC-3 (NRRL B-21259)

(ix) FEATURE:
```

(A) NAME/KEY: CDS
(B) LOCATION: 64..1698
(D) OTHER INFORMATION: /product= "Maize protox-2"

(xi) SEQUENCE DESCRIPTION: SEQ ID NO:7:

```
CTCTCCTACC TCCACCTCCA CGACAACAAG CAAATCCCCA TCCAGTTCCA AACCCTAACT          60

CAA ATG CTC GCT TTG ACT GCC TCA GCC TCA TCC GCT TCG TCC CAT CCT          108
    Met Leu Ala Leu Thr Ala Ser Ala Ser Ser Ala Ser Ser His Pro
    1               5                   10                  15

TAT CGC CAC GCC TCC GCG CAC ACT CGT CGC CCC CGC CTA CGT GCG GTC          156
Tyr Arg His Ala Ser Ala His Thr Arg Arg Pro Arg Leu Arg Ala Val
                20                  25                  30

CTC GCG ATG GCG GGC TCC GAC GAC CCC CGT GCA GCG CCC GCC AGA TCG          204
Leu Ala Met Ala Gly Ser Asp Asp Pro Arg Ala Ala Pro Ala Arg Ser
            35                  40                  45

GTC GCC GTC GTC GGC GCC GGG GTC AGC GGG CTC GCG GCG GCG TAC AGG          252
Val Ala Val Val Gly Ala Gly Val Ser Gly Leu Ala Ala Ala Tyr Arg
        50                  55                  60

CTC AGA CAG AGC GGC GTG AAC GTA ACG GTG TTC GAA GCG GCC GAC AGG          300
Leu Arg Gln Ser Gly Val Asn Val Thr Val Phe Glu Ala Ala Asp Arg
    65                  70                  75

GCG GGA GGA AAG ATA CGG ACC AAT TCC GAG GGC GGG TTT GTC TGG GAT          348
Ala Gly Gly Lys Ile Arg Thr Asn Ser Glu Gly Gly Phe Val Trp Asp
80                  85                  90                  95

GAA GGA GCT AAC ACC ATG ACA GAA GGT GAA TGG GAG GCC AGT AGA CTG          396
Glu Gly Ala Asn Thr Met Thr Glu Gly Glu Trp Glu Ala Ser Arg Leu
                100                 105                 110

ATT GAT GAT CTT GGT CTA CAA GAC AAA CAG CAG TAT CCT AAC TCC CAA          444
Ile Asp Asp Leu Gly Leu Gln Asp Lys Gln Gln Tyr Pro Asn Ser Gln
            115                 120                 125

CAC AAG CGT TAC ATT GTC AAA GAT GGA GCA CCA GCA CTG ATT CCT TCG          492
His Lys Arg Tyr Ile Val Lys Asp Gly Ala Pro Ala Leu Ile Pro Ser
        130                 135                 140

GAT CCC ATT TCG CTA ATG AAA AGC AGT GTT CTT TCG ACA AAA TCA AAG          540
Asp Pro Ile Ser Leu Met Lys Ser Ser Val Leu Ser Thr Lys Ser Lys
    145                 150                 155

ATT GCG TTA TTT TTT GAA CCA TTT CTC TAC AAG AAA GCT AAC ACA AGA          588
Ile Ala Leu Phe Phe Glu Pro Phe Leu Tyr Lys Lys Ala Asn Thr Arg
160                 165                 170                 175

AAC TCT GGA AAA GTG TCT GAG GAG CAC TTG AGT GAG AGT GTT GGG AGC          636
Asn Ser Gly Lys Val Ser Glu Glu His Leu Ser Glu Ser Val Gly Ser
                180                 185                 190

TTC TGT GAA CGC CAC TTT GGA AGA GAA GTT GTT GAC TAT TTT GTT GAT          684
Phe Cys Glu Arg His Phe Gly Arg Glu Val Val Asp Tyr Phe Val Asp
            195                 200                 205

CCA TTT GTA GCT GGA ACA AGT GCA GGA GAT CCA GAG TCA CTA TCT ATT          732
Pro Phe Val Ala Gly Thr Ser Ala Gly Asp Pro Glu Ser Leu Ser Ile
        210                 215                 220

CGT CAT GCA TTC CCA GCA TTG TGG AAT TTG GAA AGA AAG TAT GGT TCA          780
Arg His Ala Phe Pro Ala Leu Trp Asn Leu Glu Arg Lys Tyr Gly Ser
    225                 230                 235

GTT ATT GTT GGT GCC ATC TTG TCT AAG CTA GCA GCT AAA GGT GAT CCA          828
Val Ile Val Gly Ala Ile Leu Ser Lys Leu Ala Ala Lys Gly Asp Pro
240                 245                 250                 255

GTA AAG ACA AGA CAT GAT TCA TCA GGG AAA AGA AGG AAT AGA CGA GTG          876
Val Lys Thr Arg His Asp Ser Ser Gly Lys Arg Arg Asn Arg Arg Val
                260                 265                 270

TCG TTT TCA TTT CAT GGT GGA ATG CAG TCA CTA ATA AAT GCA CTT CAC          924
Ser Phe Ser Phe His Gly Gly Met Gln Ser Leu Ile Asn Ala Leu His
            275                 280                 285
```

```
AAT GAA GTT GGA GAT GAT AAT GTG AAG CTT GGT ACA GAA GTG TTG TCA        972
Asn Glu Val Gly Asp Asp Asn Val Lys Leu Gly Thr Glu Val Leu Ser
            290                 295                 300

TTG GCA TGT ACA TTT GAT GGA GTT CCT GCA CTA GGC AGG TGG TCA ATT       1020
Leu Ala Cys Thr Phe Asp Gly Val Pro Ala Leu Gly Arg Trp Ser Ile
305                 310                 315

TCT GTT GAT TCG AAG GAT AGC GGT GAC AAG GAC CTT GCT AGT AAC CAA       1068
Ser Val Asp Ser Lys Asp Ser Gly Asp Lys Asp Leu Ala Ser Asn Gln
320                 325                 330                 335

ACC TTT GAT GCT GTT ATA ATG ACA GCT CCA TTG TCA AAT GTC CGG AGG       1116
Thr Phe Asp Ala Val Ile Met Thr Ala Pro Leu Ser Asn Val Arg Arg
                340                 345                 350

ATG AAG TTC ACC AAA GGT GGA GCT CCG GTT GTT CTT GAC TTT CTT CCT       1164
Met Lys Phe Thr Lys Gly Gly Ala Pro Val Val Leu Asp Phe Leu Pro
            355                 360                 365

AAG ATG GAT TAT CTA CCA CTA TCT CTC ATG GTG ACT GCT TTT AAG AAG       1212
Lys Met Asp Tyr Leu Pro Leu Ser Leu Met Val Thr Ala Phe Lys Lys
        370                 375                 380

GAT GAT GTC AAG AAA CCT CTG GAA GGA TTT GGG GTC TTA ATA CCT TAC       1260
Asp Asp Val Lys Lys Pro Leu Glu Gly Phe Gly Val Leu Ile Pro Tyr
385                 390                 395

AAG GAA CAG CAA AAA CAT GGT CTG AAA ACC CTT GGG ACT CTC TTT TCC       1308
Lys Glu Gln Gln Lys His Gly Leu Lys Thr Leu Gly Thr Leu Phe Ser
400                 405                 410                 415

TCA ATG ATG TTC CCA GAT CGA GCT CCT GAT GAC CAA TAT TTA TAT ACA       1356
Ser Met Met Phe Pro Asp Arg Ala Pro Asp Asp Gln Tyr Leu Tyr Thr
                420                 425                 430

ACA TTT GTT GGG GGT AGC CAC AAT AGA GAT CTT GCT GGA GCT CCA ACG       1404
Thr Phe Val Gly Gly Ser His Asn Arg Asp Leu Ala Gly Ala Pro Thr
            435                 440                 445

TCT ATT CTG AAA CAA CTT GTG ACC TCT GAC CTT AAA AAA CTC TTG GGC       1452
Ser Ile Leu Lys Gln Leu Val Thr Ser Asp Leu Lys Lys Leu Leu Gly
        450                 455                 460

GTA GAG GGG CAA CCA ACT TTT GTC AAG CAT GTA TAC TGG GGA AAT GCT       1500
Val Glu Gly Gln Pro Thr Phe Val Lys His Val Tyr Trp Gly Asn Ala
465                 470                 475

TTT CCT TTG TAT GGC CAT GAT TAT AGT TCT GTA TTG GAA GCT ATA GAA       1548
Phe Pro Leu Tyr Gly His Asp Tyr Ser Ser Val Leu Glu Ala Ile Glu
480                 485                 490                 495

AAG ATG GAG AAA AAC CTT CCA GGG TTC TTC TAC GCA GGA AAT AGC AAG       1596
Lys Met Glu Lys Asn Leu Pro Gly Phe Phe Tyr Ala Gly Asn Ser Lys
                500                 505                 510

GAT GGG CTT GCT GTT GGA AGT GTT ATA GCT TCA GGA AGC AAG GCT GCT       1644
Asp Gly Leu Ala Val Gly Ser Val Ile Ala Ser Gly Ser Lys Ala Ala
            515                 520                 525

GAC CTT GCA ATC TCA TAT CTT GAA TCT CAC ACC AAG CAT AAT AAT TCA       1692
Asp Leu Ala Ile Ser Tyr Leu Glu Ser His Thr Lys His Asn Asn Ser
        530                 535                 540

CAT TGAAAGTGTC TGACCTATCC TCTAGCAGTT GTCGACAAAT TCTCCAGTT             1745
His
545

CATGTACAGT AGAAACCGAT GCGTTGCAGT TTCAGAACAT CTTCACTTCT TCAGATATTA     1805

ACCCTTCGTT GAACATCCAC CAGAAAGGTA GTCACATGTG TAAGTGGGAA AATGAGGTTA     1865

AAAACTATTA TGGCGGCCGA ATGTTCCTT TTTGTTTTCC TCACAAGTGG CCTACGACAC      1925

TTGATGTTGG AAATACATTT AAATTTGTTG AATTGTTTGA GAACACATGC GTGACGTGTA     1985

ATATTTGCCT ATTGTGATTT TAGCAGTAGT CTTGGCCAGA TTATGCTTTA CGCCTTTAAA     2045

AAAAAAAAAA AAAAA                                                     2061
```

(2) INFORMATION FOR SEQ ID NO:8:

(i) SEQUENCE CHARACTERISTICS:
　　　　(A) LENGTH: 544 amino acids
　　　　(B) TYPE: amino acid
　　　　(D) TOPOLOGY: linear (ii) MOLECULE TYPE: protein (xi) SEQUENCE DESCRIPTION: SEQ ID NO:8:

```
Met Leu Ala Leu Thr Ala Ser Ala Ser Ser Ala Ser Ser His Pro Tyr
 1               5                  10                  15

Arg His Ala Ser Ala His Thr Arg Arg Pro Arg Leu Arg Ala Val Leu
            20                  25                  30

Ala Met Ala Gly Ser Asp Asp Pro Arg Ala Ala Pro Ala Arg Ser Val
        35                  40                  45

Ala Val Val Gly Ala Gly Val Ser Gly Leu Ala Ala Tyr Arg Leu
    50                  55                  60

Arg Gln Ser Gly Val Asn Val Thr Val Phe Glu Ala Ala Asp Arg Ala
 65                 70                  75                  80

Gly Gly Lys Ile Arg Thr Asn Ser Glu Gly Gly Phe Val Trp Asp Glu
                85                  90                  95

Gly Ala Asn Thr Met Thr Glu Gly Glu Trp Glu Ala Ser Arg Leu Ile
            100                 105                 110

Asp Asp Leu Gly Leu Gln Asp Lys Gln Gln Tyr Pro Asn Ser Gln His
            115                 120                 125

Lys Arg Tyr Ile Val Lys Asp Gly Ala Pro Ala Leu Ile Pro Ser Asp
130                 135                 140

Pro Ile Ser Leu Met Lys Ser Ser Val Leu Ser Thr Lys Ser Lys Ile
145                 150                 155                 160

Ala Leu Phe Phe Glu Pro Phe Leu Tyr Lys Lys Ala Asn Thr Arg Asn
                165                 170                 175

Ser Gly Lys Val Ser Glu Glu His Leu Ser Glu Ser Val Gly Ser Phe
            180                 185                 190

Cys Glu Arg His Phe Gly Arg Glu Val Val Asp Tyr Phe Val Asp Pro
            195                 200                 205

Phe Val Ala Gly Thr Ser Ala Gly Asp Pro Glu Ser Leu Ser Ile Arg
    210                 215                 220

His Ala Phe Pro Ala Leu Trp Asn Leu Glu Arg Lys Tyr Gly Ser Val
225                 230                 235                 240

Ile Val Gly Ala Ile Leu Ser Lys Leu Ala Ala Lys Gly Asp Pro Val
                245                 250                 255

Lys Thr Arg His Asp Ser Ser Gly Lys Arg Arg Asn Arg Arg Val Ser
            260                 265                 270

Phe Ser Phe His Gly Gly Met Gln Ser Leu Ile Asn Ala Leu His Asn
        275                 280                 285

Glu Val Gly Asp Asp Asn Val Lys Leu Gly Thr Glu Val Leu Ser Leu
    290                 295                 300

Ala Cys Thr Phe Asp Gly Val Pro Ala Leu Gly Arg Trp Ser Ile Ser
305                 310                 315                 320

Val Asp Ser Lys Asp Ser Gly Asp Lys Asp Leu Ala Ser Asn Gln Thr
                325                 330                 335

Phe Asp Ala Val Ile Met Thr Ala Pro Leu Ser Asn Val Arg Arg Met
            340                 345                 350

Lys Phe Thr Lys Gly Gly Ala Pro Val Val Leu Asp Phe Leu Pro Lys
```

-continued

```
                355                 360                 365
Met Asp Tyr Leu Pro Leu Ser Leu Met Val Thr Ala Phe Lys Lys Asp
    370                 375                 380

Asp Val Lys Lys Pro Leu Glu Gly Phe Gly Val Leu Ile Pro Tyr Lys
385                 390                 395                 400

Glu Gln Gln Lys His Gly Leu Lys Thr Leu Gly Thr Leu Phe Ser Ser
                405                 410                 415

Met Met Phe Pro Asp Arg Ala Pro Asp Gln Tyr Leu Tyr Thr Thr
                420                 425                 430

Phe Val Gly Gly Ser His Asn Arg Asp Leu Ala Gly Ala Pro Thr Ser
                435                 440                 445

Ile Leu Lys Gln Leu Val Thr Ser Asp Leu Lys Lys Leu Leu Gly Val
450                 455                 460

Glu Gly Gln Pro Thr Phe Val Lys His Val Tyr Trp Gly Asn Ala Phe
465                 470                 475                 480

Pro Leu Tyr Gly His Asp Tyr Ser Ser Val Leu Glu Ala Ile Glu Lys
                485                 490                 495

Met Glu Lys Asn Leu Pro Gly Phe Phe Tyr Ala Gly Asn Ser Lys Asp
                500                 505                 510

Gly Leu Ala Val Gly Ser Val Ile Ala Ser Gly Ser Lys Ala Ala Asp
                515                 520                 525

Leu Ala Ile Ser Tyr Leu Glu Ser His Thr Lys His Asn Asn Ser His
                530                 535                 540
```

(2) INFORMATION FOR SEQ ID NO:9:

(i) SEQUENCE CHARACTERISTICS:
        (A) LENGTH: 1811 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Triticum aestivum (wheat)

(vii) IMMEDIATE SOURCE:
        (B) CLONE: pWDC-13 (NRRL B-21545)

(ix) FEATURE:
        (A) NAME/KEY: CDS
        (B) LOCATION: 3..1589
        (D) OTHER INFORMATION: /product= "wheat protox-1"

(xi) SEQUENCE DESCRIPTION: SEQ ID NO:9:

```
GC GCA ACA ATG GCC ACC GCC ACC GTC GCG GCC GCG TCG CCG CTC CGC        47
   Ala Thr Met Ala Thr Ala Thr Val Ala Ala Ala Ser Pro Leu Arg
   1               5                  10                  15

GGC AGG GTC ACC GGG CGC CCA CAC CGC GTC CGC CCG CGT TGC GCT ACC       95
Gly Arg Val Thr Gly Arg Pro His Arg Val Arg Pro Arg Cys Ala Thr
             20                  25                  30

GCG AGC AGC GCG ACC GAG ACT CCG GCG GCG CCC GGC GTG CGG CTG TCC      143
Ala Ser Ser Ala Thr Glu Thr Pro Ala Ala Pro Gly Val Arg Leu Ser
             35                  40                  45

GCG GAA TGC GTC ATT GTG GGC GCC GGC ATC AGC GGC CTC TGC ACC GCG      191
Ala Glu Cys Val Ile Val Gly Ala Gly Ile Ser Gly Leu Cys Thr Ala
             50                  55                  60

CAG GCG CTG GCC ACC CGA TAC GGC GTC AGC GAC CTC CTC GTC ACG GAG      239
Gln Ala Leu Ala Thr Arg Tyr Gly Val Ser Asp Leu Leu Val Thr Glu
```

```
            65                  70                  75
GCC CGC GAC CGC CCG GGC GGC AAC ATC ACC ACC GTC GAG CGT CCC GAC      287
Ala Arg Asp Arg Pro Gly Gly Asn Ile Thr Thr Val Glu Arg Pro Asp
 80                  85                  90                  95

GAG GGG TAC CTG TGG GAG GAG GGA CCC AAC AGC TTC CAG CCC TCC GAC      335
Glu Gly Tyr Leu Trp Glu Glu Gly Pro Asn Ser Phe Gln Pro Ser Asp
                    100                 105                 110

CCG GTC CTC ACC ATG GCC GTG GAC AGC GGG CTC AAG GAT GAC TTG GTG      383
Pro Val Leu Thr Met Ala Val Asp Ser Gly Leu Lys Asp Asp Leu Val
                115                 120                 125

TTC GGG GAC CCC AAC GCG CCC CGG TTC GTG CTG TGG GAG GGG AAG CTG      431
Phe Gly Asp Pro Asn Ala Pro Arg Phe Val Leu Trp Glu Gly Lys Leu
            130                 135                 140

AGG CCG GTG CCG TCG AAG CCA GGC GAC CTG CCT TTC TTC AGC CTC ATG      479
Arg Pro Val Pro Ser Lys Pro Gly Asp Leu Pro Phe Phe Ser Leu Met
        145                 150                 155

AGT ATC CCT GGG AAG CTC AGG GCC GGC CTT GGC GCG CTC GGC ATT CGC      527
Ser Ile Pro Gly Lys Leu Arg Ala Gly Leu Gly Ala Leu Gly Ile Arg
160                 165                 170                 175

CCA CCT CCT CCA GGG CGC GAG GAG TCG GTG GAG GAG TTT GTG CGC CGC      575
Pro Pro Pro Pro Gly Arg Glu Glu Ser Val Glu Glu Phe Val Arg Arg
                    180                 185                 190

AAC CTC GGT GCC GAG GTC TTT GAG CGC CTC ATC GAG CCT TTC TGC TCA      623
Asn Leu Gly Ala Glu Val Phe Glu Arg Leu Ile Glu Pro Phe Cys Ser
                195                 200                 205

GGT GTA TAT GCT GGT GAT CCT TCG AAG CTT AGT ATG AAG GCT GCA TTT      671
Gly Val Tyr Ala Gly Asp Pro Ser Lys Leu Ser Met Lys Ala Ala Phe
            210                 215                 220

GGG AAG GTC TGG AGG TTG GAG GAG ATT GGA GGT AGT ATT ATT GGT GGA      719
Gly Lys Val Trp Arg Leu Glu Glu Ile Gly Gly Ser Ile Ile Gly Gly
        225                 230                 235

ACC ATC AAG GCG ATT CAG GAT AAA GGG AAG AAC CCC AAA CCG CCA AGG      767
Thr Ile Lys Ala Ile Gln Asp Lys Gly Lys Asn Pro Lys Pro Pro Arg
240                 245                 250                 255

GAT CCC CGA CTT CCG GCA CCA AAG GGA CAG ACG GTG GCA TCT TTC AGG      815
Asp Pro Arg Leu Pro Ala Pro Lys Gly Gln Thr Val Ala Ser Phe Arg
                    260                 265                 270

AAG GGT CTA GCC ATG CTC CCG AAT GCC ATC GCA TCT AGG CTG GGT AGT      863
Lys Gly Leu Ala Met Leu Pro Asn Ala Ile Ala Ser Arg Leu Gly Ser
                275                 280                 285

AAA GTC AAG CTG TCA TGG AAG CTT ACG AGC ATT ACA AAG GCG GAC AAC      911
Lys Val Lys Leu Ser Trp Lys Leu Thr Ser Ile Thr Lys Ala Asp Asn
            290                 295                 300

CAA GGA TAT GTA TTA GGT TAT GAA ACA CCA GAA GGA CTT GTT TCA GTG      959
Gln Gly Tyr Val Leu Gly Tyr Glu Thr Pro Glu Gly Leu Val Ser Val
        305                 310                 315

CAG GCT AAA AGT GTT ATC ATG ACC ATC CCG TCA TAT GTT GCT AGT GAT     1007
Gln Ala Lys Ser Val Ile Met Thr Ile Pro Ser Tyr Val Ala Ser Asp
320                 325                 330                 335

ATC TTG CGC CCA CTT TCA ATT GAT GCA GCA GAT GCA CTC TCA AAA TTC     1055
Ile Leu Arg Pro Leu Ser Ile Asp Ala Ala Asp Ala Leu Ser Lys Phe
                    340                 345                 350

TAT TAT CCG CCA GTT GCT GCT GTA ACT GTT TCA TAT CCA AAA GAA GCT     1103
Tyr Tyr Pro Pro Val Ala Ala Val Thr Val Ser Tyr Pro Lys Glu Ala
                355                 360                 365

ATT AGA AAA GAA TGC TTA ATT GAT GGG GAG CTC CAG GGT TTC GGC CAG     1151
Ile Arg Lys Glu Cys Leu Ile Asp Gly Glu Leu Gln Gly Phe Gly Gln
            370                 375                 380

TTG CAT CCA CGT AGC CAA GGA GTC GAG ACT TTA GGG ACA ATA TAT AGC     1199
Leu His Pro Arg Ser Gln Gly Val Glu Thr Leu Gly Thr Ile Tyr Ser
```

```
                    385                 390                 395
TCT TCT CTC TTT CCT AAT CGT GCT CCT GCT GGA AGA GTG TTA CTT CTG        1247
Ser Ser Leu Phe Pro Asn Arg Ala Pro Ala Gly Arg Val Leu Leu Leu
400                 405                 410                 415

AAC TAT ATC GGG GGT TCT ACA AAT ACA GGG ATC GTC TCC AAG ACT GAG        1295
Asn Tyr Ile Gly Gly Ser Thr Asn Thr Gly Ile Val Ser Lys Thr Glu
                    420                 425                 430

AGT GAC TTA GTA GGA GCC GTT GAC CGT GAC CTC AGA AAA ATG TTG ATA        1343
Ser Asp Leu Val Gly Ala Val Asp Arg Asp Leu Arg Lys Met Leu Ile
                    435                 440                 445

AAC CCT AGA GCA GCA GAC CCT TTA GCA TTA GGG GTT CGA GTG TGG CCA        1391
Asn Pro Arg Ala Ala Asp Pro Leu Ala Leu Gly Val Arg Val Trp Pro
                450                 455                 460

CAA GCA ATA CCA CAG TTT TTG ATT GGG CAC CTT GAT CGC CTT GCT GCT        1439
Gln Ala Ile Pro Gln Phe Leu Ile Gly His Leu Asp Arg Leu Ala Ala
465                 470                 475

GCA AAA TCT GCA CTG GGC CAA GGC GGC TAC GAC GGG TTG TTC CTA GGA        1487
Ala Lys Ser Ala Leu Gly Gln Gly Gly Tyr Asp Gly Leu Phe Leu Gly
480                 485                 490                 495

GGA AAC TAC GTC GCA GGA GTT GCC TTG GGC CGA TGC ATC GAG GGT GCG        1535
Gly Asn Tyr Val Ala Gly Val Ala Leu Gly Arg Cys Ile Glu Gly Ala
                    500                 505                 510

TAC GAG AGT GCC TCA CAA GTA TCT GAC TTC TTG ACC AAG TAT GCC TAC        1583
Tyr Glu Ser Ala Ser Gln Val Ser Asp Phe Leu Thr Lys Tyr Ala Tyr
                515                 520                 525

AAG TGA TGGAAGTAGT GCATCTCTTC ATTTTGTTGC ATATACGAGG TGAGGCTAGG        1639
Lys

ATCGGTAAAA CATCATGAGA TTCTGTAGTG TTTCTTTAAT TGAAAAAACA AATTTTAGTG    1699

ATGCAATATG TGCTCTTTCC TGTAGTTCGA GCATGTACAT CGGTATGGGA TAAAGTAGAA    1759

TAAGCTATTC TGCAAAAGCA GTGATTTTTT TTGAAAAAAA AAAAAAAAA AA             1811
```

(2) INFORMATION FOR SEQ ID NO:10:

(i) SEQUENCE CHARACTERISTICS:
        (A) LENGTH: 528 amino acids
        (B) TYPE: amino acid
        (D) TOPOLOGY: linear (ii) MOLECULE TYPE: protein (xi) SEQUENCE DESCRIPTION: SEQ ID NO:10:

```
Ala Thr Met Ala Thr Ala Thr Val Ala Ala Ala Ser Pro Leu Arg Gly
1               5                   10                  15

Arg Val Thr Gly Arg Pro His Arg Val Arg Pro Arg Cys Ala Thr Ala
                20                  25                  30

Ser Ser Ala Thr Glu Thr Pro Ala Ala Pro Gly Val Arg Leu Ser Ala
            35                  40                  45

Glu Cys Val Ile Val Gly Ala Gly Ile Ser Gly Leu Cys Thr Ala Gln
        50                  55                  60

Ala Leu Ala Thr Arg Tyr Gly Val Ser Asp Leu Leu Val Thr Glu Ala
65                  70                  75                  80

Arg Asp Arg Pro Gly Gly Asn Ile Thr Thr Val Glu Arg Pro Asp Glu
                85                  90                  95

Gly Tyr Leu Trp Glu Glu Gly Pro Asn Ser Phe Gln Pro Ser Asp Pro
            100                 105                 110

Val Leu Thr Met Ala Val Asp Ser Gly Leu Lys Asp Asp Leu Val Phe
        115                 120                 125

Gly Asp Pro Asn Ala Pro Arg Phe Val Leu Trp Glu Gly Lys Leu Arg
```

```
             130                 135                 140
Pro Val Pro Ser Lys Pro Gly Asp Leu Pro Phe Phe Ser Leu Met Ser
145                 150                 155                 160

Ile Pro Gly Lys Leu Arg Ala Gly Leu Gly Ala Leu Gly Ile Arg Pro
                165                 170                 175

Pro Pro Pro Gly Arg Glu Glu Ser Val Glu Glu Phe Val Arg Arg Asn
            180                 185                 190

Leu Gly Ala Glu Val Phe Glu Arg Leu Ile Glu Pro Phe Cys Ser Gly
        195                 200                 205

Val Tyr Ala Gly Asp Pro Ser Lys Leu Ser Met Lys Ala Ala Phe Gly
210                 215                 220

Lys Val Trp Arg Leu Glu Glu Ile Gly Gly Ser Ile Ile Gly Gly Thr
225                 230                 235                 240

Ile Lys Ala Ile Gln Asp Lys Gly Lys Asn Pro Lys Pro Pro Arg Asp
                245                 250                 255

Pro Arg Leu Pro Ala Pro Lys Gly Gln Thr Val Ala Ser Phe Arg Lys
            260                 265                 270

Gly Leu Ala Met Leu Pro Asn Ala Ile Ala Ser Arg Leu Gly Ser Lys
        275                 280                 285

Val Lys Leu Ser Trp Lys Leu Thr Ser Ile Thr Lys Ala Asp Asn Gln
290                 295                 300

Gly Tyr Val Leu Gly Tyr Glu Thr Pro Glu Gly Leu Val Ser Val Gln
305                 310                 315                 320

Ala Lys Ser Val Ile Met Thr Ile Pro Ser Tyr Val Ala Ser Asp Ile
                325                 330                 335

Leu Arg Pro Leu Ser Ile Asp Ala Ala Asp Ala Leu Ser Lys Phe Tyr
            340                 345                 350

Tyr Pro Pro Val Ala Ala Val Thr Val Ser Tyr Pro Lys Glu Ala Ile
        355                 360                 365

Arg Lys Glu Cys Leu Ile Asp Gly Glu Leu Gln Gly Phe Gly Gln Leu
370                 375                 380

His Pro Arg Ser Gln Gly Val Glu Thr Leu Gly Thr Ile Tyr Ser Ser
385                 390                 395                 400

Ser Leu Phe Pro Asn Arg Ala Pro Ala Gly Arg Val Leu Leu Leu Asn
                405                 410                 415

Tyr Ile Gly Gly Ser Thr Asn Thr Gly Ile Val Ser Lys Thr Glu Ser
            420                 425                 430

Asp Leu Val Gly Ala Val Asp Arg Asp Leu Arg Lys Met Leu Ile Asn
        435                 440                 445

Pro Arg Ala Ala Asp Pro Leu Ala Leu Gly Val Arg Val Trp Pro Gln
450                 455                 460

Ala Ile Pro Gln Phe Leu Ile Gly His Leu Asp Arg Leu Ala Ala Ala
465                 470                 475                 480

Lys Ser Ala Leu Gly Gln Gly Tyr Asp Gly Leu Phe Leu Gly Gly
                485                 490                 495

Asn Tyr Val Ala Gly Val Ala Leu Gly Arg Cys Ile Glu Gly Ala Tyr
            500                 505                 510

Glu Ser Ala Ser Gln Val Ser Asp Phe Leu Thr Lys Tyr Ala Tyr Lys
        515                 520                 525

(2) INFORMATION FOR SEQ ID NO:11:

(i) SEQUENCE CHARACTERISTICS:
        (A) LENGTH: 1847 base pairs
        (B) TYPE: nucleic acid
```

(C) STRANDEDNESS: single
(D) TOPOLOGY: linear (ii) MOLECULE TYPE: cDNA (iii) HYPOTHETICAL: NO (vi) ORIGINAL SOURCE:
(A) ORGANISM: soybean (vii) IMMEDIATE SOURCE:
(B) CLONE: pWDC-12 (NRRL B-21516)

(ix) FEATURE:
(A) NAME/KEY: CDS
(B) LOCATION: 55..1683
(D) OTHER INFORMATION: /product= "soybean protox-1"

(xi) SEQUENCE DESCRIPTION: SEQ ID NO:11:

```
CTTTAGCACA GTGTTGAAGA TAACGAACGA ATAGTGCCAT TACTGTAACC AACC ATG            57
                                                            Met
                                                            1

GTT TCC GTC TTC AAC GAG ATC CTA TTC CCG CCG AAC CAA ACC CTT CTT           105
Val Ser Val Phe Asn Glu Ile Leu Phe Pro Pro Asn Gln Thr Leu Leu
          5                  10                  15

CGC CCC TCC CTC CAT TCC CCA ACC TCT TTC TTC ACC TCT CCC ACT CGA           153
Arg Pro Ser Leu His Ser Pro Thr Ser Phe Phe Thr Ser Pro Thr Arg
     20                  25                  30

AAA TTC CCT CGC TCT CGC CCT AAC CCT ATT CTA CGC TGC TCC ATT GCG           201
Lys Phe Pro Arg Ser Arg Pro Asn Pro Ile Leu Arg Cys Ser Ile Ala
 35                  40                  45

GAG GAA TCC ACC GCG TCT CCG CCC AAA ACC AGA GAC TCC GCC CCC GTG           249
Glu Glu Ser Thr Ala Ser Pro Pro Lys Thr Arg Asp Ser Ala Pro Val
 50                  55                  60                  65

GAC TGC GTC GTC GTC GGC GGA GGC GTC AGC GGC CTC TGC ATC GCC CAG           297
Asp Cys Val Val Val Gly Gly Gly Val Ser Gly Leu Cys Ile Ala Gln
                 70                  75                  80

GCC CTC GCC ACC AAA CAC GCC AAT GCC AAC GTC GTC GTC ACG GAG GCC           345
Ala Leu Ala Thr Lys His Ala Asn Ala Asn Val Val Val Thr Glu Ala
             85                  90                  95

CGA GAC CGC GTC GGC GGC AAC ATC ACC ACG ATG GAG AGG GAC GGA TAC           393
Arg Asp Arg Val Gly Gly Asn Ile Thr Thr Met Glu Arg Asp Gly Tyr
             100                 105                 110

CTC TGG GAA GAA GGC CCC AAC AGC TTC CAG CCT TCT GAT CCA ATG CTC           441
Leu Trp Glu Glu Gly Pro Asn Ser Phe Gln Pro Ser Asp Pro Met Leu
115                 120                 125

ACC ATG GTG GTG GAC AGT GGT TTA AAG GAT GAG CTT GTT TTG GGG GAT           489
Thr Met Val Val Asp Ser Gly Leu Lys Asp Glu Leu Val Leu Gly Asp
130                 135                 140                 145

CCT GAT GCA CCT CGG TTT GTG TTG TGG AAC AGG AAG TTG AGG CCG GTG           537
Pro Asp Ala Pro Arg Phe Val Leu Trp Asn Arg Lys Leu Arg Pro Val
                150                 155                 160

CCC GGG AAG CTG ACT GAT TTG CCT TTC TTT GAC TTG ATG AGC ATT GGT           585
Pro Gly Lys Leu Thr Asp Leu Pro Phe Phe Asp Leu Met Ser Ile Gly
            165                 170                 175

GGC AAA ATC AGG GCT GGC TTT GGT GCG CTT GGA ATT CGG CCT CCT CCT           633
Gly Lys Ile Arg Ala Gly Phe Gly Ala Leu Gly Ile Arg Pro Pro Pro
            180                 185                 190

CCA GGT CAT GAG GAA TCG GTT GAA GAG TTT GTT CGT CGG AAC CTT GGT           681
Pro Gly His Glu Glu Ser Val Glu Glu Phe Val Arg Arg Asn Leu Gly
        195                 200                 205

GAT GAG GTT TTT GAA CGG TTG ATA GAG CCT TTT TGT TCA GGG GTC TAT           729
Asp Glu Val Phe Glu Arg Leu Ile Glu Pro Phe Cys Ser Gly Val Tyr
210                 215                 220                 225
```

-continued

| | | |
|---|---|---|
| GCA GGC GAT CCT TCA AAA TTA AGT ATG AAA GCA GCA TTC GGG AAA GTT<br>Ala Gly Asp Pro Ser Lys Leu Ser Met Lys Ala Ala Phe Gly Lys Val<br>230                        235                         240 | 777 |
| TGG AAG CTG GAA AAA AAT GGT GGT AGC ATT ATT GGT GGA ACT TTC AAA<br>Trp Lys Leu Glu Lys Asn Gly Gly Ser Ile Ile Gly Gly Thr Phe Lys<br>     245                       250                         255 | 825 |
| GCA ATA CAA GAG AGA AAT GGA GCT TCA AAA CCA CCT CGA GAT CCG CGT<br>Ala Ile Gln Glu Arg Asn Gly Ala Ser Lys Pro Pro Arg Asp Pro Arg<br>         260                      265                     270 | 873 |
| CTG CCA AAA CCA AAA GGT CAG ACT GTT GGA TCT TTC CGG AAG GGA CTT<br>Leu Pro Lys Pro Lys Gly Gln Thr Val Gly Ser Phe Arg Lys Gly Leu<br>275                        280                       285 | 921 |
| ACC ATG TTG CCT GAT GCA ATT TCT GCC AGA CTA GGC AAC AAA GTA AAG<br>Thr Met Leu Pro Asp Ala Ile Ser Ala Arg Leu Gly Asn Lys Val Lys<br>290                        295                     300              305 | 969 |
| TTA TCT TGG AAG CTT TCA AGT ATT AGT AAA CTG GAT AGT GGA GAG TAC<br>Leu Ser Trp Lys Leu Ser Ser Ile Ser Lys Leu Asp Ser Gly Glu Tyr<br>             310                     315                     320 | 1017 |
| AGT TTG ACA TAT GAA ACA CCA GAA GGA GTG GTT TCT TTG CAG TGC AAA<br>Ser Leu Thr Tyr Glu Thr Pro Glu Gly Val Val Ser Leu Gln Cys Lys<br>         325                      330                     335 | 1065 |
| ACT GTT GTC CTG ACC ATT CCT TCC TAT GTT GCT AGT ACA TTG CTG CGT<br>Thr Val Val Leu Thr Ile Pro Ser Tyr Val Ala Ser Thr Leu Leu Arg<br>340                        345                     350 | 1113 |
| CCT CTG TCT GCT GCT GCT GCA GAT GCA CTT TCA AAG TTT TAT TAC CCT<br>Pro Leu Ser Ala Ala Ala Ala Asp Ala Leu Ser Lys Phe Tyr Tyr Pro<br>     355                       360                     365 | 1161 |
| CCA GTT GCT GCA GTT TCC ATA TCC TAT CCA AAA GAA GCT ATT AGA TCA<br>Pro Val Ala Ala Val Ser Ile Ser Tyr Pro Lys Glu Ala Ile Arg Ser<br>370                        375                     380              385 | 1209 |
| GAA TGC TTG ATA GAT GGT GAG TTG AAG GGG TTT GGT CAA TTG CAT CCA<br>Glu Cys Leu Ile Asp Gly Glu Leu Lys Gly Phe Gly Gln Leu His Pro<br>             390                     395                     400 | 1257 |
| CGT AGC CAA GGA GTG GAA ACA TTA GGA ACT ATA TAC AGC TCA TCA CTA<br>Arg Ser Gln Gly Val Glu Thr Leu Gly Thr Ile Tyr Ser Ser Ser Leu<br>         405                      410                     415 | 1305 |
| TTC CCC AAC CGA GCA CCA CCT GGA AGG GTT CTA CTC TTG AAT TAC ATT<br>Phe Pro Asn Arg Ala Pro Pro Gly Arg Val Leu Leu Leu Asn Tyr Ile<br>             420                     425                     430 | 1353 |
| GGA GGA GCA ACT AAT ACT GGA ATT TTA TCG AAG ACG GAC AGT GAA CTT<br>Gly Gly Ala Thr Asn Thr Gly Ile Leu Ser Lys Thr Asp Ser Glu Leu<br>435                        440                     445 | 1401 |
| GTG GAA ACA GTT GAT CGA GAT TTG AGG AAA ATC CTT ATA AAC CCA AAT<br>Val Glu Thr Val Asp Arg Asp Leu Arg Lys Ile Leu Ile Asn Pro Asn<br>450                        455                     460              465 | 1449 |
| GCC CAG GAT CCA TTT GTA GTG GGG GTG AGA CTG TGG CCT CAA GCT ATT<br>Ala Gln Asp Pro Phe Val Val Gly Val Arg Leu Trp Pro Gln Ala Ile<br>             470                     475                     480 | 1497 |
| CCA CAG TTC TTA GTT GGC CAT CTT GAT CTT CTA GAT GTT GCT AAA GCT<br>Pro Gln Phe Leu Val Gly His Leu Asp Leu Leu Asp Val Ala Lys Ala<br>         485                      490                     495 | 1545 |
| TCT ATC AGA AAT ACT GGG TTT GAA GGG CTC TTC CTT GGG GGT AAT TAT<br>Ser Ile Arg Asn Thr Gly Phe Glu Gly Leu Phe Leu Gly Gly Asn Tyr<br>             500                     505                     510 | 1593 |
| GTG TCT GGT GTT GCC TTG GGA CGA TGC GTT GAG GGA GCC TAT GAG GTA<br>Val Ser Gly Val Ala Leu Gly Arg Cys Val Glu Gly Ala Tyr Glu Val<br>515                        520                     525 | 1641 |
| GCA GCT GAA GTA AAC GAT TTT CTC ACA AAT AGA GTG TAC AAA<br>Ala Ala Glu Val Asn Asp Phe Leu Thr Asn Arg Val Tyr Lys<br>530                        535                     540 | 1683 |

```
TAGTAGCAGT TTTTGTTTTT GTGGTGGAAT GGGTGATGGG ACTCTCGTGT TCCATTGAAT    1743

TATAATAATG TGAAAGTTTC TCAAATTCGT TCGATAGGTT TTTGGCGGCT TCTATTGCTG    1803

ATAATGTAAA ATCCTCTTTA AGTTTGAAAA AAAAAAAAA AAAA                      1847
```

(2) INFORMATION FOR SEQ ID NO:12:

(i) SEQUENCE CHARACTERISTICS:
        (A) LENGTH: 543 amino acids
        (B) TYPE: amino acid
        (D) TOPOLOGY: linear (ii) MOLECULE TYPE: protein (xi) SEQUENCE DESCRIPTION: SEQ ID NO:12:

```
Met Val Ser Val Phe Asn Glu Ile Leu Phe Pro Pro Asn Gln Thr Leu
 1               5                  10                  15

Leu Arg Pro Ser Leu His Ser Pro Thr Ser Phe Phe Thr Ser Pro Thr
                20                  25                  30

Arg Lys Phe Pro Arg Ser Arg Pro Asn Pro Ile Leu Arg Cys Ser Ile
            35                  40                  45

Ala Glu Glu Ser Thr Ala Ser Pro Pro Lys Thr Arg Asp Ser Ala Pro
 50                  55                  60

Val Asp Cys Val Val Gly Gly Val Ser Gly Leu Cys Ile Ala
 65              70                  75                  80

Gln Ala Leu Ala Thr Lys His Ala Asn Ala Asn Val Val Thr Glu
                85                  90                  95

Ala Arg Asp Arg Val Gly Gly Asn Ile Thr Thr Met Glu Arg Asp Gly
                100                 105                 110

Tyr Leu Trp Glu Glu Gly Pro Asn Ser Phe Gln Pro Ser Asp Pro Met
                115                 120                 125

Leu Thr Met Val Val Asp Ser Gly Leu Lys Asp Glu Leu Val Leu Gly
            130                 135                 140

Asp Pro Asp Ala Pro Arg Phe Val Leu Trp Asn Arg Lys Leu Arg Pro
145                 150                 155                 160

Val Pro Gly Lys Leu Thr Asp Leu Pro Phe Phe Asp Leu Met Ser Ile
                165                 170                 175

Gly Gly Lys Ile Arg Ala Gly Phe Gly Ala Leu Gly Ile Arg Pro Pro
                180                 185                 190

Pro Pro Gly His Glu Glu Ser Val Glu Glu Phe Val Arg Arg Asn Leu
                195                 200                 205

Gly Asp Glu Val Phe Glu Arg Leu Ile Glu Pro Phe Cys Ser Gly Val
            210                 215                 220

Tyr Ala Gly Asp Pro Ser Lys Leu Ser Met Lys Ala Ala Phe Gly Lys
225                 230                 235                 240

Val Trp Lys Leu Glu Lys Asn Gly Gly Ser Ile Ile Gly Gly Thr Phe
                245                 250                 255

Lys Ala Ile Gln Glu Arg Asn Gly Ala Ser Lys Pro Pro Arg Asp Pro
            260                 265                 270

Arg Leu Pro Lys Pro Lys Gly Gln Thr Val Gly Ser Phe Arg Lys Gly
            275                 280                 285

Leu Thr Met Leu Pro Asp Ala Ile Ser Ala Arg Leu Gly Asn Lys Val
        290                 295                 300

Lys Leu Ser Trp Lys Leu Ser Ser Ile Ser Lys Leu Asp Ser Gly Glu
305                 310                 315                 320

Tyr Ser Leu Thr Tyr Glu Thr Pro Glu Gly Val Val Ser Leu Gln Cys
                325                 330                 335
```

```
Lys Thr Val Val Leu Thr Ile Pro Ser Tyr Val Ala Ser Thr Leu Leu
                340                 345                 350

Arg Pro Leu Ser Ala Ala Ala Asp Ala Leu Ser Lys Phe Tyr Tyr
            355                 360                 365

Pro Pro Val Ala Ala Val Ser Ile Ser Tyr Pro Lys Glu Ala Ile Arg
        370                 375                 380

Ser Glu Cys Leu Ile Asp Gly Glu Leu Lys Gly Phe Gly Gln Leu His
385                 390                 395                 400

Pro Arg Ser Gln Gly Val Glu Thr Leu Gly Thr Ile Tyr Ser Ser Ser
                405                 410                 415

Leu Phe Pro Asn Arg Ala Pro Pro Gly Arg Val Leu Leu Asn Tyr
            420                 425                 430

Ile Gly Gly Ala Thr Asn Thr Gly Ile Leu Ser Lys Thr Asp Ser Glu
        435                 440                 445

Leu Val Glu Thr Val Asp Arg Asp Leu Arg Lys Ile Leu Ile Asn Pro
450                 455                 460

Asn Ala Gln Asp Pro Phe Val Val Gly Val Arg Leu Trp Pro Gln Ala
465                 470                 475                 480

Ile Pro Gln Phe Leu Val Gly His Leu Asp Leu Leu Asp Val Ala Lys
                485                 490                 495

Ala Ser Ile Arg Asn Thr Gly Phe Glu Gly Leu Phe Leu Gly Gly Asn
                500                 505                 510

Tyr Val Ser Gly Val Ala Leu Gly Arg Cys Val Glu Gly Ala Tyr Glu
            515                 520                 525

Val Ala Ala Glu Val Asn Asp Phe Leu Thr Asn Arg Val Tyr Lys
            530                 535                 540
```

(2) INFORMATION FOR SEQ ID NO:13:

(i) SEQUENCE CHARACTERISTICS:
        (A) LENGTH: 583 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: promoter
        (B) LOCATION: 1..583
        (D) OTHER INFORMATION: /function= "arabidopsis protox-1
            promoter"

(xi) SEQUENCE DESCRIPTION: SEQ ID NO:13:

```
GAATTCCGAT CGAATTATAT AATTATCATA AATTTGAATA AGCATGTTGC CTTTTATTAA      60

AGAGGTTTAA TAAAGTTTGG TAATAATGGA CTTTGACTTC AAACTCGATT CTCATGTAAT     120

TAATTAATAT TTCATCAAA ATTTGGTCAC TAATATTACC AAATTAATAT ACTAAAATGT      180

TAATTCGCAA ATAAAACACT AATTCCAAAT AAAGGGTCAT TATGATAAAC ACGTATTGAA     240

CTTGATAAAG CAAAGCAAAA ATAATGGGTT TCAAGGTTTG GGTTATATAT GACAAAAAAA     300

AAAAAAGGTT TGGTTATATA TCTATTGGGC CTATAACCAT GTTATACAAA TTTGGGCCTA     360

ACTAAAATAA TAAAATAAAC GTAATGGTCC TTTTTATATT TGGGTCAAAC CCAACTCTAA     420

ACCCAAACCA AAGAAAAAGT ATACGGTACG GTACACAGAC TTATGGTGTG TGTGATTGCA     480

GGTGAATATT TCTCGTCGTC TTCTCCTTTC TTCTGAAGAA GATTACCCAA TCTGAAAAAA     540

ACCAAGAAGC TGACAAAATT CCGAATTCTC TGCGATTTCC ATG                       583
```

(2) INFORMATION FOR SEQ ID NO:14:

(i) SEQUENCE CHARACTERISTICS:
        (A) LENGTH: 3848 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: promoter
        (B) LOCATION: 1..3848
        (D) OTHER INFORMATION: /function= "maize protox-1 promoter"

(xi) SEQUENCE DESCRIPTION: SEQ ID NO:14:

```
TCGATCTTTC TAGGCTGATC CCCAAATCTT CCTCCGAAGC CCCTGGCGCC TCTGCCCCTT      60

GGAGCTGGTG GCCTGAAAGA GCTTTGCTGT TGCCCCGAAG ATTGTGAGGT ATATTGTGAC     120

CTCTGAGACT GACTTCCTTT GTCGTCACTT TGAGTGGAGT TATGGATTGA CCTGACGTGC     180

CTCAGATGGA TTCTTCCTCC GAAGCCCCTG GTCATTTCGG AGAATCTGTA ATCTTATTCC     240

CTTCTTTGGC GAAAATCTGT CAGCTTGGAT GTACTCATCC ATCTTCTGAA GCAGCTTCTC     300

CAGAGTTTGT GGAGGCTTCC TGGCGAAATA TTGGGCTGTA GGTCCTGGAC GAAGACCCTT     360

GATCATGGCC TCAATGACAA TCTCATTGGG CACCGTAGGC GCTTGTGCCC TCAATCGCAA     420

GAACCTTCGT ACATATGCCT GAAGGTATTC TTCGTGATCT TGTGTGCATT GGAACAGAGC     480

CTGAGCTGTG ACCGACTTCG TTTGAAAGCC TTGGAAGCTA GTAACCAACA TGTGCTTAAG     540

CTTCTGCCAC GACGTGATAG TCCCTGGCCG AAGAGAAGAA TACCATGTTT GGGCTACATT     600

CCGGACTGCC ATGACGAAGG ACTTCGCCAT GACTACAGTG TTGACCCCAT ACGAAGATAT     660

AGTTGCTTCG TAGCTCATCA GAAACTGCTT TGGATCTGAG TGCCCATCAT ACATGGGGAG     720

CTGAGGTGGC TTGTATGATG GGGGCCATGG GGTAGCCTGC AGTTCTGCTG CCAAGGGAGA     780

AGCATCATCA AAAGTAAAGG CATCATGATT AAAATCATCA TACCATCCAT CCTCGTTGAA     840

TAAGCCTTCT TGACGAAGCT CCCTGTGTTG GGGCCTTCGA TCTTGTTCAT CTTGAACAAG     900

ATGACGCACT TCTTCAGTGG CTTCGTCGAT CTTTCTTTGG AGATCAGCCA GTCGCACCAT     960

CTTCTCCTTC TTTCTTTGTA CTTGTTGATG GATGATCTCC ATGTCCCTGA TCTCTTGGTC    1020

CAACTCCTCC TCTTGGAGTG TCAGACTGGT GGCTTTCCTC TTCTGGCTTC GAGCCTCTCG    1080

AAGAGAAAGA GTTTCTTGAT TTGGGTCCAG CGGCTGCAGT GCAGTGGTCC CTGGTGCTGA    1140

AGCTTTCTTC GGTGGCATGA CAAAGGTCAG TGCTTGCCGA AGGTGGTCGA AAAGGGTTCA    1200

CTAGAGGTGG GAGCCAATGT TGGGACTTC TCAAGTGCTA TGAGTTAAGA CAAGGCAAC     1260

ACAAAATGTT AAATATTAAT AGCTTTCATC TTTCGAAGCA TTATTTCCCT TTGGGTATAA    1320

TGATCTTCAG ACGAAAGAGT CCTTCATCAT TGCGATATAT GTTAATAGAA GGAGGAGCAT    1380

ATGAAATGTA AGAGACAACA TGAACAATCG TGTAGCATTG TTAATTCATC ATCATTTTAT    1440

TATTATGGAA AAATAGAAAC AATATTGAAT TACAAATGTA CCTTTGGCTT GACAGAAGAT    1500

AAAAGTACAA GCTTGACGCA CGAGCAAGTA CAAGTCAGTG TGAACAGTAC GGGGGTACTG    1560

TTCATCTATT TATAGGCACA GGACACAGCC TGTGAGAAAT TACAGTCATG CCCTTTACAT    1620

TTACTATTGA CTTATAGAAA AATCTATGAG GACTGGATAG CCTTTTCCCC TTTAAGTCGG    1680

TGCCTTTTTC CGCGATTAAG CCGAATCTCC CTTGCGCATA GCTTCGGAGC ATCGGCAACC    1740

TTCGTCACGA TCATGCCCTT CTCATTGTGT ATGCTTTTAA TCCTGAATTC GAAGGTACCT    1800
```

```
GTCCATAAAC CATACTTGGA AGACATTGTT AAATTATGTT TTTGAGGACC TTCGGAGGAC    1860

GAAGGCCCCC AACAGTCGTG TTTTTGAGGA CCTTCGGAAG ATGAAGGCCC CCAACAAGAC    1920

CTATCCATAA AACCAACCTA TCCACAAAAC CGACCCCATT CACCCTTCAT TTGCCTCACC    1980

AACAACCCTA ATTAGGTTGT TGGTTTAAAT TTTTTAGGGT CAATTTGGTC ATCACCATCC    2040

ACTGTCACTC CACAAACTCA ATATCAATAA ACAGACTCAA TCACCCAAAC TGACCATACC    2100

CATAAAACCG CCCCACCCTT CTAGCGCCTC GCCAGAAACC AGAAACCCTG ATTCAGAGTT    2160

CAAACTTAAA ACGACCATAA CTTTCACCTT GGAACTCGAA TCAGGTCCAT TTTTTTCCAA    2220

ATCACACAAA ATTAAATTTC GCATCCGATA ATCAAGCCAT CTCTTCACTA TGGTTTTAAG    2280

TGTTGCTCAC ACTAGTGTAT TTATGGACTA ATCACCTGTG TATCTCATAC AATAACATAT    2340

CAGTACATCT AAGTTGTTAC TCAATTACCA AAACCGAATT ATAGCCTTCG AAAAAGGTTA    2400

TCGACTAGTC ACTCAATTAC CAAAACTAAA CTTTAGACTT TCATGTATGA CATCCAACAT    2460

GACACTGTAC TGGACTAAAC CACCTTTCAA GCTACACAAG GAGCAAAAAT AACTAATTTT    2520

CGTAGTTGTA GGAGCTAAAG TATATGTCCA CAACAATAGT TAAGGGAAGC CCCCAAGGAC    2580

TTAAAAGTCC TTTTACCTCT TGAAACTTTT GTCGTGGTCT ACTTTTTCAC TTTAAACTTC    2640

AAAATTTGAC ATTTTATCAC CCCTTAACTC TTAAAACCAT TTAAATTACA TTCTTACTAG    2700

ATTATAGATG ATTTTGTTGT GAAAAGTTTT TAAGACATGT TTACACATTG ATTAAAATCA    2760

TTTGTTCAAT TTCCTAGAGT TAAATCTAAT CTTATTAAAA CTATTAGAGA TACTTTCACG    2820

AGCTCTAAAT ATTTTTATTT TTTCATTATG GAATTTTGTT AGAATTCTTA TAGACCTTTT    2880

TTTGTGGTTT AAAAGCCTTG CCATGTTTTT AACAAGTTTT TTTTCTATTT TTTGAAATTT    2940

TCTTGGAAAC CACTTCTAAC CCGGTAGAAG ATTTATTTTG CTACACTTAT ATCTACAACA    3000

AAATCAACTT ATGAAATTGT CTTGGAAACT ACCTCTAACC CGGTAGAATG AATTTGAATG    3060

AAAATTAAAC CAACTTACGG AATCGCCCAA CATATGTCGA TTAAAGTGGA TATGGATACA    3120

TATGAAGAAG CCCTAGAGAT AATCTAAATG GTTTCAGAAT TGAGGGTTAT TTTTTGAAGT    3180

TTGATGGGAA GATAAGACCA TAACGGTAGT TCACAGAGAT AAAAGGGTTA TTTTTTTCAG    3240

AAATATTTGT GCTGCAATTG ATCCTGTGCC TCAAATTCAG CCTGCAACCA AGGCCAGGTT    3300

CTAGAGCGAA CAAGGCCCAC GTCACCCGTG GCCCGTCAGG CGAAGCAGGT CTTGTGCAGA    3360

CTTTGAGAGG GATTGGATAT CAACGGAACC AATCACGCAC GGCAATGCGA TTCCCAGCCC    3420

ACCTGTAACG TTCCAGTGGG CCATCCTTAA CTCCAAGCCC AACGGCCCTA CCCCATCTCG    3480

TCGTGTCATC CACTCCGCCG CACAGGCGCT CAGCTCCGCA ACGCCGCCGG AAATGGTCGC    3540

CGCCACAGCC ACCGCCATGG CCACCGCTGC ATCGCCGCTA CTCAACGGGA CCCGAATACC    3600

TGCGCGGCTC CGCCATCGAG GACTCAGCGT GCGCTGCGCT GCTGTGGCGG GCGGCGCGGC    3660

CGAGGCACCG GCATCCACCG GCGCGCGGCT GTCCGCGGAC TGCGTTGTGG TGGGCGGAGG    3720

CATCAGTGGC CTCTGCACCG CGCAGGCGCT GGCCACGCGG CACGGCGTCG GGACGTGCT    3780

TGTCACGGAG GCCCGCGCCC GCCCCGGCGG CAACATTACC ACCGTCGAGC GCCCCGAGGA    3840

AGGGTACC                                                           3848
```

(2) INFORMATION FOR SEQ ID NO:15:

(i) SEQUENCE CHARACTERISTICS:
        (A) LENGTH: 1826 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Gossypium hirsutum (cotton)

(vii) IMMEDIATE SOURCE:
    (B) CLONE: pWDC-15 (NRRL B-21594)

(ix) FEATURE:
    (A) NAME/KEY: misc_feature
    (B) LOCATION: 31..1647
    (D) OTHER INFORMATION: /product= "Cotton protox-1 coding region"

(xi) SEQUENCE DESCRIPTION: SEQ ID NO:15:

```
CCTCTCGCTC GCCTGGCCCC ACCACCAATC ATGACGGCTC TAATCGACCT TTCTCTTCTC     60
CGTTCCTCGC CCTCCGTTTC CCCTTTCTCC ATACCCCACC ACCAGCATCC GCCCCGCTTT    120
CGTAAACCTT TCAAGCTCCG ATGCTCCCTC GCCGAGGGTC CCACGATTTC CTCATCTAAA    180
ATCGACGGGG GAGAATCATC CATCGCGGAT TGCGTCATCG TTGGAGGTGG TATCAGTGGA    240
CTTTGCATTG CTCAAGCTCT CGCCACCAAG CACCGTGACG TCGCTTCCAA TGTGATTGTG    300
ACGGAGGCCA GAGACCGTGT TGGTGGCAAC ATCACTACCG TTGAGAGAGA TGGATATCTG    360
TGGGAAGAAG GCCCCAACAG TTTTCAGCCC TCCGATCCTA TTCTAACCAT GGCCGTGGAT    420
AGTGGATTGA AGGACGATTT GGTTTTAGGT GACCCTAATG CACCGCGATT TGTACTATGG    480
GAGGGAAAAC TAAGGCCTGT GCCCTCCAAG CCAACCGACT TGCCGTTTTT TGATTTGATG    540
AGCATTGCTG GAAAACTTAG GGCTGGGTTC GGGGCTATTG GCATTCGGCC TCCCCCTCCG    600
GGTTATGAAG AATCGGTGGA GGAGTTTGTG CGCCGTAATC TTGGTGCTGA GGTTTTTGAA    660
CGCTTTATTG AACCATTTTG TTCAGGTGTT TATGCAGGGG ATCCTTCAAA ATTAAGCATG    720
AAAGCAGCAT TTGGAAGAGT ATGGAAGCTA AAGAGATTG GTGGCAGCAT CATTGGTGGC     780
ACTTTCAAGA CAATCCAGGA GAGAAATAAG ACACCTAAGC CACCCAGAGA CCCGCGTCTG    840
CCAAAACCGA AGGGCCAAAC AGTTGGATCT TTTAGGAAGG GACTTACCAT GCTGCCTGAG    900
GCAATTGCTA ACAGTTTGGG TAGCAATGTA AAATTATCTT GGAAGCTTTC CAGTATTACC    960
AAATTGGGCA ATGGAGGGTA TAACTTGACA TTTGAAACAC CTGAAGGAAT GGTATCTCTT   1020
CAGAGTAGAA GTGTTGTAAT GACCATTCCA TCCCATGTTG CCAGTAACTT GTTGCATCCT   1080
CTCTCGGCTG CTGCTGCAGA TGCATTATCC CAATTTTATT ATCCTCCAGT TGCATCAGTC   1140
ACAGTCTCCT ATCCAAAAGA AGCCATTCGA AAAGAATGTT TGATTGATGG TGAACTTAAG   1200
GGGTTTGGCC AGTTGCACCC ACGCAGCCAA GGAATTGAAA CTTTAGGGAC GATATACAGT   1260
TCATCACTTT TCCCCAATCG AGCTCCATCT GGCAGGGTGT TGCTCTTGAA CTACATAGGA   1320
GGAGCTACCA ACACTGGAAT TTTGTCCAAG ACTGAAGGGG AACTTGTAGA AGCAGTTGAT   1380
CGTGATTTGA GAAAAATGCT TATAAATCCT AATGCAAAGG ATCCTCTTGT TTTGGGTGTA   1440
AGAGTATGGC CAAAAGCCAT TCCACAGTTC TTGGTTGGTC ATTTGGATCT CCTTGATAGT   1500
GCAAAAATGG CTCTCAGGGA TTCTGGGTTT CATGGACTGT TTCTTGGGGG CAACTATGTA   1560
TCTGGTGTGG CATTAGGACG GTGTGTGGAA GGTGCTTACG AGGTTGCAGC TGAAGTGAAG   1620
GAATTCCTGT CACAATATGC ATACAAATAA TATTGAAATT CTTGTCAGGC TGCAAATGTA   1680
GAAGTCAGTT ATTGGATAGT ATCTCTTTAG CTAAAAAATT GGGTAGGGTT TTTTTTGTTA   1740
GTTCCTTGAC CACTTTTTGG GGTTTTCATT AGAACTTCAT ATTTGTATAT CATGTTGCAA   1800
```

TATCAAAAAA AAAAAAAAAA AAAAAA                                                  1826

(2) INFORMATION FOR SEQ ID NO:16:

(i) SEQUENCE CHARACTERISTICS:
        (A) LENGTH: 539 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:16:

```
Met Thr Ala Leu Ile Asp Leu Ser Leu Leu Arg Ser Pro Ser Val
 1               5                  10                  15

Ser Pro Phe Ser Ile Pro His His Gln His Pro Arg Phe Arg Lys
                20                  25                  30

Pro Phe Lys Leu Arg Cys Ser Leu Ala Glu Gly Pro Thr Ile Ser Ser
            35                  40                  45

Ser Lys Ile Asp Gly Gly Glu Ser Ser Ile Ala Asp Cys Val Ile Val
    50                  55                  60

Gly Gly Gly Ile Ser Gly Leu Cys Ile Ala Gln Ala Leu Ala Thr Lys
65                  70                  75                  80

His Arg Asp Val Ala Ser Asn Val Ile Val Thr Glu Ala Arg Asp Arg
                85                  90                  95

Val Gly Gly Asn Ile Thr Thr Val Glu Arg Asp Gly Tyr Leu Trp Glu
                100                 105                 110

Glu Gly Pro Asn Ser Phe Gln Pro Ser Asp Pro Ile Leu Thr Met Ala
                115                 120                 125

Val Asp Ser Gly Leu Lys Asp Asp Leu Val Leu Gly Asp Pro Asn Ala
    130                 135                 140

Pro Arg Phe Val Leu Trp Glu Gly Lys Leu Arg Pro Val Pro Ser Lys
145                 150                 155                 160

Pro Thr Asp Leu Pro Phe Phe Asp Leu Met Ser Ile Ala Gly Lys Leu
                165                 170                 175

Arg Ala Gly Phe Gly Ala Ile Gly Ile Arg Pro Pro Pro Gly Tyr
                180                 185                 190

Glu Glu Ser Val Glu Glu Phe Val Arg Arg Asn Leu Gly Ala Glu Val
                195                 200                 205

Phe Glu Arg Phe Ile Glu Pro Phe Cys Ser Gly Val Tyr Ala Gly Asp
    210                 215                 220

Pro Ser Lys Leu Ser Met Lys Ala Ala Phe Gly Arg Val Trp Lys Leu
225                 230                 235                 240

Glu Glu Ile Gly Gly Ser Ile Ile Gly Gly Thr Phe Lys Thr Ile Gln
                245                 250                 255

Glu Arg Asn Lys Thr Pro Lys Pro Pro Arg Asp Pro Arg Leu Pro Lys
                260                 265                 270

Pro Lys Gly Gln Thr Val Gly Ser Phe Arg Lys Gly Leu Thr Met Leu
    275                 280                 285

Pro Glu Ala Ile Ala Asn Ser Leu Gly Ser Asn Val Lys Leu Ser Trp
    290                 295                 300

Lys Leu Ser Ser Ile Thr Lys Leu Gly Asn Gly Gly Tyr Asn Leu Thr
305                 310                 315                 320

Phe Glu Thr Pro Glu Gly Met Val Ser Leu Gln Ser Arg Ser Val Val
                325                 330                 335

Met Thr Ile Pro Ser His Val Ala Ser Asn Leu Leu His Pro Leu Ser
                340                 345                 350
```

```
Ala Ala Ala Ala Asp Ala Leu Ser Gln Phe Tyr Tyr Pro Pro Val Ala
            355                 360                 365

Ser Val Thr Val Ser Tyr Pro Lys Glu Ala Ile Arg Lys Glu Cys Leu
    370                 375                 380

Ile Asp Gly Glu Leu Lys Gly Phe Gly Gln Leu His Pro Arg Ser Gln
385                 390                 395                 400

Gly Ile Glu Thr Leu Gly Thr Ile Tyr Ser Ser Leu Phe Pro Asn
                405                 410                 415

Arg Ala Pro Ser Gly Arg Val Leu Leu Leu Asn Tyr Ile Gly Gly Ala
                420                 425                 430

Thr Asn Thr Gly Ile Leu Ser Lys Thr Glu Gly Glu Leu Val Glu Ala
            435                 440                 445

Val Asp Arg Asp Leu Arg Lys Met Leu Ile Asn Pro Asn Ala Lys Asp
        450                 455                 460

Pro Leu Val Leu Gly Val Arg Val Trp Pro Lys Ala Ile Pro Gln Phe
465                 470                 475                 480

Leu Val Gly His Leu Asp Leu Leu Asp Ser Ala Lys Met Ala Leu Arg
                485                 490                 495

Asp Ser Gly Phe His Gly Leu Phe Leu Gly Gly Asn Tyr Val Ser Gly
                500                 505                 510

Val Ala Leu Gly Arg Cys Val Glu Gly Ala Tyr Glu Val Ala Ala Glu
            515                 520                 525

Val Lys Glu Phe Leu Ser Gln Tyr Ala Tyr Lys
    530                 535

(2) INFORMATION FOR SEQ ID NO:17:

(i) SEQUENCE CHARACTERISTICS:
        (A) LENGTH: 1910 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Beta vulgaris (Sugar Beet)

(vii) IMMEDIATE SOURCE:
          (B) CLONE: pWDC-16 (NRRL B-21595N)

(ix) FEATURE:
         (A) NAME/KEY: misc_feature
         (B) LOCATION: 1..1680
         (D) OTHER INFORMATION: /product= "Sugar Beet Protox-1 coding
             region"

(xi) SEQUENCE DESCRIPTION: SEQ ID NO:17:

ATGAAATCAA TGGCGTTATC AAACTGCATT CCACAGACAC AGTGCATGCC ATTGCGCAGC        60

AGCGGGCATT ACAGGGGTAA TTGTATCATG TTGTCAATTC CATGTAGTTT AATTGGAAGA       120

CGAGGTTATT ATTCACATAA GAAGAGGAGG ATGAGCATGA GTTGCAGCAC AAGCTCAGGC       180

TCAAAGTCAG CGGTTAAAGA AGCAGGATCA GGATCAGGTG CAGGAGGATT GCTAGACTGC       240

GTAATCGTTG GAGGTGGAAT TAGCGGGCTT TGCATCGCGC AGGCTCTTTG TACAAAACAC       300

TCCTCTTCCT CTTTATCCCC AAATTTTATA GTTACAGAGG CCAAAGACAG AGTTGGCGGC       360

AACATCGTCA CTGTGGAGGC CGATGGCTAT ATCTGGGAGG AGGGACCCAA TAGCTTCCAG       420
```

```
CCTTCCGACG CGGTGCTCAC CATGGCGGTC GACAGTGGCT TGAAAGATGA GTTGGTGCTC    480

GGAGATCCCA ATGCTCCTCG CTTTGTGCTA TGGAATGACA AATTAAGGCC CGTACCTTCC    540

AGTCTCACCG ACCTCCCTTT CTTCGACCTC ATGACCATTC CGGGCAAGAT TAGGGCTGCT    600

CTTGGTGCTC TCGGATTTCG CCCTTCTCCT CCACCTCATG AGGAATCTGT TGAACACTTT    660

GTGCGTCGTA ATCTCGGAGA TGAGGTCTTT GAACGCTTGA TTGAACCCTT TTGTTCAGGT    720

GTGTATGCCG GTGATCCTGC CAAGCTGAGT ATGAAAGCTG CTTTTGGGAA GGTCTGGAAG    780

TTGGAGCAAA AGGGTGGCAG CATAATTGGT GGCACTCTCA AAGCTATACA GGAAAGAGGG    840

AGTAATCCTA AGCCGCCCCG TGACCAGCGC CTCCCTAAAC CAAAGGGTCA GACTGTTGGA    900

TCCTTTAGAA AGGGACTCGT TATGTTGCCT ACCGCCATTT CTGCTCGACT GGCAGTAGA    960

GTGAAACTAT CTTGGACCCT TTCTAGTATC GTAAAGTCAC TCAATGGAGA ATATAGTCTG   1020

ACTTATGATA CCCCAGATGG CTTGGTTTCT GTAAGAACCA AAAGTGTTGT GATGACTGTT   1080

CCATCATATG TTGCAAGTAG GCTTCTTCGT CCACTTTCAG ACTCTGCTGC AGATTCTCTT   1140

TCAAAATTTT ACTATCCACC AGTTGCAGCA GTGTCACTTT CCTATCCTAA GAAGCGATC    1200

AGATCAGAAT GCTTGATTAA TGGTGAACTT CAAGGTTTCG GCAACTACA TCCCCGCAGT    1260

CAGGGTGTGG AAACCTTGGG AACAATTTAT AGTTCGTCTC TTTTCCCTGG TCGAGCACCA   1320

CCTGGTAGGA TCTTGATCTT GAGCTACATC GGAGGTGCTA AAAATCCTGG CATATTAAAC   1380

AAGTCGAAAG ATGAACTTGC CAAGACAGTT GACAAGGACC TGAGAAGAAT GCTTATAAAT   1440

CCTGATGCAA AACTTCCTCG TGTACTGGGT GTGAGAGTAT GGCCTCAAGC AATACCCCAG   1500

TTTTCTATTG GCACTTTGA TCTGCTCGAT GCTGCAAAAG CTGCTCTGAC AGATACAGGG    1560

GTCAAAGGAC TGTTTCTTGG TGGCAACTAT GTTTCAGGTG TTGCCTTGGG GCGGTGTATA   1620

GAGGGTGCTT ATGAGTCTGC AGCTGAGGTA GTAGATTTCC TCTCACAGTA CTCAGACAAA   1680

TAGAGCTTCA GCATCCTGTG TAATTCAACA CAGGCCTTTT TGTATCTGTT GTGCGCGCAT   1740

GTAGTCTGGT CGTGGTGCTA GGATTGATTA GTTGCTCTGC TGTGTGATCC ACAAGAATTT   1800

TGATGGAATT TTTCCAGATG TGGGCATTAT ATGTTGCTGT CTTATAAATC CTTAATTTGT   1860

ACGTTTAGTG AATTACACCG CATTTGATGA CTAAAAAAAA AAAAAAAAA               1910
```

(2) INFORMATION FOR SEQ ID NO:18:

(i) SEQUENCE CHARACTERISTICS:
        (A) LENGTH: 560 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:18:

```
Met Lys Ser Met Ala Leu Ser Asn Cys Ile Pro Gln Thr Gln Cys Met
1               5                   10                  15

Pro Leu Arg Ser Ser Gly His Tyr Arg Gly Asn Cys Ile Met Leu Ser
            20                  25                  30

Ile Pro Cys Ser Leu Ile Gly Arg Arg Gly Tyr Tyr Ser His Lys Lys
        35                  40                  45

Arg Arg Met Ser Met Ser Cys Ser Thr Ser Ser Gly Ser Lys Ser Ala
    50                  55                  60

Val Lys Glu Ala Gly Ser Gly Ser Gly Ala Gly Leu Leu Asp Cys
65                  70                  75                  80

Val Ile Val Gly Gly Gly Ile Ser Gly Leu Cys Ile Ala Gln Ala Leu
                85                  90                  95
```

-continued

```
Cys Thr Lys His Ser Ser Ser Leu Ser Pro Asn Phe Ile Val Thr
             100                 105                 110

Glu Ala Lys Asp Arg Val Gly Gly Asn Ile Val Thr Val Glu Ala Asp
         115                 120                 125

Gly Tyr Ile Trp Glu Glu Gly Pro Asn Ser Phe Gln Pro Ser Asp Ala
     130                 135                 140

Val Leu Thr Met Ala Val Asp Ser Gly Leu Lys Asp Glu Leu Val Leu
145                 150                 155                 160

Gly Asp Pro Asn Ala Pro Arg Phe Val Leu Trp Asn Asp Lys Leu Arg
                 165                 170                 175

Pro Val Pro Ser Ser Leu Thr Asp Leu Pro Phe Phe Asp Leu Met Thr
             180                 185                 190

Ile Pro Gly Lys Ile Arg Ala Ala Leu Gly Ala Leu Gly Phe Arg Pro
         195                 200                 205

Ser Pro Pro His Glu Glu Ser Val Glu His Phe Val Arg Arg Asn
     210                 215                 220

Leu Gly Asp Glu Val Phe Glu Arg Leu Ile Glu Pro Phe Cys Ser Gly
225                 230                 235                 240

Val Tyr Ala Gly Asp Pro Ala Lys Leu Ser Met Lys Ala Ala Phe Gly
                 245                 250                 255

Lys Val Trp Lys Leu Glu Gln Lys Gly Gly Ser Ile Ile Gly Gly Thr
             260                 265                 270

Leu Lys Ala Ile Gln Glu Arg Gly Ser Asn Pro Lys Pro Pro Arg Asp
         275                 280                 285

Gln Arg Leu Pro Lys Pro Lys Gly Gln Thr Val Gly Ser Phe Arg Lys
     290                 295                 300

Gly Leu Val Met Leu Pro Thr Ala Ile Ser Ala Arg Leu Gly Ser Arg
305                 310                 315                 320

Val Lys Leu Ser Trp Thr Leu Ser Ile Val Lys Ser Leu Asn Gly
                 325                 330                 335

Glu Tyr Ser Leu Thr Tyr Asp Thr Pro Asp Gly Leu Val Ser Val Arg
             340                 345                 350

Thr Lys Ser Val Val Met Thr Val Pro Ser Tyr Val Ala Ser Arg Leu
         355                 360                 365

Leu Arg Pro Leu Ser Asp Ser Ala Ala Asp Ser Leu Ser Lys Phe Tyr
     370                 375                 380

Tyr Pro Pro Val Ala Ala Val Ser Leu Ser Tyr Pro Lys Glu Ala Ile
385                 390                 395                 400

Arg Ser Glu Cys Leu Ile Asn Gly Glu Leu Gln Gly Phe Gly Gln Leu
                 405                 410                 415

His Pro Arg Ser Gln Gly Val Glu Thr Leu Gly Thr Ile Tyr Ser Ser
             420                 425                 430

Ser Leu Phe Pro Gly Arg Ala Pro Gly Arg Ile Leu Ile Leu Ser
         435                 440                 445

Tyr Ile Gly Gly Ala Lys Asn Pro Gly Ile Leu Asn Lys Ser Lys Asp
     450                 455                 460

Glu Leu Ala Lys Thr Val Asp Lys Asp Leu Arg Arg Met Leu Ile Asn
465                 470                 475                 480

Pro Asp Ala Lys Leu Pro Arg Val Leu Gly Val Arg Val Trp Pro Gln
                 485                 490                 495

Ala Ile Pro Gln Phe Ser Ile Gly His Phe Asp Leu Leu Asp Ala Ala
             500                 505                 510

Lys Ala Ala Leu Thr Asp Thr Gly Val Lys Gly Leu Phe Leu Gly Gly
```

```
                515                 520                 525
Asn Tyr Val Ser Gly Val Ala Leu Gly Arg Cys Ile Glu Gly Ala Tyr
    530                 535                 540

Glu Ser Ala Ala Glu Val Val Asp Phe Leu Ser Gln Tyr Ser Asp Lys
545                 550                 555                 560
```

(2) INFORMATION FOR SEQ ID NO:19:

(i) SEQUENCE CHARACTERISTICS:
        (A) LENGTH: 1784 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Brassica napus (rape)

(vii) IMMEDIATE SOURCE:
        (B) CLONE: pWDC-17 (NRRL B-21615)

(ix) FEATURE:
        (A) NAME/KEY: misc_feature
        (B) LOCATION: 47..1654
        (D) OTHER INFORMATION: /product= "Rape Protox-1 coding region"

(xi) SEQUENCE DESCRIPTION: SEQ ID NO:19:

```
GGGCCCCCCC CAAAATTGAG GATTCTCCTT CTCGCGGGCG ATCGCCATGG ATTTATCTCT     60
TCTCCGTCCG CAGCCATTCC TATCGCCATT CTCAAATCCA TTTCCTCGGT CGCGTCCCTA    120
CAAGCCTCTC AACCTCCGTT GCTCCGTATC CGGTGGATCC GTCGTCGGCT CTTCTACAAT    180
CGAAGGCGGA GGAGGAGGTA AAACCGTCAC GGCGGACTGC GTGATCGTCG GCGGAGGAAT    240
CAGCGGCCTG TGCATTGCGC AAGCGCTCGT GACGAAGCAC CCAGACGCTG CAAAGAATGT    300
GATGGTGACG GAGGCGAAGG ACCGTGTGGG AGGGAATATC ATCACGCGAG AGGAGCAAGG    360
GTTTCTATGG GAAGAAGGTC CCAATAGCTT TCAGCCGTCT GATCCTATGC TCACTATGGT    420
GGTAGATAGT GGTTTGAAAG ATGATCTAGT CTTGGGAGAT CCTACTGCTC CGAGGTTTGT    480
GTTGTGGAAT GGGAAGCTGA GGCCGGTTCC GTCGAAGCTA ACTGACTTGC CTTTCTTTGA    540
CTTGATGAGT ATTGGAGGGA AGATTAGAGC TGGGTTTGGT GCCATTGGTA TTCGACCTTC    600
ACCTCCGGGT CGTGAGGAAT CAGTGGAAGA GTTTGTAAGG CGTAATCTTG GTGATGAGGT    660
TTTTGAGCGC TTGATTGAAC CCTTTTGCTC AGGTGTTTAT GCGGGAGATC CTGCGAAACT    720
GAGTATGAAA GCAGCTTTTG GGAAGGTTTG GAAGCTAGAG GAGAATGGTG GGAGCATCAT    780
TGGTGGTGCT TTTAAGGCAA TTCAAGCGAA AAATAAAGCT CCCAAGACAA CCCGAGATCC    840
GCGTCTGCCA AAGCCAAAGG GCCAAACTGT TGGTTCTTTC AGGAAAGGAC TCACAATGCT    900
GCCAGAGGCA ATCTCCGCAA GGTTGGGTGA CAAGGTGAAA GTTTCTTGGA AGCTCTCAAG    960
TATCACTAAG CTGGCCAGCG GAGAATATAG CTTAACTTAC GAAACTCCGG AGGGTATAGT   1020
CACTGTACAG AGCAAAAGTG TAGTGATGAC TGTGCCATCT CATGTTGCTA GTAGTCTCTT   1080
GCGCCCTCTC TCTGATTCTG CAGCTGAAGC GCTCTCAAAA CTCTACTATC CGCCAGTTGC   1140
AGCCGTATCC ATCTCATACG CGAAAGAAGC AATCCGAAGC GAATGCTTAA TAGATGGTGA   1200
ACTAAAAGGG TTCGGCCAGT TGCATCCACG CACGCAAAAA GTGGAAACTC TTGGAACAAT   1260
ATACAGTTCA TCGCTCTTTC CCAACCGAGC ACCGCCTGGA AGAGTATTGC TATTGAACTA   1320
```

```
CATCGGTGGA GCTACCAACA CTGGGATCTT ATCAAAGTCG GAAGGTGAGT TAGTGGAAGC    1380

AGTAGATAGA GACTTGAGGA AGATGCTGAT AAAGCCAAGC TCGACCGATC CACTTGTACT    1440

TGGAGTAAAA TTATGGCCTC AAGCCATTCC TCAGTTTCTG ATAGGTCACA TTGATTTGGT    1500

AGACGCAGCG AAAGCATCGC TCTCGTCATC TGGTCATGAG GGCTTATTCT TGGGTGGAAA    1560

TTACGTTGCC GGTGTAGCAT TGGGTCGGTG TGTGGAAGGT GCTTATGAAA CTGCAACCCA    1620

AGTGAATGAT TTCATGTCAA GGTATGCTTA CAAGTAATGT AACGCAGCAA CGATTTGATA    1680

CTAAGTAGTA GATTTTGCAG TTTTGACTTT AAGAACACTC TGTTTGTGAA AAATTCAAGT    1740

CTGTGATTGA GTAAATTTAT GTATTATTAC TAAAAAAAAA AAAA                    1784
```

(2) INFORMATION FOR SEQ ID NO:20:

(i) SEQUENCE CHARACTERISTICS:
        (A) LENGTH: 536 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:20:

```
Met Asp Leu Ser Leu Leu Arg Pro Gln Pro Phe Leu Ser Pro Phe Ser
1               5                   10                  15

Asn Pro Phe Pro Arg Ser Arg Pro Tyr Lys Pro Leu Asn Leu Arg Cys
                20                  25                  30

Ser Val Ser Gly Gly Ser Val Gly Ser Ser Thr Ile Glu Gly Gly
            35                  40                  45

Gly Gly Gly Lys Thr Val Thr Ala Asp Cys Val Ile Val Gly Gly
        50                  55                      60

Ile Ser Gly Leu Cys Ile Ala Gln Ala Leu Val Thr Lys His Pro Asp
65                  70                  75                  80

Ala Ala Lys Asn Val Met Val Thr Glu Ala Lys Asp Arg Val Gly Gly
                85                  90                  95

Asn Ile Ile Thr Arg Glu Glu Gln Gly Phe Leu Trp Glu Gly Pro
                100                 105                 110

Asn Ser Phe Gln Pro Ser Asp Pro Met Leu Thr Met Val Val Asp Ser
            115                 120                 125

Gly Leu Lys Asp Asp Leu Val Leu Gly Asp Pro Thr Ala Pro Arg Phe
        130                 135                 140

Val Leu Trp Asn Gly Lys Leu Arg Pro Val Ser Lys Leu Thr Asp
145                 150                 155                 160

Leu Pro Phe Phe Asp Leu Met Ser Ile Gly Gly Lys Ile Arg Ala Gly
                165                 170                 175

Phe Gly Ala Ile Gly Ile Arg Pro Ser Pro Pro Gly Arg Glu Glu Ser
            180                 185                 190

Val Glu Glu Phe Val Arg Arg Asn Leu Gly Asp Glu Val Phe Glu Arg
        195                 200                 205

Leu Ile Glu Pro Phe Cys Ser Gly Val Tyr Ala Gly Asp Pro Ala Lys
210                 215                 220

Leu Ser Met Lys Ala Ala Phe Gly Lys Val Trp Lys Leu Glu Glu Asn
225                 230                 235                 240

Gly Gly Ser Ile Ile Gly Gly Ala Phe Lys Ala Ile Gln Ala Lys Asn
                245                 250                 255

Lys Ala Pro Lys Thr Thr Arg Asp Pro Arg Leu Pro Lys Pro Lys Gly
            260                 265                 270
```

```
Gln Thr Val Gly Ser Phe Arg Lys Gly Leu Thr Met Leu Pro Glu Ala
            275                 280                 285

Ile Ser Ala Arg Leu Gly Asp Lys Val Lys Val Ser Trp Lys Leu Ser
        290                 295                 300

Ser Ile Thr Lys Leu Ala Ser Gly Glu Tyr Ser Leu Thr Tyr Glu Thr
305                 310                 315                 320

Pro Glu Gly Ile Val Thr Val Gln Ser Lys Ser Val Val Met Thr Val
                325                 330                 335

Pro Ser His Val Ala Ser Ser Leu Leu Arg Pro Leu Ser Asp Ser Ala
            340                 345                 350

Ala Glu Ala Leu Ser Lys Leu Tyr Tyr Pro Pro Val Ala Ala Val Ser
        355                 360                 365

Ile Ser Tyr Ala Lys Glu Ala Ile Arg Ser Glu Cys Leu Ile Asp Gly
    370                 375                 380

Glu Leu Lys Gly Phe Gly Gln Leu His Pro Arg Thr Gln Lys Val Glu
385                 390                 395                 400

Thr Leu Gly Thr Ile Tyr Ser Ser Ser Leu Phe Pro Asn Arg Ala Pro
                405                 410                 415

Pro Gly Arg Val Leu Leu Leu Asn Tyr Ile Gly Gly Ala Thr Asn Thr
            420                 425                 430

Gly Ile Leu Ser Lys Ser Glu Gly Glu Leu Val Glu Ala Val Asp Arg
        435                 440                 445

Asp Leu Arg Lys Met Leu Ile Lys Pro Ser Ser Thr Asp Pro Leu Val
    450                 455                 460

Leu Gly Val Lys Leu Trp Pro Gln Ala Ile Pro Gln Phe Leu Ile Gly
465                 470                 475                 480

His Ile Asp Leu Val Asp Ala Ala Lys Ala Ser Leu Ser Ser Ser Gly
                485                 490                 495

His Glu Gly Leu Phe Leu Gly Gly Asn Tyr Val Ala Gly Val Ala Leu
            500                 505                 510

Gly Arg Cys Val Glu Gly Ala Tyr Glu Thr Ala Thr Gln Val Asn Asp
        515                 520                 525

Phe Met Ser Arg Tyr Ala Tyr Lys
    530                 535

(2) INFORMATION FOR SEQ ID NO:21:

(i) SEQUENCE CHARACTERISTICS:
        (A) LENGTH: 1224 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Oryza sative (rice)

(vii) IMMEDIATE SOURCE:
        (B) CLONE: pWDC-18 (NRRL B-21648)

(ix) FEATURE:
        (A) NAME/KEY: misc_feature
        (B) LOCATION: 1..936
        (D) OTHER INFORMATION: /product= "Rice Protox-1 partial coding
                                region"

(xi) SEQUENCE DESCRIPTION: SEQ ID NO:21:
```

-continued

```
CGGGCTTTGA AGGCTGCATT TGGGAAGGTG TGGAGGCTGG AGGATACTGG AGGTAGCATT        60

ATTGGTGGAA CCATCAAGAC AATCCAGGAG AGGGGGAAAA ACCCCAAACC GCCGAGGGAT       120

CCCCGCCTTC CAACGCCAAA GGGGCAGACA GTTGCATCTT TCAGGAAGGG TCTGACTATG       180

CTCCCGGATG CTATTACATC TAGGTTGGGT AGCAAAGTCA AACTTTCATG GAAGTTGACA       240

AGCATTACAA AGTCAGACAA CAAAGGATAT GCATTAGTGT ATGAAACACC AGAAGGGGTG       300

GTCTCGGTGC AAGCTAAAAC TGTTGTCATG ACCATCCCAT CATATGTTGC TAGTGATATC       360

TTGCGGCCAC TTTCAAGTGA TGCAGCAGAT GCTCTGTCAA TATTCTATTA TCCACCAGTT       420

GCTGCTGTAA CTGTTTCATA TCCAAAAGAA GCAATTAGAA AAGAATGCTT AATTGACGGA       480

GAGCTCCAGG GTTTCGGCCA GCTGCATCCG CGTAGTCAGG GAGTTGAGAC TTTAGGAACA       540

ATATATAGCT CATCACTCTT TCCAAATCGT GCTCCAGCTG GAAGGGTGTT ACTTCTGAAC       600

TACATAGGAG GTTCTACAAA TACAGGGATT GTTTCCAAGA CTGAAAGTGA GCTGGTAGAA       660

GCAGTTGACC GTGACCTCAG GAAGATGCTG ATAAATCCTA GAGCAGTGGA CCCTTTGGTC       720

CTTGGCGTCC GGGTATGGCC ACAAGCCATA CCACAGTTCC TCATTGGCCA TCTTGATCAT       780

CTTGAGGCTG CAAAATCTGC CCTGGGCAAA GGTGGGTATG ATGGATTGTT CCTCGGAGGG       840

AACTATGTTG CAGGAGTTGC CCTGGGCCGA TGCGTTGAAG GTGCATATGA GAGTGCCTCA       900

CAAATATCTG ACTACTTGAC CAAGTACGCC TACAAGTGAT CAAAGTTGGC CTGCTCCTTT       960

TGGCACATAG ATGTGAGGCT TCTAGCAGCA AAAATTTCAT GGGCATCTTT TTATCCTGAT      1020

TCTAATTAGT TAGAATTTAG AATTGTAGAG GAATGTTCCA TTTGCAGTTC ATAATAGTTG      1080

TTCAGATTTC AGCCATTCAA TTTGTGCAGC CATTTACTAT ATGTAGTATG ATCTTGTAAG      1140

TACTACTAAG AACAAATCAA TTATATTTTC CTGCAAGTGA CATCTTAATC GTCAGCAAAT      1200

CCAGTTACTA GTAAAAAAAA AAAA                                            1224
```

(2) INFORMATION FOR SEQ ID NO:22:

(i) SEQUENCE CHARACTERISTICS:
        (A) LENGTH: 312 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:22:

```
Arg Ala Leu Lys Ala Ala Phe Gly Lys Val Trp Arg Leu Glu Asp Thr
1               5                   10                  15

Gly Gly Ser Ile Ile Gly Gly Thr Ile Lys Thr Ile Gln Glu Arg Gly
            20                  25                  30

Lys Asn Pro Lys Pro Arg Asp Pro Arg Leu Pro Thr Pro Lys Gly
        35                  40                  45

Gln Thr Val Ala Ser Phe Arg Lys Gly Leu Thr Met Leu Pro Asp Ala
    50                  55                  60

Ile Thr Ser Arg Leu Gly Ser Lys Val Lys Leu Ser Trp Lys Leu Thr
65                  70                  75                  80

Ser Ile Thr Lys Ser Asp Asn Lys Gly Tyr Ala Leu Val Tyr Glu Thr
                85                  90                  95

Pro Glu Gly Val Val Ser Val Gln Ala Lys Thr Val Val Met Thr Ile
            100                 105                 110

Pro Ser Tyr Val Ala Ser Asp Ile Leu Arg Pro Leu Ser Ser Asp Ala
        115                 120                 125

Ala Asp Ala Leu Ser Ile Phe Tyr Tyr Pro Pro Val Ala Ala Val Thr
```

```
              130                 135                 140
Val Ser Tyr Pro Lys Glu Ala Ile Arg Lys Glu Cys Leu Ile Asp Gly
145                 150                 155                 160

Glu Leu Gln Gly Phe Gly Gln Leu His Pro Arg Ser Gln Gly Val Glu
                165                 170                 175

Thr Leu Gly Thr Ile Tyr Ser Ser Leu Phe Pro Asn Arg Ala Pro
            180                 185                 190

Ala Gly Arg Val Leu Leu Leu Asn Tyr Ile Gly Gly Ser Thr Asn Thr
            195                 200                 205

Gly Ile Val Ser Lys Thr Glu Ser Glu Leu Val Glu Ala Val Asp Arg
        210                 215                 220

Asp Leu Arg Lys Met Leu Ile Asn Pro Arg Ala Val Asp Pro Leu Val
225                 230                 235                 240

Leu Gly Val Arg Val Trp Pro Gln Ala Ile Pro Gln Phe Leu Ile Gly
                245                 250                 255

His Leu Asp His Leu Glu Ala Ala Lys Ser Ala Leu Gly Lys Gly Gly
            260                 265                 270

Tyr Asp Gly Leu Phe Leu Gly Gly Asn Tyr Val Ala Gly Val Ala Leu
        275                 280                 285

Gly Arg Cys Val Glu Gly Ala Tyr Glu Ser Ala Ser Gln Ile Ser Asp
    290                 295                 300

Tyr Leu Thr Lys Tyr Ala Tyr Lys
305                 310

(2) INFORMATION FOR SEQ ID NO:23:

(i) SEQUENCE CHARACTERISTICS:
        (A) LENGTH: 1590 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Sorghum bicolor (sorghum)

(vii) IMMEDIATE SOURCE:
        (B) CLONE: pWDC-19 (NRRL B-21649)

(ix) FEATURE:
        (A) NAME/KEY: misc_feature
        (B) LOCATION: 1..1320
        (D) OTHER INFORMATION: /product= "Sorghum Protox-1 partial
                               coding region"

(xi) SEQUENCE DESCRIPTION: SEQ ID NO:23:

TCCACCGTCG AGCGCCCCGA GGAAGGGTAC CTCTGGGAGG AGGGTCCCAA CAGCTTCCAG     60

CCATCCGACC CCGTTCTCTC CATGGCCGTG GACAGCGGGC TGAAGGATGA CCTGGTTTTT    120

GGGGACCCCA ACGCGCCACG GTTCGTGCTG TGGGAGGGGA AGCTGAGGCC CGTGCCATCC    180

AAGCCCGCCG ACCTCCCGTT CTTCGATCTC ATGAGCATCC CTGGCAAGCT CAGGGCCGGT    240

CTCGGCGCGC TTGGCATCCG CCCGCCTGCT CCAGGCCGCG AGGAGTCAGT GGAGGAGTTT    300

GTGCGCCGCA ACCTCGGTGC TGAGGTCTTT GAGCGCCTAA TTGAGCCTTT CTGCTCAGGT    360

GTCTATGCTG GCGATCCTTC CAAGCTCAGT ATGAAGGCTG CATTTGGGAA GGTGTGGCGG    420

TTAGAAGAAG CTGGAGGTAG TATTATTGGT GGAACCATCA AGACGATTCA GGAGAGGGGC    480
```

-continued

```
AAGAATCCAA AACCACCGAG GGATCCCCGC CTTCCGAAGC CAAAAGGGCA GACAGTTGCA        540

TCTTTCAGGA AGGGTCTTGC CATGCTTCCA AATGCCATCA CATCCAGCTT GGGTAGTAAA        600

GTCAAACTAT CATGGAAACT CACGAGCATG ACAAAATCAG ATGGCAAGGG GTATGTTTTG        660

GAGTATGAAA CACCAGAAGG GGTTGTTTTG GTGCAGGCTA AAAGTGTTAT CATGACCATT        720

CCATCATATG TTGCTAGCGA CATTTTGCGT CCACTTTCAG GTGATGCTGC AGATGTTCTA        780

TCAAGATTCT ATTATCCACC AGTTGCTGCT GTAACGGTTT CGTATCCAAA GGAAGCAATT        840

AGAAAAGAAT GCTTAATTGA TGGGGAACTC CAGGGTTTTG GCCAGTTGCA TCCACGTAGT        900

CAAGGAGTTG AGACATTAGG AACAATATAC AGCTCATCAC TCTTTCCAAA TCGTGCTCCT        960

GCTGGTAGGG TGTTACTTCT AAACTACATA GGAGGTGCTA CAAACACAGG AATTGTTTCC       1020

AAGACTGAAA GTGAGCTGGT AGAAGCAGTT GACCGTGACC TCCGAAAAAT GCTTATAAAT       1080

CCTACAGCAG TGGACCCTTT AGTCCTTGGT GTCCGAGTTT GGCCACAAGC CATACCTCAG       1140

TTCCTGGTAG GACATCTTGA TCTTCTGGAG GCCGCAAAAT CTGCCCTGGA CCAAGGTGGC       1200

TATAATGGGC TGTTCCTAGG AGGGAACTAT GTTGCAGGAG TTGCCCTGGG CAGATGCATT       1260

GAGGGCGCAT ATGAGAGTGC CGCGCAAATA TATGACTTCT TGACCAAGTA CGCCTACAAG       1320

TGATGGAAGA AGTGGAGCGC TGCTTGTTAA TTGTTATGTT GCATAGATGA GGTGAGACCA       1380

GGAGTAGTAA AAGGCGTCAC GAGTATTTTT CATTCTTATT TTGTAAATTG CACTTCTGTT       1440

TTTTTTTCCT GTCAGTAATT AGTTAGATTT TAGTTATGTA GGAGATTGTT GTGTTCACTG       1500

CCCTACAAAA GAATTTTTAT TTTGCATTCG TTTATGAGAG CTGTGCAGAC TTATGTAACG       1560

TTTTACTGTA AGTATCAACA AAATCAAATA                                       1590
```

(2) INFORMATION FOR SEQ ID NO:24:

(i) SEQUENCE CHARACTERISTICS:
        (A) LENGTH: 440 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:24:

```
Ser Thr Val Glu Arg Pro Glu Glu Gly Tyr Leu Trp Glu Glu Gly Pro
  1               5                  10                  15

Asn Ser Phe Gln Pro Ser Asp Pro Val Leu Ser Met Ala Val Asp Ser
             20                  25                  30

Gly Leu Lys Asp Asp Leu Val Phe Gly Asp Pro Asn Ala Pro Arg Phe
         35                  40                  45

Val Leu Trp Glu Gly Lys Leu Arg Pro Val Pro Ser Lys Pro Ala Asp
     50                  55                  60

Leu Pro Phe Phe Asp Leu Met Ser Ile Pro Gly Lys Leu Arg Ala Gly
 65                  70                  75                  80

Leu Gly Ala Leu Gly Ile Arg Pro Pro Ala Pro Gly Arg Glu Glu Ser
                 85                  90                  95

Val Glu Glu Phe Val Arg Arg Asn Leu Gly Ala Glu Val Phe Glu Arg
            100                 105                 110

Leu Ile Glu Pro Phe Cys Ser Gly Val Tyr Ala Gly Asp Pro Ser Lys
        115                 120                 125

Leu Ser Met Lys Ala Ala Phe Gly Lys Val Trp Arg Leu Glu Glu Ala
    130                 135                 140

Gly Gly Ser Ile Ile Gly Gly Thr Ile Lys Thr Ile Gln Glu Arg Gly
145                 150                 155                 160
```

```
Lys Asn Pro Lys Pro Pro Arg Asp Pro Arg Leu Pro Lys Pro Lys Gly
            165                 170                 175

Gln Thr Val Ala Ser Phe Arg Lys Gly Leu Ala Met Leu Pro Asn Ala
        180                 185                 190

Ile Thr Ser Ser Leu Gly Ser Lys Val Lys Leu Ser Trp Lys Leu Thr
        195                 200                 205

Ser Met Thr Lys Ser Asp Gly Lys Gly Tyr Val Leu Glu Tyr Glu Thr
    210                 215                 220

Pro Glu Gly Val Val Leu Val Gln Ala Lys Ser Val Ile Met Thr Ile
225                 230                 235                 240

Pro Ser Tyr Val Ala Ser Asp Ile Leu Arg Pro Leu Ser Gly Asp Ala
            245                 250                 255

Ala Asp Val Leu Ser Arg Phe Tyr Tyr Pro Pro Val Ala Ala Val Thr
            260                 265                 270

Val Ser Tyr Pro Lys Glu Ala Ile Arg Lys Glu Cys Leu Ile Asp Gly
            275                 280                 285

Glu Leu Gln Gly Phe Gly Gln Leu His Pro Arg Ser Gln Gly Val Glu
        290                 295                 300

Thr Leu Gly Thr Ile Tyr Ser Ser Ser Leu Phe Pro Asn Arg Ala Pro
305                 310                 315                 320

Ala Gly Arg Val Leu Leu Leu Asn Tyr Ile Gly Gly Ala Thr Asn Thr
            325                 330                 335

Gly Ile Val Ser Lys Thr Glu Ser Glu Leu Val Glu Ala Val Asp Arg
            340                 345                 350

Asp Leu Arg Lys Met Leu Ile Asn Pro Thr Ala Val Asp Pro Leu Val
            355                 360                 365

Leu Gly Val Arg Val Trp Pro Gln Ala Ile Pro Gln Phe Leu Val Gly
        370                 375                 380

His Leu Asp Leu Leu Glu Ala Ala Lys Ser Ala Leu Asp Gln Gly Gly
385                 390                 395                 400

Tyr Asn Gly Leu Phe Leu Gly Gly Asn Tyr Val Ala Gly Val Ala Leu
            405                 410                 415

Gly Arg Cys Ile Glu Gly Ala Tyr Glu Ser Ala Ala Gln Ile Tyr Asp
            420                 425                 430

Phe Leu Thr Lys Tyr Ala Tyr Lys
            435                 440

(2) INFORMATION FOR SEQ ID NO:25:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "maize protox-1 intron sequence"

(xi) SEQUENCE DESCRIPTION: SEQ ID NO:25:

GTACGCTCCT CGCTGGCGCC GCAGCGTCTT CTTCTCAGAC TCATGCGCAG CCATGGAATT      60

GAGATGCTGA ATGGATTTTA TACGCGCGCG CAG                                   93

(2) INFORMATION FOR SEQ ID NO:26:

(i) SEQUENCE CHARACTERISTICS:
        (A) LENGTH: 2606 base pairs
        (B) TYPE: nucleic acid
        (C) STRANDEDNESS: single
```

(D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Beta vulgaris (sugar beet)

(vii) IMMEDIATE SOURCE:
        (B) CLONE: pWDC-20 (NRRL B-21650)

(ix) FEATURE:
        (A) NAME/KEY: misc_feature
        (B) LOCATION: 1..6
        (D) OTHER INFORMATION: /note= "SalI site"

(ix) FEATURE:
        (A) NAME/KEY: misc_feature
        (B) LOCATION: complement (1..538)
        (D) OTHER INFORMATION: /note= "partial cDNA of sugar beet
                                protox-1 in 3' - 5' direction"

(ix) FEATURE:
        (A) NAME/KEY: misc_feature
        (B) LOCATION: 539..2606
        (D) OTHER INFORMATION: /note= "sugar beet protox-1 promoter
                                region presented in 3' - 5' direction
                                (partial sequence of the [] 3 kb
                                PstI-SalI fragment subcloned from
                                pWDC-20)"

(xi) SEQUENCE DESCRIPTION: SEQ ID NO:26:

```
GTCGACCTAC GCACATGCCA CATTCCACAT TCCACGTTAG GAATTGAATT GAATTGAATT      60

ATGATTATGA ATAATGAAGA GACAGAATTA CCGCCATGGT GAGCACCGCG TCGGAAGGCT     120

GGAAGCTATT GGGTCCCTCC TCCCAGATAT AGCCATCGGC CTCCACAGTG ACGATGTTGC     180

CGCCAACTCT GTCTTTGGCC TCTGTCACTA TAAAATTTGG GGATAAAGAG GACTGTTTTG     240

TACAAAGAGC CTGCGCGATG CAAAGCCCGC TAATTCCACC TCCAACGATT ACGCAGTCTA     300

GCAATCCTCC TGCTCCTGAT CCTGATCCTG ATCCTGCTTC TTTAACCGCT GACTTTGAGC     360

CTGAGCTTGT GCTGCAACTC ATGCTCATCC TCCTCTTCTT ATGTGAATAA TAACCTCGTC     420

TTCCAATTAA ACTACATGGA ATTGACAACA TGATACAATT GCCCCTGTAA TGCCCGCTGC     480

TGTGCAATGG CATGCACTGT GTCTGTGGAA TGCAGTTTGA TAACGCCATT GATTTCATCT     540

CTCTCTCGCT CTCTCGCCCT CCTTATCCTC TATATCCCCT TCTTGCTTGC TCGGGAATTC     600

TAATTAACCT TATATCAAAA TGAAACAACT GTTTCTAGTT AAAAAGTTTT TTATAAATAG     660

TACTCTAAAT AAACGATTAC ATGTATCTTC TAACCATACT TGTTTGGTGG AGGTGGTGCG     720

TAACCGGTAA CTTACCTTTG TAACTCACCT CAATACCTAC TTATGCTTAA GGATACGGAT     780

TCTTTTAAAC TCTCAGGCAT TGACCTATGT AGCTGGACTG ACTAACATCT GAATTTGTTT     840

CTCTGGTTAT ATATGCAATT TTAACTGAAT CGAAATTTCT CTGGATGCTA AAAATGTCTT     900

TAACGGGGTT TATGAGGACT AAATTATCTC CTTCAATGAG GAGGTTCTTG ATTTGCATGT     960

ATGAGCGTGA AAATGCATTC TTAACGGCTA TAGATTCAGT AATAAGTGGT GTTAAAAGTA    1020

AAAAGTACTT GGAAAAATGA TTAAGCGACT TAATTTTTTT TATTTGTTTG AAAGTTGCCT    1080

TTTCTTGGCT ATCTTAACAT GTATTTATCA AACACCTTTT TTAATTACAT GGAAATCGAA    1140

AAGTTTGAAA AAAAAAAATC ATACTCACTA ACCGCCTTAA AATATAAGCT GAAGATGTCT    1200

CACTAACAGA GTGCATGTGA AGCACCCCCA AAGCAATTAT AACACAACAT CTCCGCCTCT    1260

TCAAAATTCC TACAAATACA TCTAATAAAC TTGTTGAAAC AATCAAAGTA ACATGGTGTG    1320
```

```
TCAATTGCGG ATGCTTCTCA TTCCAGACTT TATATAGTGA TTTTGTTTAA TCCATAGTCA    1380

ACAACTCACA TAATGGTACC CAAAGAATAC CCAAATTTTT TGCTCAAAAT CCCTAAACAT    1440

TGTAGCTGTG TAAGTTTGAC TAACATGTTT CAGCATGCTT GCCATGGGTA AATAAGACTT    1500

AGGGGCAAAT CTCGAATCCA CAAACTCATC ATTGGTTTTA GTTTGTCTCC AACGTAAAAC    1560

AATGATGTGA ATACACCAC AAAATTCATA CAATCTCGTT ATCTTGGAAG CTTGAAAGCC     1620

ATAATCTTGT TTGTACTTTC ACTACGTCGA GAAGACAAAA TTACAACTAA GAAGAGGTCA    1680

TTGCTCAGTG TCGTGTACTA CTTATCTTTC AACTCATAGA AACAAGCAAA CCAATTGTCA    1740

CCTATATACT GTACTTCTCC ATCATATACT TCCAACTTGC CTTAAACTCA ATACTATCAT    1800

AAAAACCACA AAGACATTTC ATAAAAGCAT AATAAAAATG TGTCATCACT CTTCAAAGTT    1860

CCAAAGTGAT TCTAACTACA TTCTAATGAA AATGACATTG GTGTAAACCT AATCCTTGTG    1920

TTATAAAACA CCTACATACC ACGATTATGT TAGAAATATA TTTATGAATG CAGTACCTAC    1980

ATAAAGCCAT TAAATAACCA GTTTTATGTT ATTTCGTGAC CAACATAGTT CCTAAAGATT    2040

ACGAAGTAAT TTATAGTCAT TTTGTGGCCA CTTAATTCAT TTAATACCCA GTATATTTAT    2100

AAGTTACCAG CTTAAGTAGT TTTGTGACCA TCTCTACATA CTTCCTCCGG TCCATAATAA    2160

GGGGGCGTTT GGTTGCAACG GGGTAAAGGG AATGGAATCA AGAAAGGGAG AGGAGAGGAA    2220

AGGAAAAGAA AACCCTTAGA TTTAGAGTGG TGTTTGGTTA AGATAATGTT AATTCTCTTT    2280

CTTCCTCTTT CTTACCCTTC TTCCACCCTA GCACCACCAC TCCTCCCTCT GTTACTATTC    2340

TCCACGCCGC CTCTCCCTAC CCCAGTAACA CCACCTTGTC GGCCCCCCGG TCTTCCCCTT    2400

CCCGCGACGG TTCCCCCCTC CCCTGCGCCG TCACGTCGTC CCCCTCACCT CCCTGCACCG    2460

TCGAGTTATC CCCCTCCCCT GCGCGTCGCG TTCTCCCCTC CCTCACCATC GCGTTCTCCC    2520

CTCCCTCACC GTCGCGTTCT CCCCTCCCTC ACCGTCGCGG TCTCCCCTCC CTCACCGTCG    2580

CGGTCTCTCT TTCCCTCCCC CTGCAG                                        2606
```

(2) INFORMATION FOR SEQ ID NO:27:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: other nucleic acid
       (A) DESCRIPTION: /desc = "Pclp_P1a - plastid clpP gene
                       promoter top strand PCR primer"

(iii) HYPOTHETICAL: NO (iv) ANTI-SENSE: NO (ix) FEATURE:
       (A) NAME/KEY: misc_feature
       (B) LOCATION: 4..9
       (D) OTHER INFORMATION: /note= "EcoRI restriction site"

(xi) SEQUENCE DESCRIPTION: SEQ ID NO:27:

GCGGAATTCA TACTTATTTA TCATTAGAAA G                                   31

(2) INFORMATION FOR SEQ ID NO:28:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: other nucleic acid (A) DESCRIPTION: /desc = "Pclp_Plb - plastid clpP gene
    promoter bottom strand PCR primer"

(iii) HYPOTHETICAL: NO (iv) ANTI-SENSE: NO (ix) FEATURE:
    (A) NAME/KEY: misc_feature
    (B) LOCATION: 4..9
    (D) OTHER INFORMATION: /note= "XbaI restriction site"

(xi) SEQUENCE DESCRIPTION: SEQ ID NO:28:

GCGTCTAGAA AGAACTAAAT ACTATATTTC AC        32

(2) INFORMATION FOR SEQ ID NO:29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Pclp_P2b - plastid clpP gene
            promoter bottom strand PCR primer"

(iii) HYPOTHETICAL: NO (iv) ANTI-SENSE: NO (ix) FEATURE:
        (A) NAME/KEY: misc_feature
        (B) LOCATION: 4..9
        (D) OTHER INFORMATION: /note= "NcoI restriction site"

(xi) SEQUENCE DESCRIPTION: SEQ ID NO:29:

GCGCCATGGT AAATGAAAGA AAGAACTAAA        30

(2) INFORMATION FOR SEQ ID NO:30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Trps16_Pla - plastid rps16 gene 3'
            untranslated region XbaI/HindIII top strand
            PCR primer"

(iii) HYPOTHETICAL: NO (iv) ANTI-SENSE: NO (ix) FEATURE:
        (A) NAME/KEY: misc_feature
        (B) LOCATION: 4..9
        (D) OTHER INFORMATION: /note= "XbaI restriction site"

(xi) SEQUENCE DESCRIPTION: SEQ ID NO:30:

GCGTCTAGAT CAACCGAAAT TCAATTAAGG        30

(2) INFORMATION FOR SEQ ID NO:31:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Trps16_plb - plastid rps16 gene 3' untranslated region XbaI/HindIII bottom
strand PCR primer"

(iii) HYPOTHETICAL: NO (iv) ANTI-SENSE: NO (ix) FEATURE:
    (A) NAME/KEY: misc_feature
    (B) LOCATION: 4..9
    (D) OTHER INFORMATION: /note= "HindIII restriction site"

(xi) SEQUENCE DESCRIPTION: SEQ ID NO:31:

CGCAAGCTTC AATGGAAGCA ATGATAA                    27

(2) INFORMATION FOR SEQ ID NO:32:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "minpsb_U - plastid psbA gene 5'
              untranslated region 38 nt (blunt/NcoI)
              including ATG start codon, top strand primer"

(iii) HYPOTHETICAL: NO (iv) ANTI-SENSE: NO (xi) SEQUENCE DESCRIPTION: SEQ ID NO:32:

GGGAGTCCCT GATGATTAAA TAAACCAAGA TTTTAC            36

(2) INFORMATION FOR SEQ ID NO:33:

(i) SEQUENCE CHARACTERISTICS:
    (A) LENGTH: 40 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "minpsb_L - plastid psbA gene 5'
              untranslated region 38 nt (blunt/NcoI)
              including ATG start codon (bottom strand
              primer)"

(iii) HYPOTHETICAL: NO (iv) ANTI-SENSE: NO (xi) SEQUENCE DESCRIPTION: SEQ ID NO:33:

CATGGTAAAA TCTTGGTTTA TTTAATCATC AGGGACTCCC      40

(2) INFORMATION FOR SEQ ID NO:34:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "APRTXP1a - top strand PCR primer for
              amplifying the 5' portion of the mutant
              Arabidopsis protox gene"

(iii) HYPOTHETICAL: NO (iv) ANTI-SENSE: NO (ix) FEATURE:

-continued

```
        (A) NAME/KEY: misc_feature
        (B) LOCATION: 5..10
        (D) OTHER INFORMATION: /note= "NcoI restriction site/ATG start
                                       codon"

(xi) SEQUENCE DESCRIPTION: SEQ ID NO:34:

GGGACCATGG ATTGTGTGAT TGTCGGCGGA GG                                    32

(2) INFORMATION FOR SEQ ID NO:35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "APRTXP1b - bottom strand PCR primer
                                  for amplifying the 5' portion of the mutant
                                  Arabidopsis protox gene"

(iii) HYPOTHETICAL: NO (iv) ANTI-SENSE: NO (xi) SEQUENCE DESCRIPTION: SEQ ID NO:35:

CTCCGCTCTC CAGCTTAGTG ATAC                                             24
```